(12) United States Patent
Sierra-Honigmann

(10) Patent No.: US 7,261,881 B1
(45) Date of Patent: Aug. 28, 2007

(54) MODULATION OF ANGIOGENESIS AND WOUND HEALING

(75) Inventor: Rocio M. Sierra-Honigmann, Thousand Oaks, CA (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/700,813

(22) PCT Filed: May 20, 1999

(86) PCT No.: PCT/US99/11209

§ 371 (c)(1),
(2), (4) Date: Mar. 14, 2001

(87) PCT Pub. No.: WO99/59614

PCT Pub. Date: Nov. 25, 1999

(51) Int. Cl.
*A61K 45/00* (2006.01)

(52) U.S. Cl. .................. 424/85.1; 424/198.1; 514/12; 530/351; 530/300

(58) Field of Classification Search ............... None
See application file for complete search history.

(56) References Cited

U.S. PATENT DOCUMENTS

| | | |
|---|---|---|
| 4,778,787 A | 10/1988 | Catsimpoolas et al. |
| 5,112,946 A | 5/1992 | Maione |
| 5,137,734 A | 8/1992 | Spiegelman et al. |
| 5,219,740 A | 6/1993 | Miller et al. |
| 5,227,302 A | 7/1993 | Heldin et al. |
| 5,283,173 A | 2/1994 | Fields et al. |
| 5,470,831 A | 11/1995 | Whitman et al. |
| 5,500,412 A | 3/1996 | Carney et al. |
| 5,585,089 A | 12/1996 | Queen et al. |
| 5,591,716 A | 1/1997 | Siebert et al. |
| 5,624,820 A | 4/1997 | Cooper |
| 5,641,483 A | 6/1997 | Beaulieu |
| 5,641,508 A | 6/1997 | Li et al. |
| 5,662,904 A | 9/1997 | Ferguson et al. |
| 5,677,181 A | 10/1997 | Parish |
| 5,679,655 A | 10/1997 | Gallina |
| 5,686,278 A | 11/1997 | Williams et al. |
| 5,705,342 A | 1/1998 | Bischoff et al. |
| 5,705,477 A | 1/1998 | Sporn et al. |
| 5,707,618 A | 1/1998 | Armentano et al. |
| 5,710,037 A | 1/1998 | Vanin et al. |
| 5,712,115 A | 1/1998 | Hawkins et al. |
| 5,714,353 A | 2/1998 | Pathak et al. |
| 5,728,379 A | 3/1998 | Martuza et al. |
| 5,731,190 A | 3/1998 | Wickham et al. |
| 5,879,713 A * | 3/1999 | Roth et al. .................. 424/489 |
| 6,203,991 B1 * | 3/2001 | Nabel et al. .................. 435/6 |
| 6,290,949 B1 * | 9/2001 | French et al. .............. 424/93.2 |

OTHER PUBLICATIONS

Bai, et al., 1996, J. Biol. Chem. 271:13939-13942.
Blanck, et al., 1987, J. Cell. Biol. 105:139(A).
Campfield, et al., 1996, Horm. Metab. Res. 28:619-632.
Caro, et al., 1996, Lancet 348:159-161.
Considine, et al., 1996, N. Engl. J. Med. 334:292-295.
Crandell, et al., 1997, Microcirculation 4:211-232.
Fields, et al., 1990, Int. J. Proc. Protein. Res. 35:161-214.
Flier, 1997, Proc. Nat'l Acad. Sci. USA 94:4242-4245.
Gainsford, et al., 1996, Proc. Nat'l. Acad. Sci. USA 93:14564-14568.
Garcia-Cardena, et al., 1996, Proc. Nat'l Acad. Sci. USA 93:6448-6453.
Garnier, 1978, J. Mol. Bio. 120:97-120.
Ghilardi, et al., 1997, Mol. Endocrinol. 11:393-399.
Girard, 1997, Diabetes Metabol. 23:16-24.
Hassink, et al., 1997, Pediatrics 100:123-128.
Heritier, et al., 1997, Neurosci. Res. Commun. 21:113-118.
Herrera, et al., 1994, Proc. Nat'l Acad. Sci. USA 91:12999-13003.
Hoggard, et al., 1997, Biochem. Biophys. Res. Commun. 232:383-387.
Hoggard, et al., 1997, Proc. Nat'l. Acad. Sci. USA 94:11073-11078.
Hopp, et al., 1981, Proc. Nat'l Acad. Sci. USA 78:3824-3828.
Howard, et al., 1997, Clin. Sci. 93:119-126.
Kohler, et al., 1976, Eur. J. Immunol. 6:511-519.
Kundra, et al., 1995, J. Cell. Biol. 130:725-731.
Lee, et al., 1996, Nature 379:632-635.
Liu, et al., 1997, Endocrinology 138:3548-3554.
MacDougald, et al., 1995, Proc. Nat'l Acad. Sci. USA 92:9034-9037.
Mandrup, et al., 1997 Proc. Nat'l Acad. Sci. USA 94:4300-4305.
Mercer, et al., 1996, FEBS Letters 387:113-116.
Mikhail, et al., 1997, Blood 89:1507-1512.
Muoio, et al., 1997, Diabetes 48:1360-1363.
Mustoe, et al., 1987, Science, 237:1333-1336.
Negro, et al., 1996, Eur. J. Biochem. 241:507-515.
Riechmann, et al., 1988, Nature 332:323-327.
Sarmiento, et al., 1997, Lab. Invest. 77:243-256.
Savioz, et al., 1997, Neuroreport 8:3123-3126.
Schultz, et al., 1991, Eye 5:170-180.
Schwartz, et al., 1997, N. Engl. J. Med. 336:1802-1811.

(Continued)

*Primary Examiner*—Gary Nickol
*Assistant Examiner*—Gyan Chandra
(74) *Attorney, Agent, or Firm*—Seth D. Levy; Davis Wright Tremaine LLP

(57) ABSTRACT

Methods of regulating angiogenesis, ischemic injury and/or wound healing by modulating the activity of leptin, particularly as mediated by the leptin receptor, and/or the interaction between leptin and the leptin receptor. Correspondingly, these methods can also be used to treat diseases mediated by angiogenesis, including wound healing, tumors and tumor metastasis, diabetic microangiopathy, retinal neovascularization, neovascularization of adipose tissue and fat metabolism, revascularization of necrotic tissue, enhancement or vascularization in microvascular transplants, and ovarian follicle maturation. Assays for identifying agents that modulate leptin and/or leptin receptor-mediated angiogenesis and/or wound healing and their use in treating angiogenesis-mediated diseases or conditions involving wound healing are also disclosed.

3 Claims, 24 Drawing Sheets

OTHER PUBLICATIONS

Figure 1A:
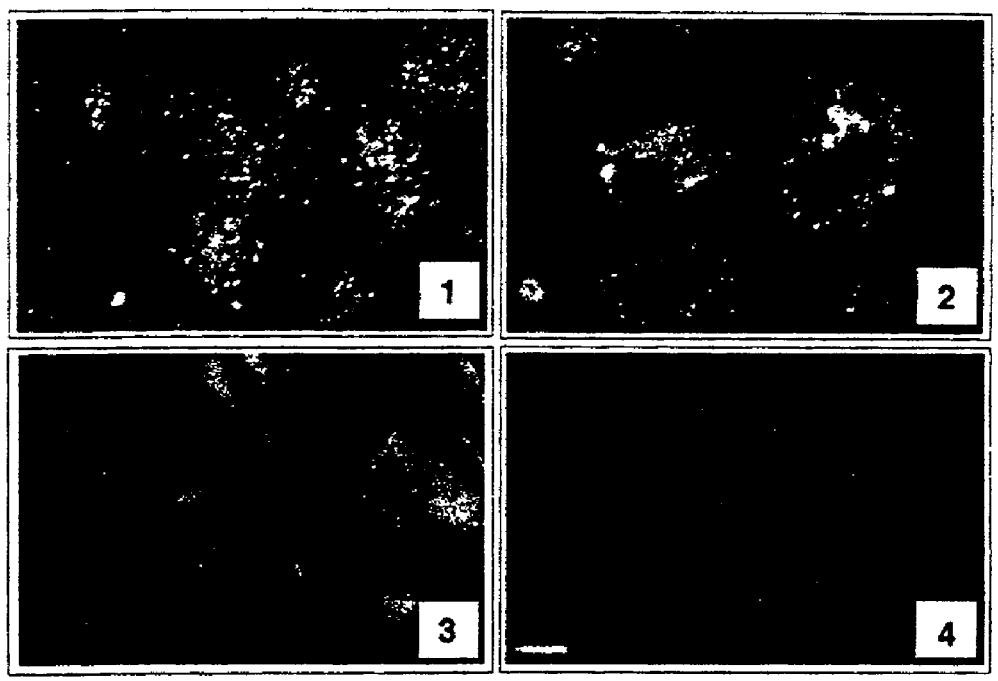

Seyedin, et al., 1986, J. Biol. Chem. 261:5693-5695.
Shimabukuro, et al., 1997, Proc. Nat'l Acad. Sci. USA 94:4637-4641.
Sierra-Honigmann, et al., 1996, Lab Invest 74:684-695.
Sierra-Honigmann, et al., 1998, Science 281:1683-1686.
Smith, et al., 1982, J. Invest Dermatol. 79:93s-104s.
Tartaglia, et al., 1995, Cell 83:1263-1271.
Turkson, et al., 1998, Mol. Cell. Biol. 18:2545-2552.
Wang, et al., 1996, FEBS Letters 392:87-90.
Wang, et al., 1997, J. Biol Chem. 272:16216-16223.
Wickham, et al., 1996, J. Virol. 70:6831-6838.

* cited by examiner

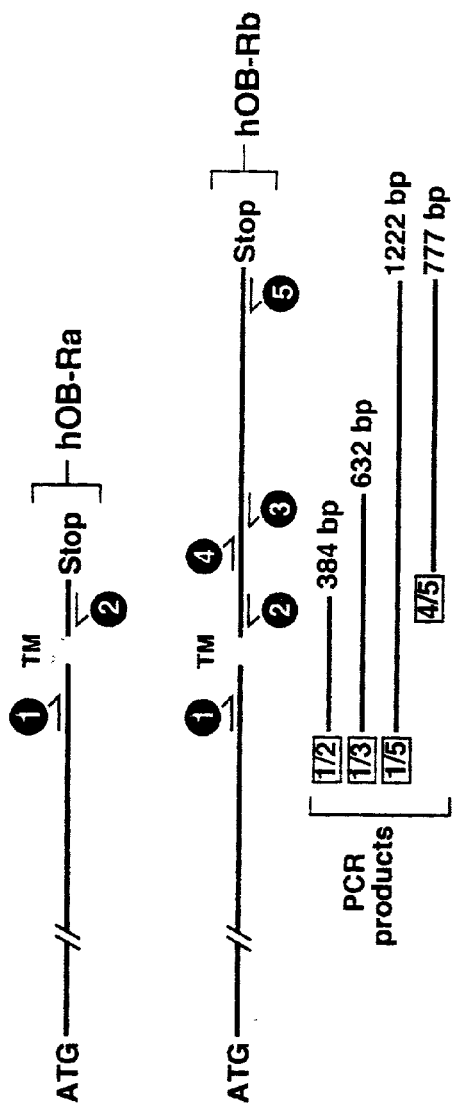
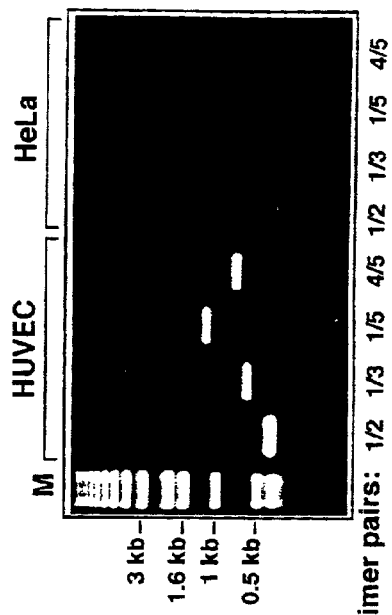
FIG. IC

FIG. 3

HUVEC NON-TREATED CONTROL. CELLS DISPLAY NORMAL MORPHOLOGY. STAINING OF NUCLEI WITH DAPI(BLUE), AND CELL SURFACE WITH TRITC-LABELLED *ULEX EUROPEOUS* LECTIN(RED)

HUVEC TREATED WITH 10 nM HUMAN RECOMBINANT LEPTIN FOR 24 HOURS. CELLS BECOME ELONGATED AND ARRANGE INTO CORD-LIKE STRUCTURES AND CLOSED CIRCLES. DOUBLE EXPOSURE PHOTOGRAPH. STAINING OF NUCLEI WITH DAPI(BLUE), AND CELL SURFACE WITH TRITC-LABELLED *ULEX EUROPEOUS* LECTIN(RED).

IMMUNOFLUORESCENCE IMAGE CAPTURED BY CONFOCAL MICROSCOPE OF HUVEC TREATED WITH 10 nM HUMAN RECOMBINANT LEPTIN FOR 24 HOURS. STAINING OF WITH ANTI-Ob-Rb (LONG FORM OF LEPTIN RECEPTOR) ANTIBODIES. THE INTRACELLULAR DISTRIBUTION OF THE RECEPTOR APPEARS IN LARGE CLUSTERS OR VESICLES.

IMMUNOFLUORESCENCE IMAGE CAPTURED BY CONFOCAL MICROSCOPE OF HUVEC TREATED WITH 10 nM HUMAN RECOMBINANT LEPTIN FOR 24 HOURS. STAINING OF WITH ANTI-Ob-Rb (LONG FORM OF LEPTIN RECEPTOR) ANTIBODIES. THE INTRACELLULAR DISTRIBUTION OF THE RECEPTOR APPEARS IN LARGE CLUSTERS OR VESICLES.

IMMUNOFLUORESCENCE IMAGE CAPTURED BY CONFOCAL MICROSCOPE OF CONTROL NON-TREATED HUVEC. STAINING OF WITH ANTI-Ob-Rb (LONG FORM OF LEPTIN RECEPTOR) ANTIBODIES. THE RECEPTOR DISTRIBUTION IS DIFUSE ON PLASMA MEMBRANE, IN LARGE VESICLES AND NUCLEAR.

FIG. 8

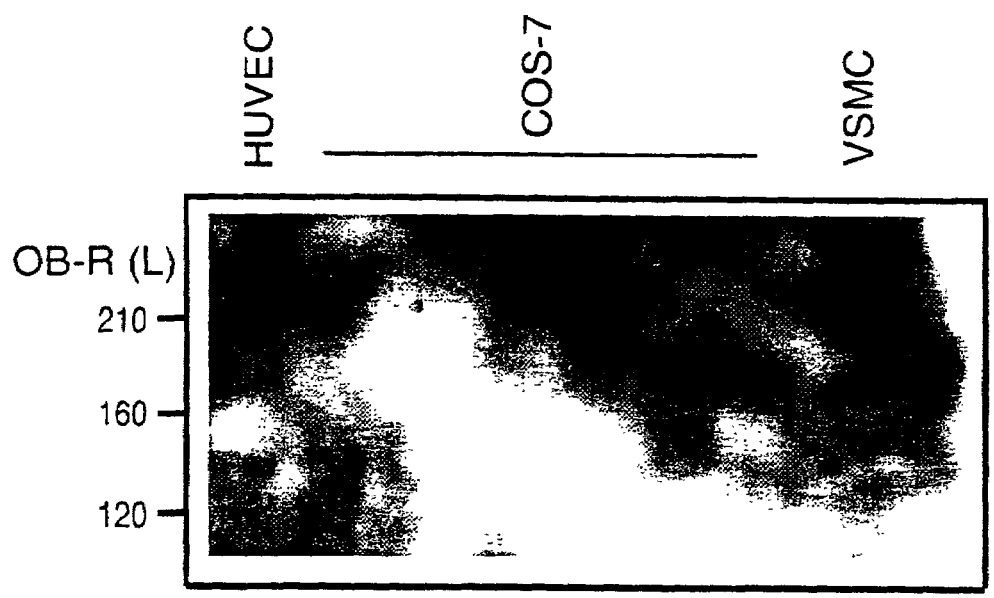

WESTERN BLOT ANALYSIS OF TOTAL CELL EXTRACS.
Primary cultures of human umbillical vein endothelial cells (HUVEC), simian epithelial cell line (COS-7) and primary culture of human vascular smooth muscle cells derived from aorta (VSMC).
Method: 5% SDS-PAGE followed by electrotransference onto nitrocellulose membrane. Immunostaining using rabbit polyclonal serum anti human Ob-R(L).

FIG. 9B
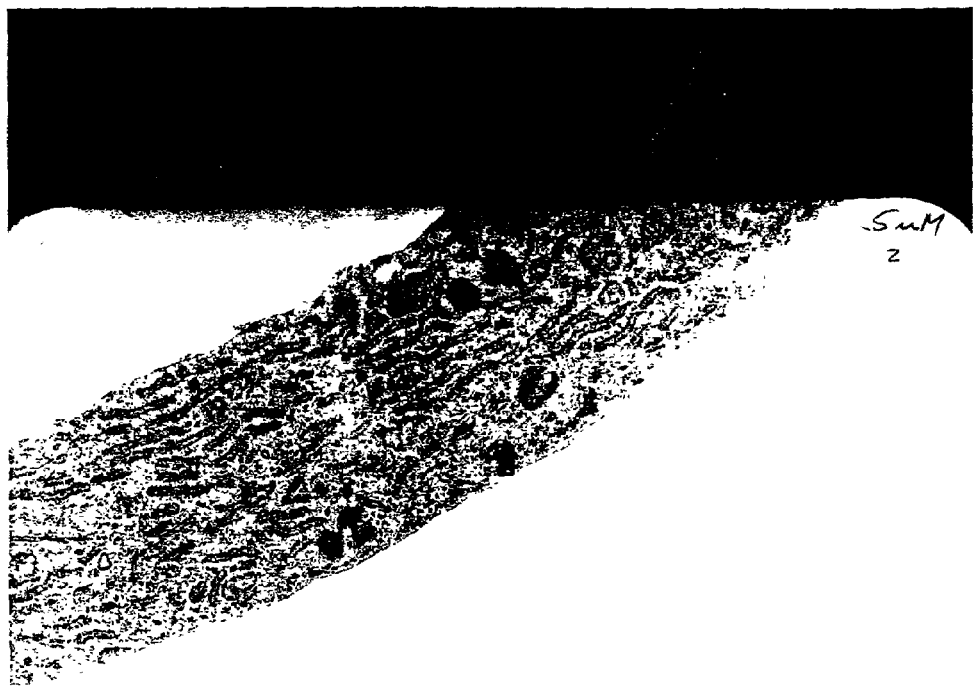

MODULATION OF ANGIOGENESIS AND WOUND HEALING

FIELD OF THE INVENTION

The present invention generally relates to methods for modulating the angiogenic response of a subject to angiogenesis-inducing stimuli or angiogenesis-inhibiting stimuli, such as are released from tumor cells or cells in wounds or ischemic or injured tissues. Specifically, the invention relates to modulating the leptin and leptin-receptor mediated response of endothelial cells and smooth muscle cells to such angiogenic stimuli. Applications of the present invention include enhancing wound healing and/or repair of ischemic tissue and inhibiting the vascularization of tumors and intraocular angiogenesis on the retina or other structures of the eye.

BACKGROUND

1. Leptin

Leptin is produced from the obese (ob) gene and binds to the ob receptors (Ob-R). The ob gene is expressed in various tissues such as placenta, ovaries, muscle and adipose tissue. Leptin is produced in the adipocyte and in ovaries, and is a circulating 16 kDa protein (G. A. Bray, (1996) *Lancet* 348: 140; C. Liu et al., (1997) *Endocrinology* 138: 3548). Defective production of leptin results in gross obesity and type 2 diabetes in the obese (ob/ob) mouse. In humans, the leptin protein levels have been correlated to the percentage of body fat and is elevated in obese patients (R. V. Considine et al., (1996) *N. Engl. J. Med.* 334: 292). Defects in the leptin receptor, Ob-Rb, produces a syndrome in the mutant diabetic db/db mouse that is phenotypically identical to that observed in the ob/ob mouse. In addition to obesity, leptin is also believed to modulate estrogen expression and the fat stores needed for reproduction purposes. Other potential roles for leptin include regulation of hemopoiesis and macrophage function (T. Gainforth et al., (1996) *Proc. Nat'l Acad. Sci. USA* 93: 14564).

Leptin has been detected in the plasma of normal individuals and individuals receiving hemodialysis and in renal transplant patients, in placental tissue from pregnant women, and in cord blood of newborns (Respectively, J. K. Howard et al., (1997) *Clin. Sci.* 93: 119; S. G. Hassink et al., (1997) *Pediatrics* 100: 123). It has been suggested that leptin concentrations in newborns cannot be explained by adiposity alone. In women, leptin deficiency has been postulated to be involved with delayed puberty, menstrual disturbances and anorexia nervosa (M. Schwartz et al., (1997) *N. Engl. J. Med.* 336: 1802). Leptin is also believed to regulate lipid metabolism, glucose uptake, β-cell function, gonadotropin secretion, sympathetic tone, ovarian function and thermogenesis. Glucocorticoids and insulin increase leptin production. Administration of leptin reduces food intake, decreases insulin concentrations, and lowers blood glucose concentrations in the ob/ob mouse, but not in the db/db mouse (G. A. Bray, (1996) *Lancet* 348: 140).

2. The Leptin Receptor

The leptin receptor belongs to the cytokine superfamily of receptors. Several forms of the leptin receptor are expressed in humans and rodents (G. A. Bray, (1996) *Lancet* 348: 140). The short form (Ob-R(S)), considered to have limited signaling capability, is detected in many organs and has 5 identified isoforms, Ob-Ra, Ob-Rc, Ob-Rd, Ob-Re, and r-Ob-Rf (M.-Y. Wang et al., (1996) *FEBS Letters* 392: 87). Ob-R(S) has been identified in the choroid plexus and may be involved in the transport of leptin across the blood-brain barrier (J. Girard, (1997) *Diabetes Metabol.* 23S: 16).

It is the long form of the leptin receptor which is believed to mediate the biological effects of the leptin protein (L. A. Campfield et al., (1996) *Horm. Metab. Res.* 28: 619). In contrast to the short form of the leptin receptor, Ob-R long form (Ob-R(L) also known as Ob-Rb) predominates in the hypothalamus and cerebellum (A. Savioz et al., (1997) *Neuroreport* 8: 3123; J. G. Mercer et al., (1996) *FEBS Letters* 387: 113). Ob-R(L) has also been detected at low concentrations in peripheral tissues (Y. Wang et al., (1997) *J. Biol. Chem.* 272: 16216), such as the brain (A. Heritier et al., (1997) *Neurosci. Res. Commun.* 21: 113), spleen, testes, kidney, liver, lung, adrenal (N. Hoggard et al., (1997) *Biochem. Biophys. Res. Commun.* 232: 383), and hematopoietic tissues (A. A. Mikhail et al., (1997) *Blood* 89: 1507). Ob-R(L) has also been observed in the placenta, fetal cartilage/bone, and hair follicles, and therefore is believed to play a role in development (N. Hoggard et al., (1997) *Proc. Nat'l Acad. Sci. USA* 94: 11073).

Ob-R(L) has been demonstrated to transduce intracellular signaling in a manner analogous to that observed for interleukin (IL)-6 type-cytokine receptors. Ob-R(L) transmits its information via the Janus kinases (JAK), specifically Jak2 (N. Ghilardi et al., (1997) *Mol. Endocrinol.* 11: 393), which subsequently phosphorylate transcription factors of the STAT3 family (J. Girard (1997)).

Leptin sensitizing compounds have also been discloses. See, for example, PCT Application No. 98/02159.

3. Angiogenesis

"Angiogenesis" refers to the growth of new blood vessels, or "neovascularization," and involves the growth of new blood vessels of relatively small caliber composed of endothelial cells. Angiogenesis is an integral part of many important biological processes including cancer cell proliferation solid tumor formation, inflammation, wound healing, repair of injured ischemic tissue, myocardial revascularization and remodeling, ovarian follicle maturation, menstrual cycle, and fetal development. New blood vessel formation is required for the development of any new tissue, whether normal or pathological, and thus represents a potential control point in regulating many disease states, as well as a therapeutic opportunity to encourage growth of normal tissue and "normal" angiogenesis.

The complete process for angiogenesis is not entirely understood, but it is known to involve the endothelial cells of the capillaries in the following ways:

(1) The attachment between the endothelial cells and the surrounding extracellular matrix (ECM) is altered, presumably mediated by proteases and glycosidases, which permit the destruction of the basement membrane surrounding the microvascular endothelial cells, thus allowing the endothelial cells to extend cytoplasmic buds in the direction of chemotacetic factors;

(2) There is a "chemotacetic process" of migration of the endothelial cells toward the tissue to be vascularized; and (3) There is a "mitogenesis process" (e.g., proliferation of the endothelial cells to provide additional cells for new vessels).

Each of these angiogenic activities can be measured independently utilizing in vitro endothelial cell cultures.

A number of factors are known to stimulate angiogenesis. Many of these are peptide factors, and the most notable of these are the fibroblast growth factors (FGF), both acidic (aFGF) and basic (bFGF), which can be isolated from a variety of tissues including brain, pituitary and cartilage. FGFs are characterized by their heparin-binding properties. Heparin is a powerful anticoagulant agent normally found in minute amounts in the circulatory system. Other factors known to show angiogenic-stimulating activity, include but are not limited to: vascular endothelium growth factor (VEGF), angiopoietin I and II, prostaglandins E1 and E2 (B. M. Spiegelman et al., 1992), ceruloplasmin, monocyte derived monocytoangiotropin, placental angiogenic factor, glioma-derived endothelial cell growth factor, and a heparin-binding growth factor from adenocarcinoma of the kidney that is immunologically related to bFGF (R. B. Whitman et al., (1995) U.S. Pat. No. 5,470,831). Platelet-derived endothelial cell growth factor (PD-ECGF) does not stimulate proliferation of fibroblasts in contrast to the FGFs, but has demonstrated in vitro angiogenic activity (see C—H. Heldin et al., (1993) U.S. Pat. No. 5,227,302).

Factors are also known that are capable of inhibiting endothelial cell growth in vitro. One of the most extensively studied inhibitors of endothelial cell growth is protamine, which is found only in sperm. Platelet factor 4 (PF4) and major basic protein also have been demonstrated to have inhibitory effects on angiogenesis (T. Maione, (1992) U.S. Pat. No. 5,112,946). Oncostatin A, which is similar to native PF4, has also been implicated as effecting the growth of tumors and therefore may act as an angiogenesis inhibitor (T. Maione, 1992). Antibodies have also been created possessing anti-angiogenic activity (see for example, C. R. Parish (1997) U.S. Pat. No. 5,677,181). Gene therapy has also been contemplated as a means of promoting or inhibiting angiogenesis (T. J. Wickhane et al., (1996) *J. Virol.* 70: 6831).

4. Wound Healing and Repair of Tissue After Ischemic Injury

Wounds are internal or external bodily injuries or lesions caused by physical means, such as mechanical, chemical, bacterial, or thermal means, which disrupt the normal continuity of structures. Such bodily injuries include contusions, wounds in which the skin is unbroken, incisions, wounds in which the skin is broken by a cutting instrument, and lacerations, wounds in which the skin is broken by a dull or blunt instrument. Wounds may be caused by accidents or by surgical procedures.

Wound healing consists of a series of processes whereby injured tissue is repaired, specialized tissue is regenerated, and new tissue is reorganized. Wound healing is usually divided into three phases: the inflammatory phase, the proliferative phase, and the remodeling phase. Fibronectin has been reported to be involved in each stage of the wound healing process, particularly by creating a scaffold to which the invading cells can adhere. Initially, many mediators, such as fibronectin and fibrinogen, are released to the wound site. Thereafter, angiogenesis and re-epithelialization take place (A. Beauliu (1997) U.S. Pat. No. 5,641,483). Repair of injured tissue due to ischemia is a form of wound healing which requires extensive remodeling and re-vascularization. An infarct is, by definition, and area of tissue ischemic necrosis caused by occlusion of local blood circulation. The resulting necrotic lesion leaves the affected tissue deprived of oxygen and nutrients. In the heart, obstruction of coronary circulation in particular, results in myocardial infarction. As the ischemic myocardium undergoes rapid oxygen starvation, the hypoxic microenvironment of the infected cardiac muscle induces the synthesis of angiogenic factors to attempt re-vascularization. For example vascular endothelium growth factor (VEGF) is known to be produced in the areas of the myocardium that have undergone an infarction (Ref). Similarly, ischemic injured tissue outside the heart also produce various angiogenic factors.

Adult Wound Healing

Adult wound healing in response to injury results in restoration of tissue continuity (Adzick N. S. et al. (eds), in FETAL WOUND HEALING, Elsevier, New York 1992, Chapters 13, 12, 13 and references cited therein). While some amphibians heal by regeneration, adult mammalian tissue repair involves a complex series of biochemical events that ultimately ends in scar formation. The events occurring during wound repair resemble the process of development, including synthesis, degradation and re-synthesis of the ECM (Smith L. T. et al., (1982) *J. Invest. Dermatol.* 79: 935; Blanck C. E. et al., (1987) *J. Cell. Biol.* 105: 139(A)). The ECM contains several macromolecules, including collagen, fibronectin, fibrin, proteoglycans, and elastin. When the injury involves the dermis, repair also entails the removal of cellular debris, and the laying down of a new ECM over which epidermal continuity can be reestablished. This process of repair and dermal matrix reorganization is manifested as scar formation and maturation.

Growth Factors and Wound Healing

Manipulation of the wound healing environment by the application of extrinsic growth factors such as fibroblast growth factor (FGF) and transforming growth factors (TGFβ) (T. A. Mustoe et al., (1987) *Science* 237: 1333; S. M. Seyedin et al, (1986) *J. Biol. Chem.* 261: 5693) can influence the early stages of scar formation. During tissue repair, TGFβ modulates the inflammatory response as a potent chemoattractant for fibroblasts, macrophages, neutrophils and T lymphocytes. TGFβ can also upregulate cell surface expression of the integrins that act as receptors for fibronectin, collagen, laminin, and vitronectin thereby influencing cell adhesion and migration. TGFβ enhances the epithelial covering of exposed dermis and increases tensile strength in incision wounds. See J. W. Siebert et al., (1997) U.S. Pat. No. 5,591,716) for additional discussion of growth factors that are involved in the process of wound healing and scarring.

SUMMARY OF THE INVENTION

Leptin and its associated receptor previously have not been associated with angiogenesis, repair of ischemic tissue or wound healing. Moreover, before the present invention, the leptin receptor has never previously been reported as expressed in vascular cells such as endothelial cells and vascular smooth muscle cells. This invention relates to a novel method of modulating angiogenesis, repair of ischemic tissue and wound healing using leptin and leptin receptors, which have been demonstrated to play a role in angiogenesis and wound healing. Isolation of agents that modulate leptin or the leptin receptor can be utilized in methods to treat diseases or conditions that are mediated by angiogenesis and/or wound healing in subjects such as humans. Leptin or its analogs or its specific inhibitors or other agents that modulate the leptin receptor or agents that may induce leptin or leptin receptor synthesis can be administered to the subject in an amount effective to produce an angiogenic response.

Other reagents contemplated for use in modulating angiogenesis include leptin homologues, angiogenic peptide fragments of leptin, idiotypic antibodies that bind to the leptin binding site on the leptin receptor, leptin sensitizers, and an angiogenesis-inducing compound released by a tumor.

Another aspect of the invention relates to the use of one or more agents that regulate angiogenesis in combination with compounds which modulate leptin activity, leptin receptor activity and/or leptin receptor ligand activity. The other agents to be used in combination include VEGF, FGF, PDGF, TGF-β, angiopoietin, TNF and leptin sensitizers.

The invention also discloses a method of identifying agents that modulate the angiogenic activity of the leptin receptor in vascular cells. This method comprises the steps of (1) providing an agent that binds to the leptin receptor or fragment thereof; (2) contacting endothelial cells with the agent; and (3) determining whether the agent induced a morphological change in the endothelial cells consistent with an angiogenic or anti-angiogenic effect. Another method contemplated comprises the steps of (1) contacting vascular cells with the agent; (2) determining whether the agent modulates leptin receptor mRNA expression; and (3) determining whether the agent induces a morphological change in the vascular cells consistent with an angiogenic or anti-angiogenic effect.

Too much or too little angiogenesis may be undesired depending on the disease or condition involved. As a result methods of treating undesired angiogenesis in a subject are also contemplated. Preferred method comprises the step of administering to the subject an effective amount of an agent that modulates leptin expression or leptin receptor activity sufficient to modulate the undesired angiogenesis.

Another aspect of this invention relates to antibodies that bind to the leptin receptor, wherein the binding of the antibody to the receptor modulates leptin receptor-mediated response by the cell to an angiogenesis-inducing stimulus.

This invention also discloses methods of regulating wound healing and repair of ischemic tissue, which are conditions mediated by angiogenesis. One aspect of the invention includes compositions such as a wound dressing comprising at least leptin and a suitable carrier. Other wound healing compositions contemplated include a topical composition comprising at least one agent that modulates a response in a subject to an angiogenesis-inducing stimulus, comprising an effective amount of an agent that modulates leptin or leptin receptor mediated angiogenic response to that stimulus, together with a pharmaceutically acceptable carrier. The preferred leptin receptor contemplated is the long form, however other isoforms of the leptin receptor are also considered.

Methods for treating or modulating wound healing in vertebrates, such as humans, utilizing pharmaceutical compositions are also discussed. One method for promoting the formation, maintenance or repair of tissue, which comprises the step of administering, to a subject in need thereof, an effective amount of an agent that induces a leptin or leptin receptor-mediated angiogenic response in the subject. This response can affect vascular cells such as endothelial cells or vascular smooth muscle cells. Preferred administration of agents is local, although systemic administration is also contemplated. These agents can be used in combination with other angiogenic agents such as VEGF, FGF, PDGF and leptin sensitizers. One preferred example would be the administration of leptin and VEGF to enhance wound healing. Other agents to be used in combination with leptin include TGF-β, angiopoietin, and TNF.

Preferred pharmaceutical compositions disclosed for the treatment of skin wounds are based on a pharmaceutical composition comprising at least one agent that modulates leptin or leptin receptor activities and/or their synthesis or degradation. In use, such compositions may be applied directly, and are preferably applied first to a dressing material and then the impregnated dressing material is applied to wounded or traumatized skin. The dressing material may also include at least one additive selected from the group comprising: keratolytics, surfactants, counterirritants, humectants, antiseptics, lubricants, astringents, emulsifiers, wetting agents, wound healing agents, adhesion/coating protectants, vasoconstrictors, antichlolinergics, corticosteroids, anesthetics and anti-inflammatory agents.

BRIEF DESCRIPTION OF THE DRAWING FIGURES

Figure 1B:
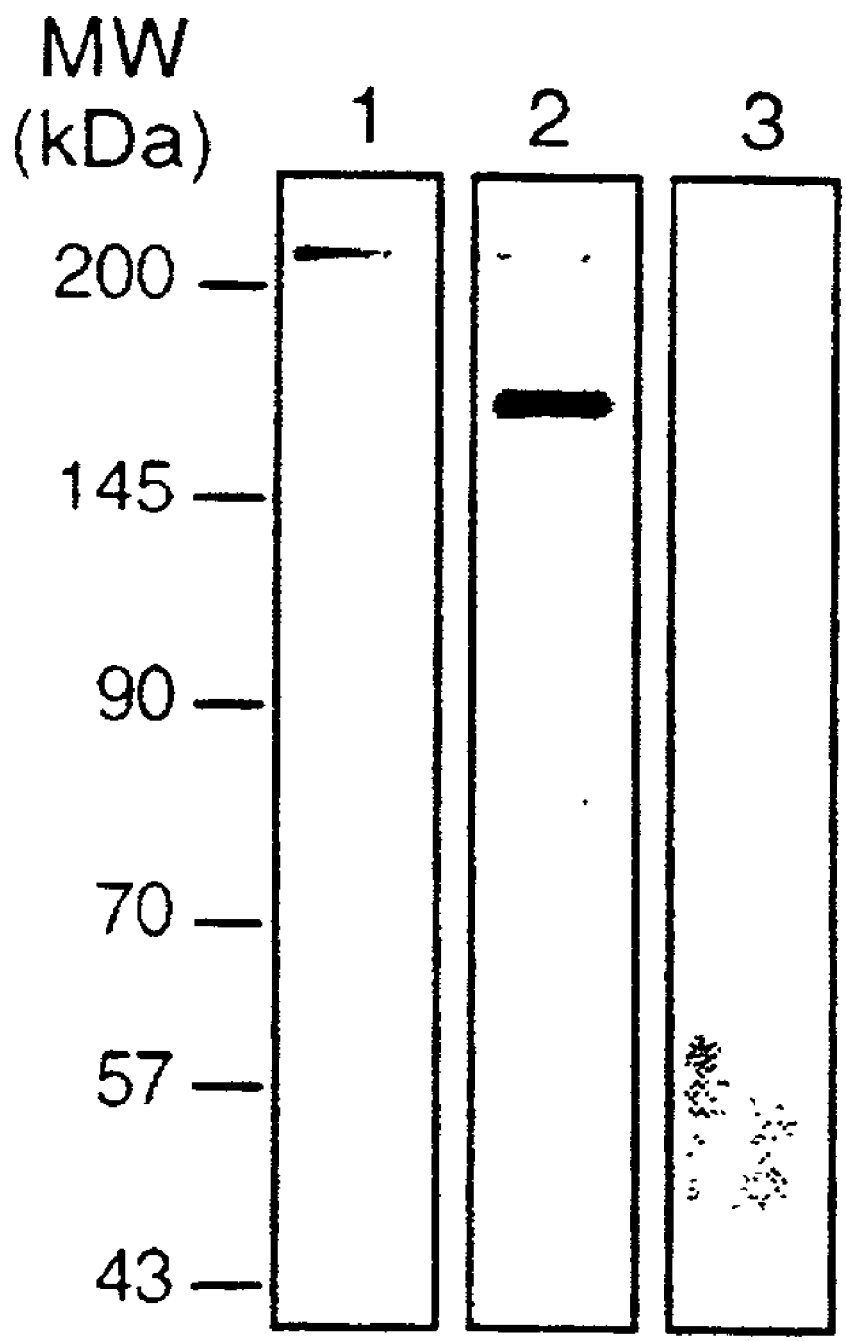
Figure 1D:
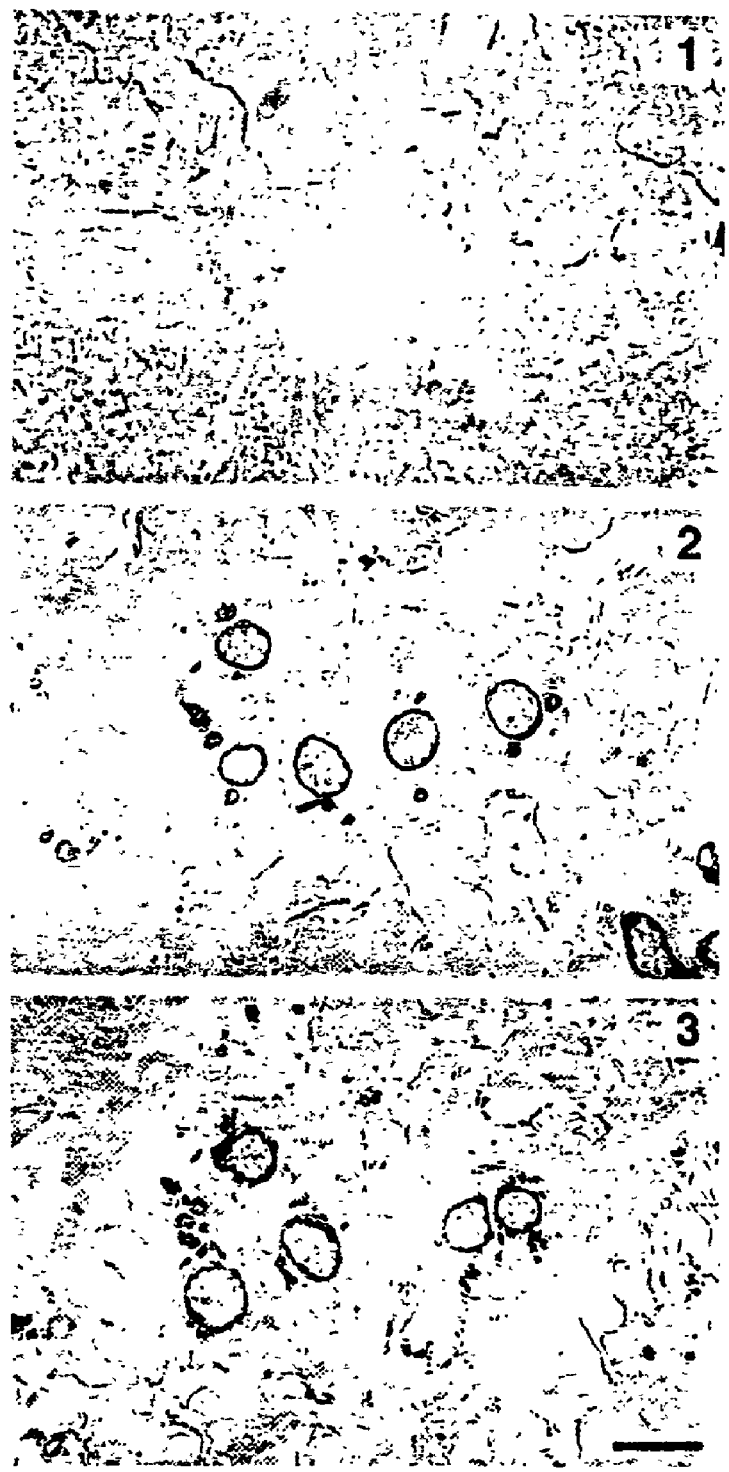

FIG. 1. Expression of Leptin Receptor in Endothelial Cells. FIG. 1A shows confocal immunofluorescence microscopy of human umbilical vein endothelial cells HUVECs that were previously permeabilized (panels 1, 2 and 4), or not (panel 3), by a brief treatment with 0.1% Triton X-100. FIG. 1B is an immunoblot of total HUVEC cell lysates with αOB-$R_{int}$ IgG (lane 1), αOB-$R_{ext}$ IgG (lane 2), or normal rabbit IgG (lane 3). FIG. 1C shows the results of RT-PCR analysis of mRNA prepared from HUVEC or HeLa cells using the PCR sense/antisense primer combinations indicated. FIG. 1D is a histochemical analysis of frozen sections from normal human dermis immunostained with normal rabbit IgG (panel 1), anti-von Willebrand factor IgG (panel 2), or anti-IC-1 antibodies against residues 1148-1156 from the carboxy terminus of human OB-Rb (panel 3).

Figure 2A:
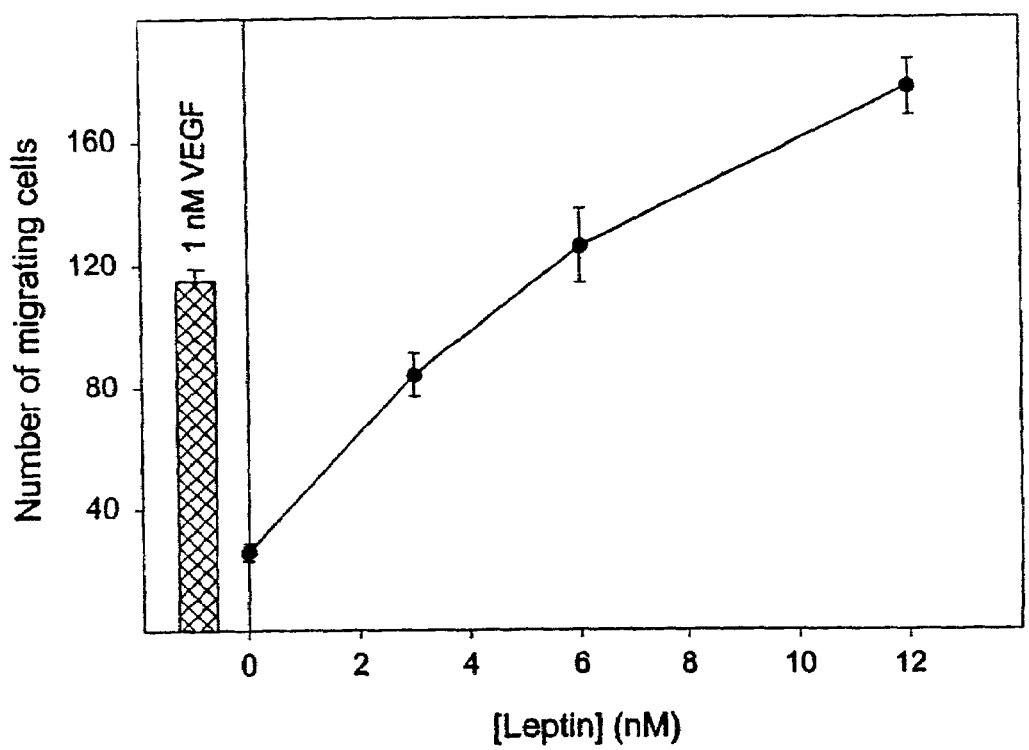
Figure 2B:
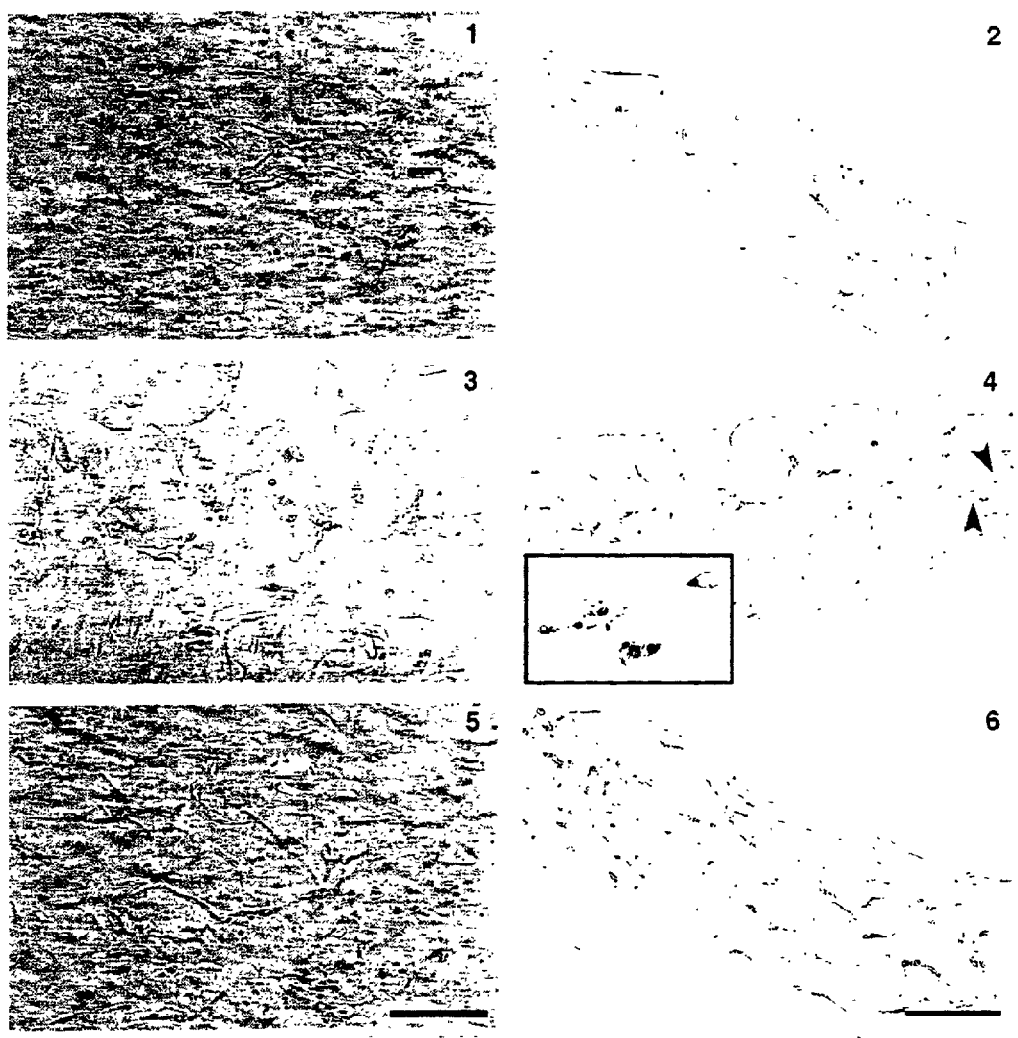

FIG. 2. Angiogenic Affect of Leptin In Vitro. FIG. 2A shows chemotaxis of bovine lung microvascular endothelial cells BLMVEC as determined by the number of cells migrating across a porous membrane in a 48-well Boyden chamber in response to increasing concentrations of human recombinant leptin. For comparison, the directional chemotacetic effect elicited by 1 nM VEGF is also shown (crosshatched bar). FIG. 2B depicts tubule formation in Type I collagen gel cultures of BLMVEC after 6 days of treatment with no leptin (panels 1 and 2), 0.5 nM leptin (panels 3 and 4), and 5 nM leptin (panels 5 and 6). Panels, 1, 3 and 5 are Varel contrast microscope images of the collagen gel cultures, whereas panels 2, 4 and 6 represent the corresponding histological sections of the formalin-fixed gels after staining with hematoxilin and eosin (H&E). Note the appearance of a tubular network in the cultures treated with leptin. The inset in panel 4 represents a magnified view (6300×) of the region indicated by the arrows showing the existence of tubular structures with a lumen. Scale bar is 200 μm.

FIG. 3. In Vivo Angiogenic Activity of Leptin. FIG. 3A shows corneal response 7 days after implanting a Hydron pellet containing PBS. Note the quiescent appearance of the limbus and absence of new vessels. FIG. 3B shows corneal response 7 days after implanting a Hydron pellet containing 10 ng of human recombinant leptin. Only occasional vessels can be seen extending from the limbus toward the implant (not visible). FIG. 3C shows vigorous neovascular response 7 days after implanting a Hydron pellet containing 50 ng of leptin.

Figure 4:
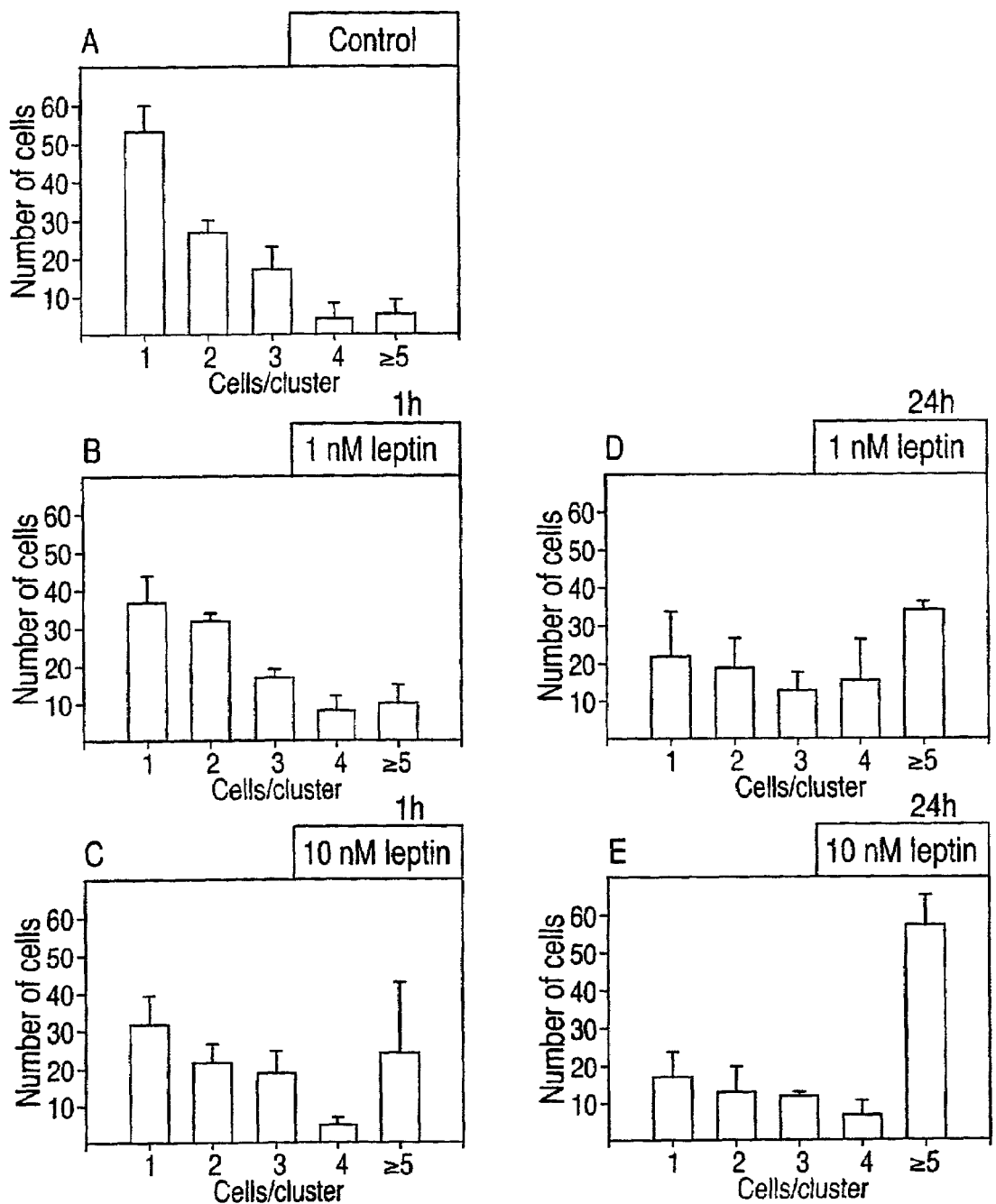

FIG. 4. Leptin Induced Cell Cluster Formation. The graphs show the ability of leptin to induce cluster formation after 1 hour (FIGS. 4B and C) and after 24 hours (FIGS. 4D and E). No leptin (Control as depicted in FIG. 4A), 1 nM of leptin (FIGS. 4B and D) and 10 nM of leptin (FIGS. 4C and E) was administered to the cells.

FIG. 5. Stained Cells of Leptin Induced and Uninduced Cells. FIG. 5A shows HUVEC non-treated control cells which display normal morphology. Staining of nuclei with DAPI (blue), and cell surface with TRITC-labeled *ulex europeous* lectin (red).

Figure 5A:
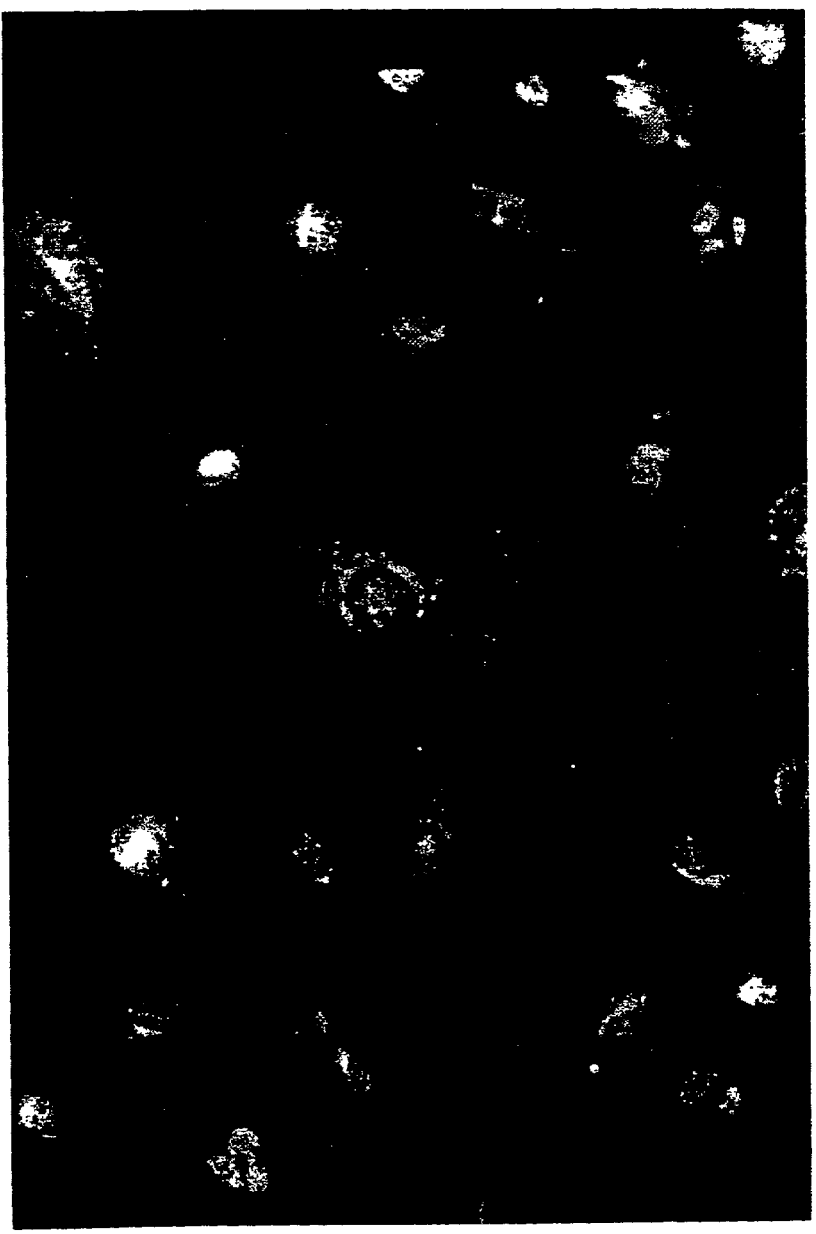
Figure 5B:

FIG. 5B are HUVEC cells treated with 10 nM human recombinant leptin for 24 hours. Cells become elongated and arrange into cord-like structures and closed circles. Double exposure photograph. Staining of nuclei with DAPI (blue), and cell surface with TRITC-labeled *ulex europeous* lectin (red).

Figure 5C:

FIG. 5C shows HUVEC treated for 24 hours with 10 nM human recombinant leptin. Cells become elongated and arrange into cord-like structures and closed circles. Double exposure photograph. Staining of the nuclei was accomplished using DAPI (blue) and of the cell surface using *ulex europeous* lectin (red).

Figure 5D:
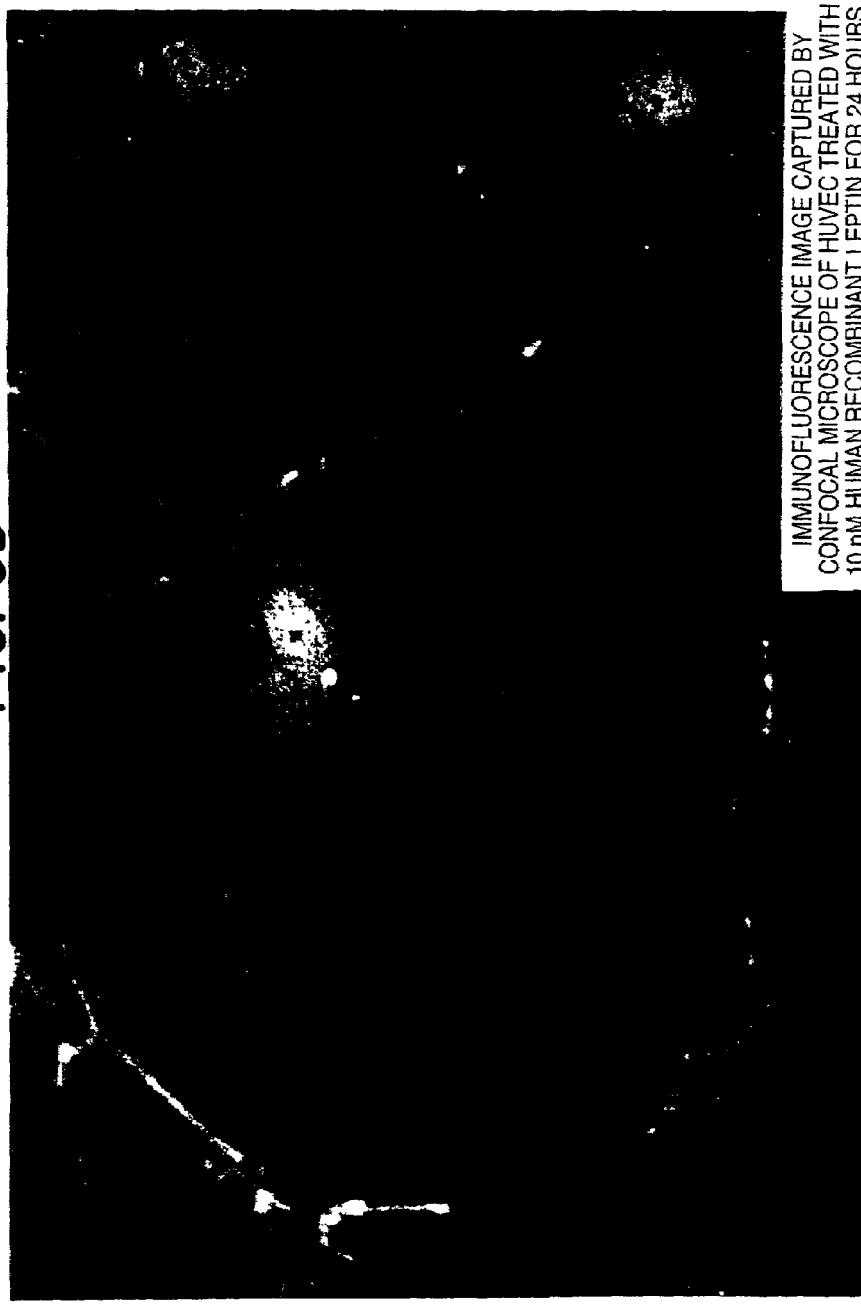

FIG. 5D depicts HUVEC treated with 10 nM human recombinant leptin for 24 hours. Cells become elongated and arrange into cord-like structures and closed circles. Double exposure photograph. Staining was described in the previous photographs.

Figure 5E:
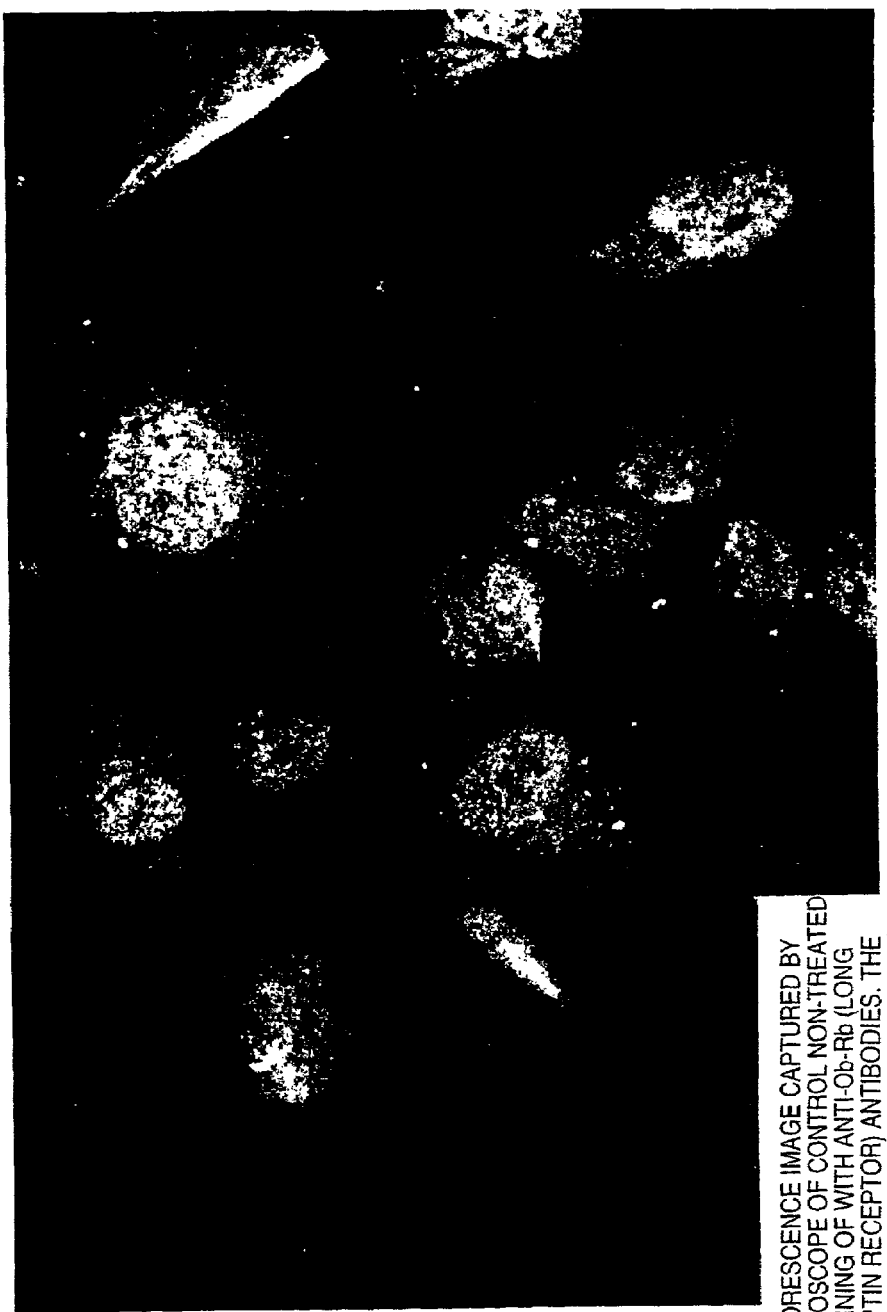

In FIG. 5E, the immunofluorescence image was captured by a confocal microscope of HUVEC treated with 10 nM human recombinant leptin for 24 hours. Cells were stained with anti-OB-Rb (long form of leptin receptor) antibodies. The intracellular distribution of the receptor appears in large clusters or vesicles.

FIG. 6. VEGF and Leptin Synergistically Enhance Angiogenesis.

Figure 6A:
Figure 6B:
Figure 6C:
Figure 6D:
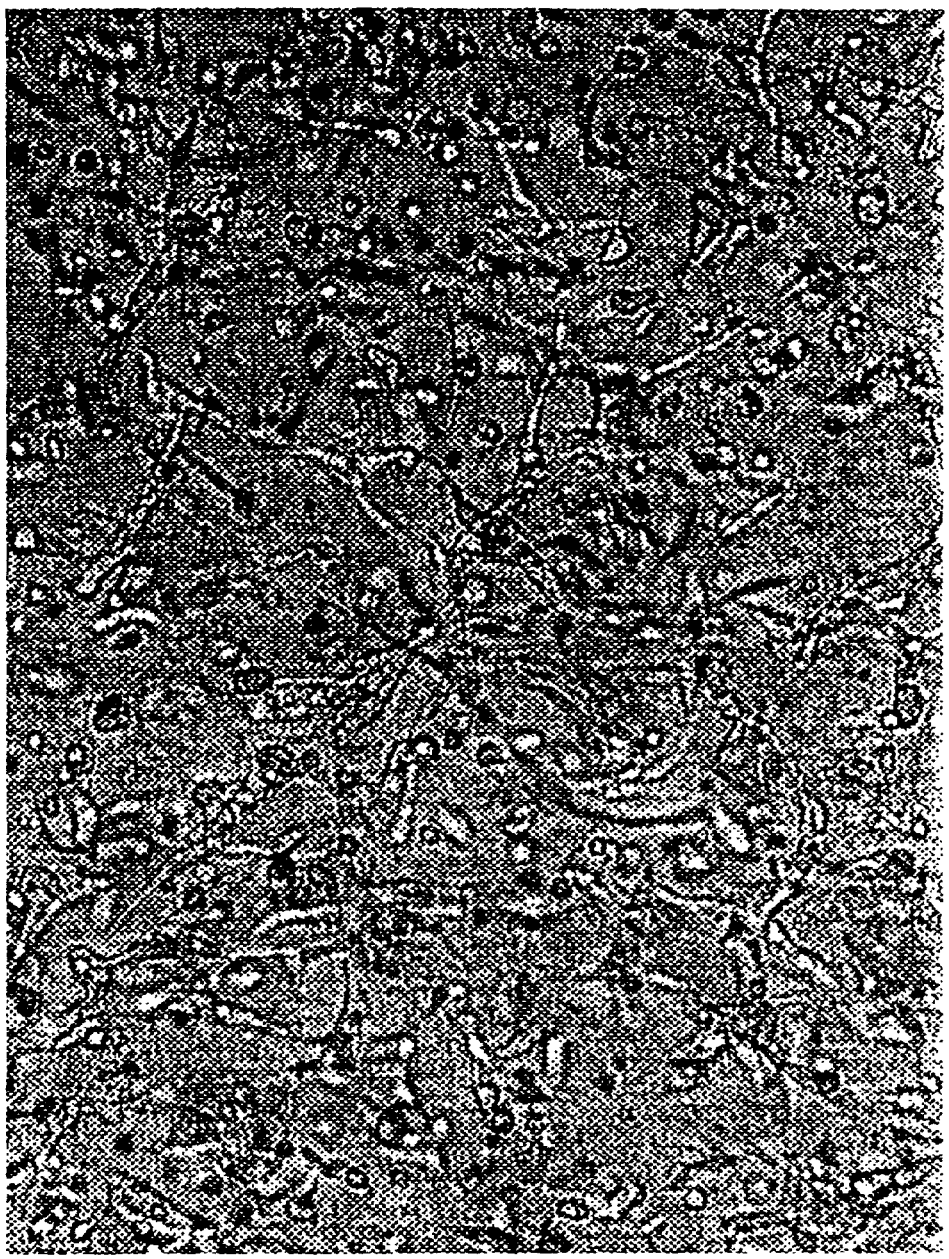

FIG. 6A shows control cells. FIG. 6B shows cells in the presence of 2 nM leptin. FIG. 6C shows the effect of 4 nM leptin on cells. FIG. 6D shows the synergistic effect of leptin and VEGF.

Figure 7:
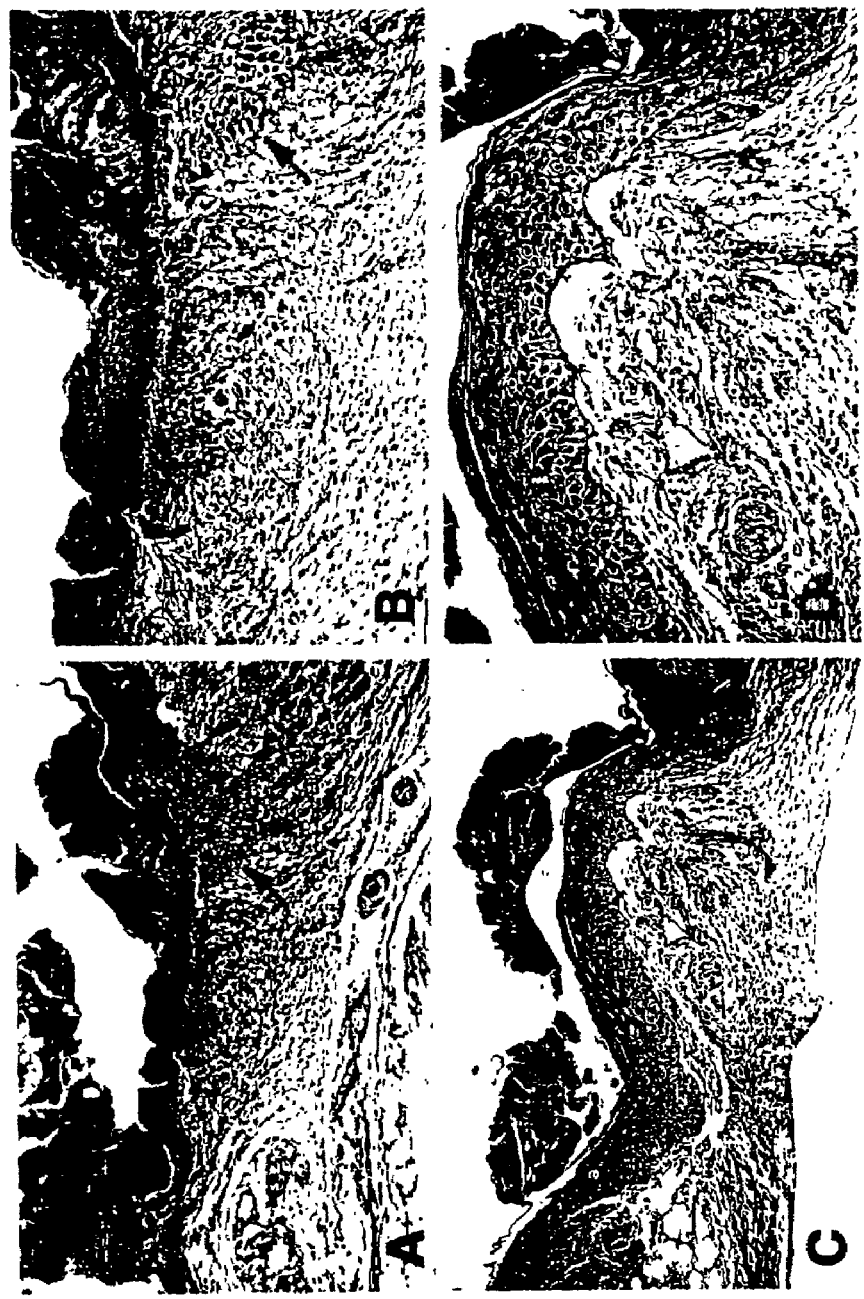

FIG. 7. Leptin Enhanced Wound Healing in SCID-beige mice. This figure shows the histology results of scalpel induced wounds in SCID-beige mice. FIGS. 7A and B are samples of stained tissue from the leptin untreated wound. Panels C and D are of the leptin treated wound. Panels A and C are at 40× magnification; B and D are at 200× magnification.

FIG. 8. Expression of Ob-R(L) in Human Vascular Smooth Muscle Cells. This figure shows that both HUVEC and vascular smooth muscle cells (VSMC) express the long form of the leptin receptor, Ob-R(L).

FIG. 9. Leptin Correlation with Energy Metabolism. FIGS. 9A to 9D show HUVEC cultures under various conditions; FIG. 9E shows expression of uncoupling protein 2.

DETAILED DESCRIPTION OF THE PREFERRED EMBODIMENTS

I. Definitions

By "leptin" is meant the leptin protein, a product of the ob gene, and its allelic variants and homologues as found (or as is believed to be found) in all vertebrate species, including human, bovine, avian, etc. Leptin encoding nucleic acid molecules include allelic variants, mutants and nucleic acids that encode biologically active variants. The "biologically active variants" are those leptin variants that can induce angiogenic activity and/or enhance wound healing. Leptin nucleic acid molecules also encompass cDNAs, RNAs, recombinant RNAs and DNAs, and antisense molecules.

"Leptin receptor" is meant to include both the long form, Ob-R(L), and the short form, Ob-R(S) or Ob-Rb, as well as other leptin receptor isoforms. "Leptin receptor" also includes allelic variants and homologues as found in most or all vertebrate species, including human, bovine, avian, etc. Leptin receptor encoding nucleic acid molecules include allelic variants, mutants and nucleic acids that encode biologically active variants of the leptin receptor. The "biologically active variants" are those leptin receptor variants that are involved in the leptin-mediated induction of angiogenic activity and/or leptin mediated enhancement of wound healing. Leptin receptor nucleic acid molecules also encompass cDNAs, RNAs, recombinant RNAs and DNAs, and antisense molecules.

By "modulating" is meant the ability to regulate a biological effect or process, such as repair of ischemic tissue, wound healing and/or angiogenesis. Modulation can occur by "inhibiting", "blocking", "down-regulating" or "depressing" leptin and/or leptin receptor-mediated activity. Modulation also encompasses instances wherein leptin or leptin receptor activity is "induced", "up-regulated", "increased", "promoted", or "enhanced".

By "anti-angiogenic effect" is meant a morphological response that inhibits or blocks vascularization including neovascularization or revascularization. An "anti-angiogenic effect" is one wherein vascularization and associated morphological changes in vascular cells, such as endothelial cells and vascular smooth muscle cells, does not occur or is inhibited. The terms "angiogenic" and "angiogenesis" refer to revascularization or neovascularization of tissue. Such neovascularization can result from the process of wound healing, repair of ischemic tissue or tissue growth. An "angiogenic effect" can be one wherein vascularization occurs or morphological changes associated with angiogenesis are observed in vascular cells such as endothelial cells ("EC") and vascular smooth muscle cells.

By "polypeptide fragments" and "peptide fragments" are meant those portions of leptin and the leptin receptor capable of modulating angiogenesis and/or wound healing.

"Agonists" include those agents, compounds, compositions, etc. which when administered can up regulate (increase, promote or otherwise elevate the level of) angiogenesis and/or wound healing by promoting leptin activity, leptin receptor activity, leptin/leptin receptor interaction, or a combination thereof.

"Antagonists" include those agents, compounds, compositions, etc. which when administered cause the down regulation (inhibition, prevention, reduction, etc.) of angiogenesis, wound healing and/or repair of ischemic tissue by inhibiting leptin activity, leptin receptor activity, leptin/leptin receptor interaction, or a combination thereof.

"Peptides" and "polypeptide fragments" of leptin or of the leptin receptor include those peptide agents capable of modulating angiogenic, wound healing and/or repair of ischemic tissue activity. Such polypeptides, and derivatives or analogs thereof, as contemplated by the present invention are those that have the ability to inhibit angiogenesis, wound healing and/or repair of ischemic tissue, or to promote angiogenesis, wound healing and/or repair of ischemic tissue by affecting leptin receptor activity, leptin activity and/or leptin receptor ligand activity. These polypeptides and peptides encompass derivatives, analogs and peptidomimetics (i.e., molecules having some structural and functional characteristic in common with peptides, but that do not contain peptide bonds). One preferred embodiment includes leptin and fragments thereof that bind to the leptin receptor. Another embodiment encompassed by "leptin polypeptides" or "leptin receptor polypeptides" are fragments of these peptides comprising at least about 2, 3, 5, 10, 15, 20, 25, 30 or 50 consecutive amino acid residues.

"Isolated" DNA, RNA, peptides, polypeptides, or proteins are DNA, RNA, peptides polypeptides or proteins that are isolated or purified relative to other DNA, RNA, peptides, polypeptides, or proteins in the source material. For example, "isolated DNA" that encodes leptin (which would include cDNA) refers to DNA purified relative to DNA which encodes polypeptides other than leptin.

Disease states and other conditions involving "angiogenic activity" include, but are not limited to myocardial conditions, trauma, tumors (benign and malignant) and tumor metastases, ischemia, tissue and graft transplantation, diabetic microangiopathy, neovascularization of adipose tissue and fat metabolism, revascularization of necrotic tissue, eye conditions (e.g., retinal neovascularization), growth of new hair and ovarian follicle maturation.

Disease states and other conditions involving "wound healing" include: scarring and scar formation, ischemia, burns, myocardial injury, enhancement of vascularization in microvascular transplants, enhancement of revascularization in necrotic tissue and tissue and graft transplants. Also contemplated is enhancement of wound healing in subject with poor wound healing, as in diabetic individuals. These conditions may be mediated by modulation of leptin, leptin receptor, and leptin receptor ligands activity.

The term "vascular cells" is meant to include both "endothelial cells" (also referred to as "EC") and "smooth muscle cells" and "vascular smooth muscle cells" (also referred to as "SMC").

"Pharmaceutically acceptable" refers to molecular entities and compositions such as fillers and excipients that are physiologically tolerated and do not typically produce an allergic or toxic reaction, such as gastric upset, dizziness and the like when administered to a subject or a patient; the preferred subjects of the invention are vertebrates, mammals, and humans.

II. Methods of Preparing Compositions Comprising Leptin, the Leptin Receptor, their Polypeptides or Polypeptide Fragments One embodiment of this invention relates to leptin and leptin receptor-related methods and compositions that modulate angiogenesis, wound healing and/or repair of ischemic tissue. One example of modulating angiogenesis, repair of ischemic tissue and wound healing is the administration of leptin to a subject, either systemically or locally or both. Other agents that mediate leptin activity, leptin receptor activity, and leptin/leptin receptor interaction are also contemplated.

As used herein, "recombinant" leptin and "recombinant" leptin receptor refers to leptin and the leptin receptor produced by recombinant expression of nucleic acid molecules encoding said proteins. For example, in general terms, the production of a recombinant form of a leptin or the leptin receptor protein typically involves the following steps. Similar steps can be utilized for production of other forms of leptin receptor ligands.

First, a nucleic acid molecule is obtained that encodes a leptin or leptin receptor protein or polypeptide fragment thereof. The leptin or leptin receptor encoding nucleic acid molecule is then preferably placed in operable linkage with suitable control sequences to form an expression unit containing the leptin or the leptin receptor encoding sequences. The expression unit is used to transform a suitable host, and the transformed host is cultured under conditions that allow the production of the desired protein or polypeptide fragments thereof. Optionally, the leptin and the leptin receptor proteins may be isolated from the medium or from the cells and further purified; recovery and purification of the protein may not be necessary in some instances where some impurities may be tolerated. Methods for preparation and synthesis of these nucleic acid molecules and proteins can be performed as described in Sambrook et al. (1989) and Ausubel et al., CURRENT PROTOCOLS IN MOLECULAR BIOLOGY (Greene Publish Co., NY, 1995). A skilled artisan can readily adapt any host/expression system known in the art for use with leptin or leptin receptor encoding sequences to produce leptin or leptin receptor proteins or polypeptide fragments thereof.

The present inventor contemplates using leptin and other agents that modulate the leptin receptor as a means of modulating angiogenesis, wound healing and/or repair of ischemic tissue. Correspondingly, agents contemplated include leptin, the leptin receptor, other leptin receptor ligands, allelic variants of leptin and the leptin receptor, and corresponding proteins in which conservative amino acid substitutions have been made such as fusion proteins. Examples of such leptin and leptin receptor nucleic acid molecules and corresponding protein sequences are disclosed as follows: GenBank Accession Nos. U58861 (*Mus musculus*), D49653 (*Rattus norvegicus* leptin), U52966 and U60151 (*Rattus norvegicus* Ob-Rb), U43168 (human Ob-R), U59894 (*Sus scrofa* leptin), AF039461 (*Mus musculus* leptin receptor isoform Rb) and U50365 (*Bos taurus* leptin). Other leptin and leptin receptor sequences are readily determinable and available to the skilled artisan.

As used herein, an "allelic variant" refers to a naturally occurring leptin or leptin receptor having a different amino acid sequence than those sequences listed above that specifically recited above. The allelic variants of leptin or the leptin receptor, though possessing a slightly different amino acid sequence, such as a conservative amino acid substitution, than those recited above, will still have the requisite biological activity to modulate angiogenesis, wound healing and/or repair of ischemic tissue. As used herein, a "conservative amino acid substitution" refers to alterations in the amino acid sequence of either leptin or the leptin receptor which do not adversely effect their ability to modulate angiogenesis, wound healing and/or repair of ischemic tissue. A substitution is said to adversely affect leptin or leptin receptor when the altered sequence decreases the capacity of leptin or the leptin receptor to modulate angiogenesis, wound healing and/or repair of ischemic tissue. Allelic variants, conservative substitution variants and related proteins utilized herein preferably will have an amino acid sequence having at least about 75% amino acid sequence identity with the published leptin or leptin receptor sequences disclosed above, more preferably at least about 80%, even more preferably at least about 90%, and most preferably at least about 95%.

Thus, the peptides, variants and related molecules that are the subject of or utilized in this invention include molecules having the sequences disclosed; fragments thereof having a consecutive sequence of at least about 3, 5, 10, 15, 20, 25, 30, 50 or more amino acid residues from the corresponding leptin or the leptin receptor and amino acid sequence variants of the disclosed leptin or the leptin receptor sequences, or their fragments as defined above, that have been conservatively substituted by another residues.

Leptin or leptin receptor proteins or polypeptide fragments thereof also can be expressed in cells or in hosts by transfecting the cells or hosts with viral vectors capable of expressing said proteins. The viral vectors contemplated include adenoviral. (See for example D. Armentano et al., (1998) U.S. Pat. No. 5,707,618 and T. J. Wickham et al., (1998) U.S. Pat. No. 5,731,190), retroviral (V. K. Pathak et al., (1998) U.S. Pat. No. 5,714,353; E. F. Vanin et al., (1998) U.S. Pat. No. 5,710,037; D. A. Williams et al., (1997) U.S. Pat. No. 5,686,278; and A. D. Miller et al., (1993) U.S. Pat. No. 5,219,740), and attenuated herpes simplex virus vectors (see for example R. L. Martuza et al., (1998) U.S. Pat. No. 5,728,379). Alternatively, non-viral vectors, such as liposomes (see for example L. Li et al., (1997) U.S. Pat. No. 5,641,508), or episomal based vectors (M. J. Cooper (1997) U.S. Pat. No. 5,624,820) or transfected eukaryotic cells such as fibroblasts or bone marrow-derived stromal cells can provide a different method of introducing leptin or the leptin receptor encoding DNAs in vivo into host cells.

According to the present invention, polypeptide fragments, peptides, peptide mimetics, derivatives, and analogs of leptin, the leptin receptor, and other leptin receptor ligands are contemplated for use in modulating angiogenic, wound healing activity and/or repair of ischemic tissue These compounds can be obtained from a variety of sources. Although the examples discussed below discuss the interaction between leptin and the leptin receptor as a means of enhancing angiogenesis, repair of ischemic tissue and wound healing, other agents which modulate angiogenesis, wound healing, and/or repair of ischemic tissue are contemplated in the present invention. The leptin/leptin receptor example can also be applied to other leptin receptor-ligands which are involved in angiogenesis, wound healing and/or repair of ischemic tissue and are expressly contemplated by the present invention.

In yet another embodiment, leptin or leptin receptor or fragments thereof can be prepared using chemical peptide synthesis. Techniques for chemical synthesis are well known in the art. For example, see Fields et al., (1990) *Int. J. Pept. Protein. Res.* 35: 161; and Stewart (1984) SOLID PHASE SYNTHESIS (2nd ed., Pierce Chemical Col, Rockford, Ill.). The preferred fragments of leptin or the leptin receptor to be utilized have about at least 3, 5, 7, 10, 15, 20, 25, 30, 35, 40, 45, 50 or more consecutive amino acids.

III. Assays Identifying Agents that Modulate Leptin or Leptin Receptor

The present invention provides methods for identifying agents that modulate the synthesis, degradation and activity of leptin and/or the leptin receptor. By regulating the activity of leptin and/or the leptin receptor, angiogenesis, repair of ischemic tissue and wound healing may be modulated. Modulation can proceed by regulating leptin, the leptin receptor, the leptin/leptin receptor interaction, other leptin receptor-ligand interactions, or the signaling cascade that follows activation of the leptin receptor by leptin or other receptor agonists. In particular, the present invention contemplates modulating the activities of leptin and other agents on the leptin receptor shown by the present invention to be expressed on vascular cells, such as endothelial cells and smooth muscle cells. The examples provided below are merely representative examples, and other agents or protein-protein combinations can be substituted.

1. Agents Contemplated

This invention relates to agents (or compounds) that modulate (regulate, inhibit or promote) angiogenesis, wound healing and/or repair of ischemic tissue by modulating (1) leptin activity, leptin synthesis and leptin degradation, (2) leptin receptor activity, synthesis and degradation, (3) leptin/leptin receptor interactions, and/or (4) the interaction of the leptin receptor with other ligands. By modulating leptin and/or leptin receptor activity, angiogenesis, wound healing and/or repair of ischemic tissue can also be modulated.

As used herein, an agent is said to modulate angiogenesis, wound healing and/or repair of ischemic tissue when it enhances or inhibits one of the four activities recited immediately above. Agents contemplated include agonists and antagonists of the long form of the leptin receptor.

The agents being screened as agonists or antagonists can be randomly selected or rationally selected or designed. As used herein, an agent is said to be randomly selected when the agent is chosen randomly without considering the specific protein domains or sequences involved in the modulation of leptin or leptin receptor-mediated angiogenesis, wound healing and/or repair of ischemic tissue. An example of randomly selected agents is the use a chemical library or a peptide combinatorial library, or a growth broth of an organism.

As used herein, an agent (reagent, compound, composition, etc.) is said to be rationally selected or designed when the agent is chosen on a non-random basis which rationally selected or designed when the agent is chosen on a non-random basis which takes into account the sequence of the target site and/or its conformation in connection with the agent's action. As described above, the agents contemplated include those that modulate (1) leptin activity, its synthesis or degradation, (2) leptin receptor activity, synthesis or degradation, (3) leptin/leptin receptor interaction, or (4) other leptin receptor ligands. Also contemplated are agents that alter leptin or the leptin receptor conformationally, thereby changing the protein such that it cannot bind with its ligand-partner. Agents can be, for example, rationally selected or rationally designed by utilizing the peptide sequences that make up the contact sites of the leptin-leptin receptor complex. Additional agents that modulate the interaction of the leptin receptor with ligand partners other than leptin can be screened in a similar manner.

The agents of the present invention can be, as examples, peptides, small molecules, vitamin derivatives, as well as carbohydrates. A skilled artisan can readily recognize that there is no limit as to the structural nature of the agents of the present invention. One preferred class of agents of the present invention are peptide agents whose amino acid sequences are chosen based on the amino acid sequence of either leptin or the leptin receptor.

One preferred embodiment contemplates agents that can bind to the domains on leptin and the leptin receptor, polypeptide fragments thereof (e.g., at least 3 consecutive amino acid residues or more of leptin or the leptin receptor, peptides thereof, peptide mimetics, antibodies (e.g., polyclonal antibodies, monoclonal antibodies, human antibodies, humanized antibodies, chimeric antibodies), antibody fragments, derivatives or analogs capable of modulating angiogenesis, wound healing and/or repair of ischemic tissue. Such agents can be obtained from any source, e.g., by purification from natural sources, using recombinant DNA technology or by chemical synthesis.

The peptide agents of the invention can be prepared using standard solid phase (or solution phase) peptide synthesis methods, as is known in the art. In addition, the DNAs encoding these peptides may be synthesized using commercially available oligonucleotide synthesis instrumentation and produced recombinantly using standard recombinant production systems. Solid phase peptide synthesis may be appropriate, if non-gene-encoded amino acids are involved.

2. Assays Used

One method of identifying agents that modulate angiogenesis, wound healing and/or repair of ischemic tissue is as follows. Leptin is mixed with the leptin receptor, particularly the leptin receptor obtained from or derived from leptin receptor expressing endothelial cells or smooth muscle cells, particularly human endothelial cells and smooth muscle cells, in the presence and absence of an agent to be tested. This assay can also be done using intact live cells as the source of the leptin receptor. After mixing under conditions that allow association of leptin and the leptin receptor, the two mixtures are analyzed and compared to determine if the agent modulated (e.g., enhanced or inhibited) the association of leptin with the leptin receptor. An agent that blocks or reduces the association of leptin with the leptin receptor will be identified by its ability to decrease the amount complexed leptin with the leptin receptor present in the sample containing the tested agent.

These assays also can be performed by attaching leptin or leptin receptor proteins or polypeptide fragments thereof which contain the leptin-binding domain or the leptin receptor binding domain to a solid substrate (e.g., a column or ELISA plate). The putative binding agent is then brought in contact with the protein or polypeptide fragments bound to the solid substrate. After washing away free compounds, it can then be determined whether the binding agent bound to the proteins (e.g., leptin or leptin receptor or polypeptide fragments thereof), which are linked to the solid surface.

Once agents are isolated which can bind to leptin, the leptin receptor, leptin receptor ligands, or polypeptide fragments thereof, these agents can then be analyzed using known in vitro systems to determine whether the agent can modulate angiogenesis, wound healing or repair of ischemic tissue. Identification of agents capable of inhibiting angiogenesis, wound healing and/or repair of ischemic tissue can be made using assays utilizing in vitro endothelial cell cultures as described in B. M. Spiegelman et al., (1992) U.S. Pat. No. 5,137,734). The assay can also be modified to use smooth muscle cells. The overall angiogenic regulation of a test substance can be measured in vivo in model systems such as the chick chorioallantoic system (which measures angiogenic activity in an embryonic system), in the rabbit corneal pocket assay, and the hamster cheek pouch assay (which measures angiogenic activity in more mature systems), also as described in B. M. Spiegelman et al., (1992). Preferably, assays using human endothelial cells or smooth muscle cells are utilized.

Additional methods of assaying chemical libraries that modulate the angiogenic activity of leptin and/or the leptin receptor can be performed in vitro by assaying enhancement or inhibition of endothelial cell cluster formation, as described further in Example 4 or general angiogenic activity as described in the in vitro assay of Example 2.

3. Drug Screening

Leptin and the leptin receptor or fragments thereof, oligopeptides, polypeptides, mimetics, and other chemical compounds can be used for screening in any of a variety of drug screening techniques. The fragment employed in such a test may be free in solution, affixed to a solid support, borne on a cell surface, or located intracellularly. The modulation of leptin synthesis and degradation activity, leptin receptor activity, and leptin/leptin receptor interaction resulting from the presence of the candidate agent may then be measured. Modulation of leptin or leptin receptor activity can result from interactions with an agent that induce changes in stability, maturation, integrity or secretion of leptin or the leptin receptor.

Another technique of drug screening which provides for high-throughput drug screening of compounds having suitable binding affinity to leptin or the leptin receptor is described in detail in "Determination of Amino Acid Sequence Antigenicity," by H. N. Geysen, PCT Appl. 84/03564 (1984). In summary, large numbers of different small peptide test compounds are synthesized on a solid substrate, such as plastic pins or some other surface substrate. The peptide test compounds are reacted with fragments of leptin or the leptin receptor and washed. Bound leptin or the leptin receptor are then detected by methods well known in the art. Purified leptin or Leptin receptor can also be coated directly onto plates for use in the aforementioned drug screening techniques. Alternatively, non-neutralizing antibodies can be used to capture the peptide and immobilize it on a solid support (see P. R. Hawkins et al., (1998) U.S. Pat. No. 5,712,115).

Another method of screening contemplated may involve labeling leptin or the leptin receptor polypeptides with any of a myriad of suitable markers, including radiolabels (e.g., $^{125}$I or $^{32}$P), various fluorescent labels and enzymes (e.g., glutathione-5-transferase, luciferase, and β-galactosidase). If desired for basic binding assays, the target polypeptide (leptin or the leptin receptor) may be immobilized by standard techniques. For example, but not for limitation, such immobilization may be effected by linkage to a solid support, such as a chromatographic matrix, or by binding to a charged surface, such as a nylon membrane.

Binding assays generally take one of two forms: immobilized leptin or the leptin receptor polypeptides can be used to bind the leptin receptor or leptin polypeptides, respectively. In each case, the labeled polypeptide is contacted with the immobilized polypeptide under aqueous conditions that permit specific binding of the polypeptide(s) to form a leptin/leptin receptor complex in the absence of added agent. Particular aqueous conditions may be selected by the practitioner according to conventional methods. For general guidance, the following buffered aqueous conditions may be used: 10-250 mM NaCl, 5-50 mM Tris-HCl (pH=5-8), with optional addition of divalent cations and/or metal chelators and/or non-ionic detergents and/or membrane fractions. It will be appreciated by those skilled in the art that additions, deletions, modifications (such as pH), and substitutions (such as KCl substituting for NaCl or buffer substitution) may be made to these basic conditions. Modifications can be made to the basic binding reaction conditions, so long as specific binding of leptin or leptin receptor polypeptides to the leptin receptor or leptin polypeptides occurs in the control reactions. Conditions that do not permit specific binding in control reactions (no agent included) are not suitable for use in performing the assays.

Preferably at least one polypeptide species is labeled with a detectable marker. Suitable labeling includes, but is not limited to radiolabeling by incorporation of a radiolabeled amino acid (e.g., $^{14}$C-Leucine, $^{3}$H-Glycine, $^{35}$S-methionine), radiolabeling by post-translational radioiodination with $^{125}$I or $^{131}$I (e.g., Bolton-Hunter reaction and chloramine T), labeling by post-translational phosphorylation with $^{32}$P (e.g., phosphorylase and inorganic radiolabeled phosphate), or labeling by other conventional methods known in the art. In embodiments where one of the polypeptide species is immobilized by linkage to a substrate, the other polypeptide is generally labeled with a detectable marker. For yeast two hybrid screening methods, refer to J. R. Bischoff et al., (1998) U.S. Pat. No. 5,705,342 and S. Fields et al., (1994) U.S. Pat. No. 5,283,173.

This invention also contemplates the use of competitive drug screening assays in which neutralizing antibodies capable of binding the leptin receptor or leptin specifically compete with a test compound for binding with leptin or the leptin receptor such that the leptin/leptin receptor complex cannot form. In this manner, the antibodies can be used to detect the presence of any peptide sharing one or more antigenic determinants with leptin and the leptin receptor.

Drug screening can also be performed using vascular cells such as endothelial cells or vascular smooth muscle cells. Both of these cell lines express large quantities of leptin receptor making them extremely beneficial for studying methods of modulating leptin and the leptin receptor. One preferred method for screening regulatory agents utilizes STAT3, as JAK/STAT interacts with the leptin receptor. A reporter system using STAT3 can be prepared utilizing the specific binding site in STAT3, called cAPRE (the nucleic acid sequence is TTCCCGAA). The constructs are prepared such that the sequence is a multimerized minimal STAT3 binding cite (TTCCCGAA) inserted upstream from a minimal promoter, such as tyrosine kinase (tk) (refer to J. Turkson et al., 1998 *Mol. Cell. Biol.* 18: 2545-52 for greater detail). Reporter genes are then placed in include, but are not limited to, luciferase, green fluorescent proteins (GFP), β-galactosidase, etc. A related method of drug screening utilizes promoter driven toxigenes. In these models, toxins such as ricin or diphtheria toxins are driven via the promoter induced by the given hormonal (e.g., leptin) stimulus. Therefore, cell ablation (cell death) can be induced when the cell receives the hormonal signal (see these articles for method details on ablation style reporting systems, P. L. Herrera et al., 1994 *Proc. Nat'l Acad. Sci. USA* 91: 12999-13003; A. Negro et al., 1996 *Eur. J. Biochem.* 241: 507-15). Cell death would be the equivalent of luciferase detection of Other methods are known and available in the art.

IV. Antibodies to Leptin, Leptin Receptors, Polypeptide Fragments Thereof

Another embodiment of this invention relates to creating antibodies and antibody fragments that modulate leptin and/or leptin receptor activity and the interaction between leptin and the leptin receptor.

An "epitope" refers generally to a specific recognition feature of a molecule, which depends on the topological orientation of functional groups of the molecule. According to the invention, a molecule contains an epitope, or shares an epitope of a second molecule, if the first molecule specifically binds or interacts competitively with the specific binding of the second molecule. There is no requirement that shared epitopes be chemically identical; however, shared epitopes must be topologically similar (i.e., have a topological arrangement of chemical functional groups that is similar in each molecule), in order to interact competitively with a target molecule. In another of its embodiments, the present invention relates to antibodies that target or bind to one or to more than one epitope on either leptin or the leptin receptor.

By "antibody" is meant a polyclonal or monoclonal antibody which is capable of binding to leptin, the leptin receptor, or a leptin receptor ligand and modulating thereby their angiogenic, wound healing and/or repair of ischemic tissue activity. Such antibodies can recognize three dimensional regions of these proteins or may be anti-peptide peptides. The term "antibody" therefore encompasses monoclonal and polyclonal antibodies and fragments thereof (e.g., Fv, scFv, Fab, Fab', or F(ab')$_2$ fragments). The antibodies contemplated also include different isotypes and isotype subclasses (e.g., IgG$_1$, IgG$_2$, IgM, to name a few). These antibodies can be prepared by raising them in vertebrates, in hybridoma cell lines or other cell lines, or by recombinant means. Also contemplated are chimeric, human, and humanized antibodies and fragments thereof, which will be less immunogenic in the subject in which they are administered (e.g., a human or humanized antibody administered to a human subject). For references on how to prepare these antibodies, see D. Lane, ANTIBODIES: A LABORATORY MANUAL (Cold Spring Harbor Press, Cold Spring Harbor N.Y., 1988); Kohler and Milstein, (1976) *Eur. J. Immunol.* 6: 511; Queen et al. U.S. Pat. No. 5,585,089; and Riechmann et al., *Nature* 332: 323 (1988).

Sequences comprising domains on leptin, the leptin receptor or leptin receptor ligands which are immunogenic for purposes of creating antibodies can be determined using such algorithms as described by Hopp and Woods, *Proc. Nat'l Acad. Sci. USA* 78: 3824 (1981); and Garnier et al., *J. Mol. Bio.* 120: 97 (1978). Additional algorithms would be known to the skilled artisan and can be used to identify peptides suitable for anti-peptide antibody production.

V. Combination Therapy

Use of leptin and/or leptin receptor proteins, the nucleic acid molecules encoding them or agents that modulate their expression in combination with other angiogenic or anti-angiogenic factors is also contemplated. The agents to be administered in combination with leptin or other agents that modulate leptin or leptin receptor activity include, but are not limited to, those agents described in: N. Catsimpoolas et al., (1988) U.S. Pat. No. 4,778,787; D'Amato (1998), G. S. Schultz et al., (1991) *Eye* 5: 170; B. M. Spiegelman et al., (1992) U.S. Pat. No. 5,137,734 (angiogenic monoglycerides); T. Maione (1992) U.S. Pat. No. 5,112,946; C-H. Heldin et al., (1993) U.S. Pat. No. 5,227,302; R. B. Whitman et al., (1995) U.S. Pat. No. 5,470,831; Parish (1997); H. App et al., (1998); P. Bohlen et al., (1997) U.S. Pat. No. 5,641, 743; Maione et al., (1992); and D. H. Carney et al., (1996) U.S. Pat. No. 5,500,412.

Agents of the present invention that modulate the activity of leptin and/or leptin receptor can be provided alone, or in combination with other agents that modulate a particular biological or pathological process. For example, leptin can be administered in combination with VEGF (or PDGF and FGFs, TNFa, IL-1 IL-11 or IL-6) to enhance angiogenesis. The examples of combination therapy provided below are specific to regulation of leptin and/or leptin receptor activity. Other combination therapies involving leptin and leptin receptor ligands are also contemplated in the present invention. The therapies described by enhanced angiogenesis spurred by leptin being only one example.

As used herein, two agents are said to be administered in combination when the two agents are administered simultaneously or are administered independently in a fashion such that the agents will act at the same time. Other embodiments include the administration of two or more agents that regulate leptin receptor activity, leptin activity, or both. One illustration includes combinations of agents wherein two or more leptin or leptin receptor antagonists or two or more agonists are administered to a subject.

Typical dosages of an effective leptin or leptin receptor agonists or antagonists can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal models, as previously described.

VI. Methods of Treating Diseases and Conditions

By utilizing reagents that modulate leptin and/or the leptin receptor, diseases and/or conditions mediated by angiogenesis, or conditions associated with repair of ischemic tissue or wound healing can be regulated. This section describes the diseases wherein reagents can be administered to a subject to enhance or inhibit angiogenesis, wound healing and/or repair of ischemic tissue. The subjects contemplated include all vertebrate species. The more preferred embodiments are the methods of treating diseases in mammals, and the most preferred method is the treatment of humans. The control of angiogenesis, wound healing and/or repair of ischemic tissue can alter the pathological damage associated with the disease or with abnormal angiogenesis. "Abnormal angiogenesis" can be an irregular or abnormal level of neovascularization (e.g., enhanced or depressed neovascularization).

1. Diseases Wherein Angiogenesis Should be Inhibited

Angiogenesis should be inhibited in diseases or conditions in which it is desirable to block or inhibit neovascularization. In a broad view, the conditions and diseases where angiogenesis desirably may be inhibited include: scar formation, tumor metastasis and tumor growth, and tissue adhesions. More specifically, these conditions and diseases include ocular neovascular diseases (e.g., including diabetic retinopathy, diabetic microangiopathy, retinal neovascularization, retinopathy of prematurity, corneal graft rejection, neovascular glaucoma, and retrolental fibroplasia), other diseases associated with corneal neovascularization (e.g., include: epidemic keratoconjunctivitis, vitamin A deficiency, contact lens overwear, atopic keratitis, superior limbic keratitis, pterygium keratitis sicca, sjogrens, acne rosacea, phylectenulosis, syphilis, *Mycobacteria* infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, marginal keratolysis, rheumatoid arthritis, systemic lupus, polyarteritis, trauma, Wegeners sarcoidosis, Scleritis, Steven's Johnson disease, periphigoid radial keratotomy and corneal graft rejection), diseases associated with retinal/choroidal neovascularization (e.g., diabetic retinopathy, macular degeneration, sickle cell anemia, sarcoid syphilis, pseudoxanthoma elasticum, Pagets disease, vein occlusion, artery occlusion, carotid obstructive disease, chronic uveitis/vritritis, mycobacterial infections, Lyme's disease, systemic lupus erythematosis, retinopathy of prematurity, Eales disease, Bechets disease, Bests disease, myopia, optic pits, Stargarts disease, pars planitis, chronic retinal detachment, hyperviscosity syndromes, toxoplasmosis, trauma and post-laser complications), diseases associated with rubeosis (neovascularization of the angle), regulation of neovascularization or active angiogenesis in adipose tissue, and diseases caused by the abnormal proliferation of fibrovascular or fibrous tissue including all forms of proliferative vitreoretinopathy.

Chronic inflammation may also involve pathological angiogenesis. Diseases with chronic inflammatory conditions considered for treatment using the methods of the present invention include: ulcerative colitis, Crohn's disease, rheumatoid arthritis, and Bartonellosis.

Neovascularization also occurs in both benign and malignant tumors, and the vascular endothelial cells and vascular smooth muscle cells in the vicinity of a tumors, particularly those cells within the range of tumor-produced angiogenic factors, therefore correspondingly are also contemplated as preferred targets for therapy. Examples of tumor diseases that are contemplated as being appropriate for treatment by the methods of the present invention include, but are not limited to: systemic forms of hemangiomas, hemangiomatosis, Osler-Weber-Rendu diseases, hereditary hemorrhagic telangiectasia, rhabdomyosarcomas, retinoblastomas, Ewing sarcomas, neuroblastomas adenocarcinomas and osteosarcomas.

In wound healing, excessive repair or fibroplasia can have detrimental side effects on surgical procedures and may be caused or exacerbated by angiogenesis. Correspondingly, these therapies also may be utilized to inhibit undesired scar formation.

2. Methods of Treating Diseases and Conditions by Up-Regulating Angiogenesis

In other diseases, angiogenic activity may need to be enhanced to promote neovascularization and/or wound healing. Diseases and conditions contemplated for said treatment include: myocardial ischemic conditions (e.g., myocardial infarction, revascularization of necrotic tissue, for example of the myocardium after an infarction or an angioplasty, angina, heart transplants, vascular grafts, and reopening vessels to improve vascularization, perfusion, collagenization and organization of said lesions), ovarian follicle maturation (which may also require down regulation of angiogenesis), wound healing, and tissue and organ transplantations (e.g., enhancement of autologous or heterologous microvascular transplantation). Promotion of wound healing includes healing of incisions, bone repair, burn healing, post-infarction repair in myocardial injury, healing of gastric ulcers and other ulcers of the gastrointestinal tract and generally in promoting the formation, maintenance and repair of tissue. Neovascularization of grafted or transplanted tissue is also contemplated, especially in subjects suffering from vascular insufficiency, such as diabetic patients.

3. Wound Healing

The dynamic process of wound healing is a well regulated sequence of events which, under normal circumstances, results in the successful repair of injured tissues. First, a cutaneous wound that cuts through the epidermis and dermis (full thickness), is accompanied by blood vessel rupture. Rapidly, clot formation occurs providing a provisional matrix to cover the wound. The clot is a key component because it provides mechanical closure with fibrin and other matrix proteins, and it is the initial source of cytokines, growth factors and chemotacetic agents released by platelet degranulation. This cocktail initiates the process of wound healing. Next, neutrophils move into the interstitum at the site of injury in response to bacterial products and other chemotacetic agents. This is followed by macrophages that release chemical signals to attract fibroblasts. The resident and infiltrating fibroblasts secrete cytokines such as PDFG-BB and bFGF and begin to deposit a new extracellular matrix that will be an essential component of the scar tissue. Meanwhile, the process of reepithelialization begins on the borders of the wound where keratinocytes of the basal layer display new integrins to attach to a provisional matrix. The epidermal migration continues until a monolayer of keratinocytes covers the wound. Several known growth factors intervene in the reepithelialization of the skin (e.g., EGF, TGFa and KGF 1 and 2).

In the underlying dermis, the process of neovascularization is established in response to severed vessels and angiogenic factors produced locally. The role of the microvasculature in wound healing is essential for the repair to take place. After the interruption in the continuity of the microvasculature, endothelial cells need to dissolve their cell-cell attachments, migrate outside the vesssel into the extracellular matrix, undergo mitosis and finally reassociate in an orderly manner to form a network of capillaries necessary for the healing to proceed. It appears that VEGF secreted acutely by the keratinocytes is responsible in great part for the angiogenic response. Other angiogenic factors like basic fibroblast growth factor (bFGF) and transforming growth factor b (TGFb) are also present. Recently, we and others have demonstrated that leptin is angiogenic, therefore we have hypothesized that leptin is involved normal wound healing. Leptin, a protein produced in the underlying adipose tissue, may be present at relatively high concentrations because the dermal vasculature, both superficial and deep plexuses, derive from larger vessels that originate from the subcutaneous adipose layer.

The present inventor observed that leptin plays a role in normal wound healing. Leptin is present at the wound site a few hours after injury. Leptin also peaks in the circulation 12 hours after wounding. These results suggest that topical treatment with leptin accelerates the healing process. For example, by day 3, there are less infiltrating cells and granulation tissue with leptin treatment when compared to controls. These wound healing parameters represent early events in healing thus showing that leptin treatment accelerates the healing process. In addition, reepithelialization is enhanced with leptin treatment. These effects of leptin are due to local production of the cytokine at the wound site. While treatment with exogenous leptin improves wound healing, treatment with anti-leptin antibodies markedly slows the rate of healing. This evidence supports a role for leptin in wound healing.

Normal healing involves proliferation, migration, matrix synthesis and angiogenesis. An impairment at any of these complex phases will lead to complications in wound healing. In diseases of impaired neovascularization, such as diabetes, dermal wound healing is severely compromised. This often leads to nonhealing wounds and, ultimately, amputation. Recombinant protein therapy with leptin may augment angiogenesis and can be of great value in diabetes and other clinical situations where healing is impaired.

VII. Pharmaceutical Compounds Comprising Agents According to the Present Invention that Modulate Angiogenesis In the treatment of the clinical conditions noted above, the compounds of this invention may be utilized in compositions such as tablets, capsules or elixirs for oral administration, suppositories for rectal administration, sterile solutions or suspensions for parenteral or intramuscular administration and the like.

The pharmaceutical compositions of this invention can be used in the form of a pharmaceutical preparation, for example, in solid, semi-solid or liquid form which contains one or more of the compounds of the present invention, as an active ingredient, in admixture with an organic or inorganic carrier or excipient suitable for external, enteral or parenteral applications. The active ingredient may be compounded, for example, with the usual non-toxic pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid or liquid form and in addition auxiliary, stabilizing, thickening and coloring agents and perfumes may be used. The active object compound (e.g., an agent capable of modulating leptin, the leptin receptor and/or leptin receptor ligand activity that mediates their angiogenic and/or wound healing capability is included in the pharmaceutical composition in an amount sufficient to produce the desired effect upon the process or condition (e.g., regulation of neovascularization) of the disease.

For preparing solid compositions such as tablets, the principal active ingredient is mixed with a pharmaceutical carrier (e.g., conventional tableting ingredients such as corn starch, lactose, sucrose, sorbitol, talc, stearic acid, magnesium stearate, dicalcium phosphate or gums) and other pharmaceutical diluents (e.g., water) to form a solid preformulation composition containing a substantially homogeneous mixture of a compound of the present invention, or a non-toxic pharmaceutically acceptable salt thereof. When referring to the preformulation compositions as substantially homogenous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from about 0.1 mg to about 500 mg of the active ingredient of the present invention. The tablets or pills of the novel composition can be coated or otherwise compounded to provide a dosage form affording the advantage of prolonged action. For example, the tablet or pill can comprise an inner dosage an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings such materials including a number of polymeric acids and mixtures of polymeric acids with such materials as shellac, cetyl alcohol and cellulose acetate.

The liquid forms, in which the novel composition of the present invention may be incorporated for administration orally or by injection, include aqueous solution, suitably flavored syrups, aqueous or oil suspensions, and flavored emulsions with edible oils such as cottonseed oil, sesame oil, coconut oil, or peanut oil as well as elixirs and similar pharmaceutical vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone or gelatin.

Liquid preparations for oral administration may take the form of, for example, solutions, syrups or suspensions, or they may be presented as a dry product for reconstitution with water or other suitable vehicles before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

For buccal administration, the composition may take the form of tablets or lozenges formulated in conventional manners.

For topical administration, formulations may be made up with at least one agent that modulates leptin or leptin receptor activity or the activity of a leptin receptor ligand or provides leptin, such as leptin producing cells. The active ingredient may further be combined in admixture with at least one other ingredient constituting an acceptable carrier, diluent or excipient in order to provide a composition, such as a cream, gel, solid, paste, salve, powder, lotion, liquid, aerosol treatment, or the like, which is most suitable for topical application. Sterile distilled water alone and simple cream, ointment and gel bases may be employed as carriers of the active agents. Examples of bases and suspending vehicles include Fattibase™ (acrylic polymer resin base), Polybase™ (polyethylene glycol base) by Paddock Laboratories, Inc. Additional therapeutic agents may be added to the formulations as medically indicated, selected from the classes of: keratolytics, surfactants, counter-irritants, humectants, antiseptics, lubricants, astringents, wound additional healing agents, emulsifiers, wetting agents, additional adhesion/coating protectants, additional anti-inflammatory agents, vasoconstrictors, vasodilators, anticholinergics, corticosteroids (e.g., glucocorticoids) and anesthetics. Preservatives and buffers may also be added. The formulation may be applied to a sterile dressing, biodegradable, absorbable patches or dressings for topical application, or to slow release implant systems with a high initial release decaying to slow release. When the compositions are administered to treat burns, they may be in the form of an irrigant, preferably in combination with a physiological saline solution. Compositions can also be in the form of ointments or suspensions, preferably in combination with purified collagen. The compositions may also be impregnated into transdermal patches, plasters, and bandages. For additional topical compositions contemplated for therapeutic administration, see M. W. J. Ferguson et al., (1997) U.S. Pat. No. 5,662,904; J. D. Gallina (1997) U.S. Pat. No. 5,679,655; and M. B. Sporn et al., (1998) U.S. Pat. No. 5,705,477.

The active compounds may be formulated for parenteral administration by injection, which includes using conventional catheterization techniques or infusion. Formulations for injection may be presented in unit dosage form, e.g., in ampules, or in multi-dose containers, with an added preservative. The compositions may take such forms as suspensions, solutions or emulsions in oily or aqueous vehicles, and may contain formulating agents such as suspending, stabilizing, and/or dispersing agents. Alternatively, the active ingredients may be in powder form for reconstitution with a suitable vehicle, e.g., sterile pyrogen-free water, before use.

VIII. Modulation of Endothelial Cells to Regulate Lipid Metabolism

Leptin, the product of the ob gene, is a 15 kDa polypeptide hormone. Produced and secreted largely by adipocytes, leptin primarily regulates adiposity through effects on food intake and energy expenditure via receptors expressed in central and peripheral targets (L. A. Tartaglia et al., 1995 *Cell* 83: 1263-71; and J. S. Flier, 1998 *Proc. Nat'l Acad. Sci. USA* 94: 4242-5). Recently, leptin has been reported to directly cause depletion of stored triacylglycerol (TG) in peripheral tissues by a mechanism that seems to involve decreased TG synthesis and increased TG oxidation within cells (U. Sarmiento et al., 1997 *Lab. Invest.* 77: 243-56). Such action of leptin includes apparent effects upon the activity of acetyl CoA carboxylase, the rate limiting enzyme in fatty acid (FA) synthesis, and increased rates of FA oxidation (Y. Bai et al., 1996 *J. Biol. Chem.* 271: 13939-42). This is to be distinguished from the lipolytic response normally observed in the transition from the "fed" to the "starved" state. During this transition, blood levels of free fatty acids (FFA) and ketones are not increased, suggesting that peripheral lipid oxidation may be occurring in response to leptin (M. Shimabukuro et al., 1997 *Proc. Nat'l Acad. Sci. USA* 94: 4637-41). Thus, leptin appears to directly influence fuel homeostasis through changes in the expression and/or activity of biochemical pathways involved in thermogenesis and lipid metabolism (Shimabukuro et al., 1997; D. M. Muoio et al., 1997 *Diabetes* 48: 1360-3; J. A. Tuominen et al., 1997 *Microcirculation* 4: 211-32).

The extensive and complex network of vascular structures pervading white adipose tissue (WAT) has led to the proposal that angiogenic factors, locally produced and secreted within this tissue play an important role in maintaining adequate blood supply (D. L. Crandall et al., 1997 *Microcirculation* 4: 211-32). Although some of the generic angiogenic factors known to act upon endothelial cells (EC) also exhibit angiogenic activity in WAT, indigenous factors have been found, but the precise factor(s) remain unidentified (D. L. Crandall et al., 1997). The present inventor here describe findings that leptin, which is produced and secreted by adipocytes, as discussed above, exhibits a potent and concentration-dependent angiogenic activity in EC, both in vivo and in vitro. Moreover, EC express the intact and functional long form of the leptin receptor (Ob-Rb(L)Ob-Rb), which is capable of tranducing a signal through the JAK/STAT pathway. (M. Roció Sierra-Honigmann et al., 1998 *Science* 281:1683-86.)

Adipose tissue increases or decreases its mass depending on the demands for storing or utilization of lipid fuels in the body. This plasticity suggests the existence of regulatory mechanisms that can maintain a delicate balance between adipocytes and EC. Furthermore, a plastic microvasculature that could assist or facilitate mobilization and oxidation of adipose tissue lipid stores for the purpose of fuel homeostasis and/or thermogenesis seems plausible. In this context, leptin production by adipocytes may signal the need for the necessary degree of vascularization which is appropriate to fulfill the demand for rapid changes in energy expenditure.

Notably, in normal animals treated with leptin, it has been documented that WAT has a marked increase in tissue microvasculature accompanied by a reduction in the size of particular fat deposits (Sarmiento et al., 1997). On the other hand, certain pre-adipocyte cell lines that differentiate in culture do not express leptin mRNA under normal culture conditions (O. A. MacDougald et al., 1995 *Proc. Nat'l Acad. Sci. USA* 92: 9034-7). However, when these same cells are implanted subcutaneously into genetically immunosuppressed mice, they acquire the ability to express leptin (S. Mandrup et al., 1997 *Proc. Nat'l Acad. Sci. USA* 94: 4300-5). This observation suggests the existence of factors or cellular interactions which are responsible for "switching on" leptin expression. Importantly, the fat pads that arise from these implanted cells in the recipient mice, are fully vascularized and indistinguishable from normal WAT. Therefore, it is plausible that a feedback mechanism may exist in which leptin expression occurs in the implanted free adipocytes to trigger vascularization and so ensure nutrient and oxygen supplies for the implanted cells. The appropriate tissue microvasculature is then established as local endothelial cells respond to leptin. Moreover, it is reasonable that if leptin induces TG depletion from WAT and the characteristic changes in circulating metabolites associated with peripheral fat utilization during extended food deprivation do not occur, a likely effector site for these metabolic effects of leptin is precisely the vascular endothelium.

In accordance with the present invention, as described above or as discussed in the Examples below, there may be employed conventional molecular biology, microbiology and recombinant DNA techniques. Such techniques are explained fully in the literature. See for example, Sambrook, Fritsch and Maniatis, MOLECULAR CLONING: A LABORATORY MANUAL (Second Ed., Cold Spring Harbor Press, Cold Spring Harbor N.Y., 1989); DNA CLONING: A PRACTICAL APPROACH, vols. 1 and 2 (D. N. Glover ed., 1985); OLIGONUCLEOTIDE SYNTHESIS (M. J. Gait ed., 1984); NUCLEIC ACID HYBRIDIZATION (B. D. Hames and S. J. Higgins eds., 1985); TRANSCRIPTION AND TRANSLATION (B. D. Hames and S. J. Higgins, eds., 1984); E. Harlow and D. Lane, ANTIBODIES: A LABORATORY MANUAL (Cold Spring Harbor Press, Cold Spring Harbor N.Y., 1988); and Ausubel et. al., CURRENT PROTOCOLS IN MOLECULAR BIOLOGY (Greene Publishing Co. NY, 1995) to name a few.

The following working examples which disclose leptin induced angiogenesis and wound healing, specifically point out preferred embodiments of the present invention. These examples are not to be construed as limiting in any way the scope of the invention. Other examples involving leptin and the leptin receptor will be apparent to one skilled in the art. Assays analogous to those described below can be utilized in examining additional leptin and/or leptin receptor mediated angiogenic and wound healing modulation.

EXAMPLES

Example 1

Expression of Leptin in Endothelial Cells

Methods. FIG. 1A depicts confocal immunofluorescence microscopy of human umbilical vein endothelial cells (HUVEC) that were previously permeabilized (panels 1, 2 and 4), or not (panel 3), by a brief treatment with 0.1% Triton X-100. Immunostaining was performed (M. R. Sierra-Honigmann et al., (1996) Lab. Invest. 74: 684) with normal rabbit IgG (panel 4), using $\alpha OB\text{-}R_{ext}$ antibodies against the extracellular region of OB-R (panels 2 and 3) and $\alpha$ and $\alpha OB\text{-}R_{int}$ antibodies against the intracellular region of OB-R (panel 1) described below. Scale bar is 5 μm.

Briefly, cells grown on fibronectin-coated multichamber Lab-Teck slides were fixed by adding 4% paraformaldehyde in PBS at a 1:1 dilution for 5 minutes at room temperature at the end of the treatment periods. Cells were washed four times with HBSS/1% fetal bovine serum (FBS) and incubated with the appropriate antibody (1:1,000 dilution) for 1 hour at room temperature, followed by four additional washes with HBSS/1% FBS. The cells were then exposed to the secondary antibody (which consisted of Texas red-conjugated goat anti-rabbit IgG) for 45 minutes in HBSS/1% FBS, washed four times in the same solution without the antibody, and given a final wash with PBS. The slides were then detached and cover slipped with Antifade® mounting solution (Molecular Probes). Cells were analyzed with a MRC600 confocal microscope (Bio-Rad).

Peptide antibodies were based on the sequence of the human leptin receptor (G. H. Lee et al., (1996) Nature 379: 632) corresponding to regions within the intracellular or the extracellular domain. These peptides were synthesized and coupled to KLH. The intracellular region peptides were (1) IC-1 for residues 1148-65 at the carboxy terminal end of the receptor (CSTQTHKIMENKMCDLTV), and (2) IC-2, for residues 1062-1078 (KLEGNFPEENNDKKSIY). The extracellular region peptides were (1) EC-1, for residues 247-263 (ITDDGNLKISWSSPPLV), (2) EC-2, for residues 473-487 (CSDIPSIHPISEPKD), and (3) EC-3 for residues 753-67 (CVIVSWILSPSDYKL). The KLH-peptide conjugates were used to generate polyclonal antibodies in rabbits, and IgG fractions prepared from bleeds with the highest ELISA titers. Unless indicated otherwise, antibodies against IC-1 and IC-2 were combined in equal amounts giving rise to $\alpha OB\text{-}R_{int}$ antibodies directed against intracellular epitopes of the OB-R. Likewise, equal amounts of antibodies against EC-1, EC-2 and EC-3 were mixed giving rise to $\alpha\text{-}OB\text{-}R_{ext}$ antibodies directed against extracellular epitopes of the OB-R.

FIG. 1B depicts the immunoblotting of total HUVEC cell lysates with $\alpha OB\text{-}R_{int}$ IgG (lane 1), $\alpha OB\text{-}R_{ext}$ IgG (lane 2), or normal rabbit IgG (lane 3). Total HUVEC cell lysates and immunoblotting were performed essentially as described (Sierra-Honigmann et al., 1996). Briefly, cells in confluent monolayers were washed with ice-cold $Ca^{2+}$- and $Mg^{2+}$-free HBSS, detached with trypsin, centrifuged and resuspended in 500 μl of lysis buffer [10 mM Tris-HCl pH 7.8, 2 mM $MgCl_2$, 1% NP-40, 1 mM Pefablock® (Boehringer), and 1 μg/ml each of leupeptin, antipain, chyostatin, pepstatin A1 and 10 μg/ml benzamidine]. After a 3 minute incubation on ice, the cell suspension was diluted with 1 volume of cold, deionized water and incubated for 2 additional min. The extract was centrifuged at 300×g for 6 min. at 4° C., and the supernate collected and saved as an NP-40 lysate. Proteins in the lysate samples were separated by SDS-PAGE (U. K. Laemmli, (1970) Nature 227:680) in 7%-15% gradient gels. Proteins were electrophoretically transferred to nitrocellulose membranes from the gels. The filters were then blocked with TBS (pH 8.0) in the presence of 0.05% Tween-20 and 5% non-fat dried milk for 1 hour at room temperature. The blot was incubated with the indicated antibodies at 1:1,000 dilution in the same solution at 4° C. overnight. After three 15 min washes, blots were incubated with a 1:2,000 dilution of affinity-purified horseradish peroxidase-conjugated donkey anti-rabbit IgG (Jackson Immunoresearch) for 1 hr at room temperature. Proteins were visualized by chemiluminescence using the SuperSignal Western Blotting System according to the manufacturer's instructions (Pierce).

For FIG. 1C, RT-PCR analysis of mRNA prepared from HUVEC or HeLa cells was performed using the PCR sense/antisense primer combinations as indicated. The relative location of these primers within the cDNAs encoding the OB-Ra (short form) and OB-Rb (long form) forms of the leptin receptor is also shown. Whereas the combination 1/2 would detect both the long and short forms of the leptin receptor, 1/3, 1/5, and 4/5 are specific for the OB-Rb long form. The predicted size of the corresponding PCR products in each case is also indicated. After PCR amplification, the resulting DNA products were analyzed by agarose gel electrophoresis where each lane corresponds to the PCR primer combination indicated at the bottom. The PCR products are shown with respect to the migration of DNA molecular weight markers (lane M).

FIG. 1D depicts the histochemical analysis of frozen sections from normal human dermis immunostained with normal rabbit IgG (panel 1), anti-von Willebrand factor IgG (panel 2), or anti-IC-1 antibodies against residues 1148-1156 from the carboxy terminus of human OB-Rb (panel 3). After incubation with primary antibodies, tissue sections were developed with secondary horseradish peroxidase-conjugated goat anti-rabbit IgG using a Vectastain® Elite ABC kit (Vector Labs). Scale bar is 50 µm.

Results. Expression of the leptin receptor was first examined in human umbilical vein endothelial cells (HUVEC) using confocal immunofluorescence microscopy and rabbit polyclonal antibodies directed against synthetic peptides based on the sequence of the human leptin receptor. When a combination of antibodies specific for epitopes present exclusively in the cytoplasmic domain of the OB-Rb form of the receptor ($\alpha$OB-R$_{int}$) was used on permeabilized cells, an abundant staining distributed throughout the cell was readily detected, which was not detected when non-immune antibodies were employed (FIG. 1A, panels 1 and 4 respectively). The pattern of this signal is characterized by a scattered, punctuate, intracellular staining suggesting that the bulk of the long form of the leptin receptor resides in an intracellular vesicular compartment. In contrast, when a mixture of antibodies directed against extracellular epitopes of the receptor was used ($\alpha$OB-R$_{ext}$), an intense staining was seen to predominate in peripheral structures with a perinuclear distribution, albeit it also exhibited punctuate features (FIG. 1A, panel 2). As expected, when non-permeabilized cells were stained with $\alpha$OB-R$_{ext}$, a diffuse staining pattern was observed, consistent with membrane localization of the leptin receptor at the cell surface (FIG. 1A, panel 3). The same pattern of immunostaining was found in endothelial cells (EC) from other sources, including microvascular and aortic bovine EC and human adipose or dermal microvascular EC.

Since the $\alpha$OB-R$_{ext}$ antibodies would recognize epitopes common to both the long (OB-Rb) and short (OB-Ra) forms of the receptor, it is likely that the immunostaining detected in this case reflects the coexpression of short receptor variants in addition to OB-Rb, which is observed when $\alpha$OB-R$_{int}$ antibodies are used exclusively (FIG. 1A, panel 1). To test this possibility directly, cellular proteins present in total extracts prepared from primary cultures of EC were first fractionated by gel electrophoresis followed by immunoblot analysis employing the antibodies described above. With $\alpha$OB-R$_{int}$ antibodies, a single band with an apparent molecular mass above 200 kDa (FIG. 1B, lane 1 was detected). The same protein species was seen when $\alpha$OB-R$_{ext}$ antibodies were used, but in this case an additional, more intense protein band exhibiting an apparent mobility at 170 kDa was also observed (FIG. 1B, lane 2). Thus, at least two leptin receptor isoforms are expressed in EC, the largest of which corresponds to the OB-Rb form, since it can be recognized by antibodies directed against epitopes present exclusively in the cytoplasmic domain of OB-Rb.

To confirm these findings, expression of OB-Rb was also examined by PCR amplification of reverse transcribed cellular RNA prepared from HUVEC, using appropriate PCR primers specific for the leptin receptor (see schematic in FIG. 1C). When RNA from HUVEC was subjected to the RT-PCR reactions in the presence of PCR primer pair combinations that would specifically detect expression of the OB-Rb transcript (pairs 1/3, 1/5 and 4/5, FIG. 1C), amplicon products of the predicted size were detected, but not when RNA from human HeLa cells was used as a control. Likewise, it is evident that one or more additional short leptin receptor forms (most likely OB-Ra) were also expressed in HUVEC, or as the only species detectable in HeLa cells (FIG. 1C).

Finally, to determine whether the leptin receptor is expressed in EC in the context of the tissue microvasculature, frozen tissue sections prepared from human skin were studied by immunohistochemical staining employing $\alpha$OB-R$_{int}$ antibodies. A strong immunostaining reaction can be demonstrated in the endothelial lining of blood vessels present in these tissue sections (FIG. 1D, panel 2). For comparison, a similar endothelial staining pattern was observed when antibodies against von Willebrand factor were used (FIG. 1D, panel 3), but not with normal, non-immune rabbit antibodies (FIG. 1D, panel 1). Taken together, these findings indicate that OB-Rb, the full-length variant of the leptin receptor regarded as the putative form competent for signaling in target tissues, is expressed in EC.

Example 2

Angiogenic Affect of Leptin In Vitro

Once it was determined that EC cells express Ob-R(L), the next step was to ascertain the role leptin played in these cells. In vitro experiments were performed examining chemotacetic directional migration across porous membranes, formation of capillary-like structures in three dimensional (3D) collagen gels and cell proliferation assays in response to leptin administration.

Methods. Bovine lung microvascular EC (BLMVEC) were plated on 6-well plates and grown in complete DMEM medium as described by G. García-Cardeña et al., (1996) *Proc. Nat'l Acad. Sci. USA* 93: 6448. The cells were grown to confluence and starved for 12 hours in complete medium without serum and supplemented with 2% BSA. Chemotaxis was assayed as described by V. Kundra et al., (1995) *J. Cell Biol.* 130: 725 using a 48-well Boyden chamber (Neuroprobe) equipped with 25×80 mm, 8 µm polyvinylpyrrolidone-free filters (Nucleopore), previously coated with 100 µg/ml collagen type I (Collaborative Research). Human recombinant leptin was diluted in DMEM/2% BSA and added to the lower wells at the indicated concentrations, while the upper wells received $1.5 \times 10^4$ cells suspended in 50 ml of the same medium. The chamber was then incubated at 37° C. in a 5% $CO_2$ humidified atmosphere for 4 hours. The migrating cells were fixed with methanol, and the filter stained with Giemsa (Fisher Scientific). The chemotacetic response was analyzed by counting the number of cells in a given microscopic field observed at 400×. All cells in 10 random fields were counted.

Three dimensional (3D) cultures of BLMVEC were established in gel matrices using rat tail Type I collagen. Collagen solutions were prepared by mixing the protein with an appropriate volume of 10×M199 culture medium and neutralizing the pH by the addition of 1N NaOH. BLMVEC were added immediately to a final concentration of 1.5-2× $10^6$ cells/ml collagen (final collagen concentration was 2 mg/ml). Props (0.1 ml each) of the cell/collagen mixture were added to Petri dishes and placed in a humidified incubator at 37° C. for 2-5 min. Growth medium, with or without human recombinant leptin, was then added to each dish. Leptin was replenished every 24 hours. BLMVEC were allowed to form tube-like structures for about 4 days, and were then fixed in buffered formalin before being embedded in paraffin and processed for microscopic observation. For phase contrast analysis, an Axiovert 25 microscope (Carl Zeiss) equipped with a Varel contrast optical system was used. Images were captured with a 3CCD camera (DAGE-MTI) and the digital images were acquired using a Scion Image software program for the Power Macintosh.

Results. Since leptin is synthesized and secreted by adipocytes, and in view of studies demonstrating the angiogenic potential of adipose tissue (K. J. Silverman et al., (1988) *Biochem. Biophys. Res. Commun.* 153: 347; D. L. Crandall et al., (1991) in OBESITY IN EUROPE 405-9 (John Libby, London)), the angiogenic capability of leptin itself was examined. FIG. 2A used a modified Boyden chamber assay. The bovine lung microvascular EC (BLMVEC) exhibited a robust directional migration response that was directly proportional to the concentration of leptin used. For comparison, the chemotacetic migratory effect elicited by a known angiogenic factor, i.e. vascular endothelial growth factor (VEGF) (N. Ferrara et al., (1989) *Biochem. Biophys. Res. Commun.* 161: 851) was tested and shown to be within the range observed for leptin stimulation (FIG. 2A). In addition, as many angiogenic factors are able to promote the formation of capillary-like tubules in 3D-collagen gels in vitro (R. K. Jain et al., (1997) *Nat. Med.* 3: 1203; and R. Auerbach et al., *Pharmacol. Ther.* 51:1), leptin was also tested in this system. As shown in FIG. 2B, culturing of 3D collagen gels containing BLMVEC in the presence of leptin led to the development of capillary-like structures. In contrast to the control (FIG. 2B, panels 1 and 2), exposure of EC to leptin gives rise to the formation of multiple elongated tubular structures that appear to bifurcate often, thereby pervading the gel matrix as an extensive interconnecting 3D network. In these experiments, the abundance and complexity of such tubular networks becomes more evident when EC are stimulated with the highest concentration of leptin (compare 0.5 nM with 5.0 nM; FIG. 2B, panels 3 and 4 compared with panels 5 and 6, respectively). Importantly, these tubules apparently represent permeable structures as judged by the existence of a lumen clearly discernable in transversal sections observed at higher magnification (FIG. 2B, panel 4, inset). Finally, it is noteworthy that proliferation assay experiments using several types of human and bovine EC (from microvascular and large vessel origin) did not show consistent or significant mitogenic activity attributable to leptin (results not shown). Therefore, as in the case of several angiogenic polypeptides (J. Folkman (1995) *N. Engl. J. Med.* 333: 1757), leptin does not appear to act as a growth factor for EC. However, it clearly does play a role in the morphogenesis of higher order, capillary like tubules that arise from EC.

Example 3

Angiogenic Affect of Leptin In Vivo

After the in vitro effects of leptin were demonstrated as shown in FIG. 2, leptin was studied in vivo to determine whether it would enhance angiogenesis.

Methods. Slow release Hydron polymer pellets containing increasing amounts of leptin were surgically implanted in the cornea of rats, and the neovascular response observed. Angiogenic activity of leptin was determined in the rat corneal micropocket assay as described in V. P. Castle et al., (1997) *Lab. Invest.* 77: 51. Concentrated solutions containing the indicated amount of test samples were combined with an equal volume of sterile Hydron casting solution (Interferon Sciences), and aliquots (5 μl) were deposited onto the surface of 1-mm Teflon rods and glued to the surface of a glass Petri dish. Pellets were dried and then surgically implanted into intracorneal pockets. Neovascularization responses were assessed 7 days after implantation following perfusion of animals with colloidal carbon and dissection of corneas. A sustained ingrowth of capillaries advancing from the limbus toward the Hydron implant was scored as a positive response.

Results. As shown in Table I, leptin caused a dose-dependent, vigorous angiogenic effect comparable to that achieved with VEGF. These observations are also illustrated in FIG. 3, in which the neovascularization effect of 10 ng and 25 ng of leptin is clearly evident compared to the negative control (FIG. 3, panels B, C, and A respectively). Taken together with the in vitro effects of Example 2, these findings demonstrate that leptin is a potent angiogenic factor that promotes the migration and organization of endothelial cells into capillary-like tubular structures. The fully functional OB-Rb long form of the leptin receptor, which is expressed in EC, is presumably responsible for mediating these effects. However, other leptin receptor isoforms may also be responsible for these effects.

TABLE I

Neovascular Responses Induced by Human Recombinant Leptin in Rat Corneas

| Test Sample | Proportion of Positive Responses (%) |
|---|---|
| Controls: | |
| Hydron alone | 0/3 (0) |
| Hydron + PBS | 0/2 (0) |
| Hydron + 25 ng VEGF | 3/3 (100) |
| Human recombinant leptin: | |
| 5 ng | 0/3 (0) |
| 10 ng | 1/4 (25)* |
| 25 ng | 5/5 (100)† |
| 50 ng | 4/4 (100)† |
| 100 ng | 3/3 (100)‡ |

*Detectable but weak positive response.
†Vigorous sustained neovascular responses.
‡Responses associated with significant corneal inflammation.

Example 4

Leptin Induced Cell Cluster Formation

Methods. Quantitative data of cell-cluster formation in response to leptin treatment was determined as follows: Cells were plated sparsely on microscope slide-culture chambers coated with fibronectin to promote cell attachment to the glass surface. The plating was done so that most of the cells were not in contact with each other (approximately $1 \times 10^5$ cells/ml). After 12 h in culture in complete media, the cells were treated with leptin and incubated for different times. At the end of the incubations, the cells were fixed for 1 min with acetone at −20° C., washed with PBS and incubated for 30 min with *ulex* europeaus lectin labeled with TRITC (red fluorochrome to stain the plasma membrane of endothelial cells). The slides were washed and mounted with coverslips in anti-fade media containing DAPI (blue fluorochrome to stain nuclei). The results were acquired as follows: a blinded subject was instructed to count 100 cells per slide. First, each field, magnified 100 times, was visualized with the filter that allowed to see only cell nuclei. Fields should have at least 5 nuclei to be counted and were chosen at random. The number of nuclei equaled the number of cells per field. After the nuclei were counted, the filter was changed so as to allow the examiner to visualize the plasma membrane of the cells (stained in red). At this point the examiner was asked to record how many of the cells, in the same field where the nuclei were counted, were single or making cell-cell contact in clusters of 2, 3, 4, and 5 or more cells.

Results. The graphs show that at 1 hour, 10 nM leptin is already inducing cluster formation of five or more groups. By 24 hr, the majority of the cells are forming groups as shown in FIG. 4 and in photos of the plated cells FIGS. 5A-E. These results further support the angiogenic activity of leptin and the presence of the leptin receptor in EC cells.

Example 5

VEGF and Leptin Act Synergistically to Enhance Angiogenesis

Methods. Human umbilical vein endothelial cells (HU-VECs) were used to study the potential synergy of VEGF and leptin. FIG. 6 shows the results of one such experiment wherein cells were treated with no leptin (FIG. 6A), 2 nM leptin (FIG. 6B), 4 nM leptin (FIG. 6C) and leptin and VEGF (FIG. 6D).

Results. A wound site becomes very highly enriched in VEGF produced by keratinocytes on days 2 to 4 after injury (L. F. Brown et al., (1992) *J. Exp. Med.* 176: 1375; B. Berse et al., (1992) *Mol. Biol. Cell.* 3: 211; H. F. Dvorak et al., (1992) *Ann. NY Acad. Sci.* 667: 101; and P. Martin (1997) *Science* 276: 76). The immediate vascular relationship between the subcutaneous adipose tissue and the dermis, therefore may allow leptin and VEGF to act in synergy to induce a potent neovascularization response, as is observed in FIG. 6D as compared to leptin alone (FIGS. 6B and C) or in the control (FIG. 6A).

Example 6

Leptin Enhanced Wound Healing as Shown In Vivo in SCID-Beige Mice

Methods. A SCID-beige mouse unsuitable for another project because of its "leak" (not immunosuppressed), was used in the experiment in FIG. 7. Two full thickness longitudinal wounds of approximately 5 mm in length were done using a sterile scalpel. Each wound was localized in the ventral sub-axillary region of the mouse. Prior to wounding, the mouse was anesthetized, shaved and the skin was wiped with a disinfectant solution. One side was injected with 3 µg of recombinant leptin in a volume of 50 µl at a 3 mm distance from each border of the wound. The contralateral wound received the same volume of sterile saline. The wounds were allowed to dry and then they were covered with microporous surgical tape. On day 3, the mouse wounds were allowed to dry. Then they were covered with microporous surgical tape. On day 3, the mouse was euthanized by cervical dislocation and skin was recovered from the wound sites including peripheral normal skin for sectioning and staining with H and E.

Results. In panel A of FIG. 7, 40× magnification of the wound that received saline is shown. Panel B shows the same field at a higher magnification (200×). There is appreciable granulation tissue present. The thickening of the epidermal borders are shown by the arrow. Also the basal lamina has not yet regenerated. In contrast, the leptin treated wound (panels C and D) show a complete re-epithelialization and basal lamina regeneration. The newly formed epithelium is still engrossed and the borders of the wound are almost imperceptible.

Example 7

Presence of Leptin in the Vitreous of Patients with Retinopathy

Data is presented that demonstrates the presence of leptin in patients suffering from diabetic retinopathy, a condition that involves neovascularization. The patients with retinopathy have leptin present in the vitreous (See patient nos. 1, 2, 4, 5 and 7). It is well documented that patients suffering from this condition have VEGF in their vitreous. This data now demonstrates that leptin is also present in the vitreous.

Methods. The samples obtained were discarded fluids from surgery. The patients had undergone vitrectomy for surgical repair of proliferative neovascularization (in the case of diabetics) or for repair of retinal detachment etc. in the case of the controls. Leptin concentration was measured using a commercially available RIA kit that uses $^{125}$I-leptin (LINCO Laboratories). The results presented are the average of duplicate samples. Although the number of samples is low, it is likely that the elevated vitreal leptin can be a very important factor in the pathogenesis of retinal neovascularization. Some patients have low concentrations but blood/vitreal ratios may be more significant than values alone. Retinal neovascularization in diabetics is the major cause of blindness in the US.

Results. As shown in Table II, patients with significant levels of leptin in their blood also had significant levels of leptin in their vitreous (see patients 1, 2, 4, 5, and 7). Patients who did not have elevated blood serum leptin levels correspondingly did not have significant concentrations of leptin in their vitreous. Additional data show that leptin concentrations are elevated in eyes with vascular and fribrotic proliferation. These data indicate that leptin participates in angiogenic and fibrotic retinal diseases.

TABLE II

| PATIENT ID | BLOOD NG/ML | VITREOUS NG/ML | AQUEOUS NG/ML |
|---|---|---|---|
| 1 | 64 | 8.5 | 1.3 |
| 2 | 128 | 14 | ND |
| 3 | 18 | 2.5 | >0.05 |
| 4 | 24 | 115 | >0.05 |
| 5 (control) | 0.8 | >0.05 | >0.05 |
| 6 | 4 | 1.5 | 0.1 |
| 7 (control) | 20 | 0.2 | >0.05 |

Normal human serum: Females (lean) = 7.4 ± 3.7; Males (lean) = 3.8 ± 1.8, wherein lean refers to the patient's total body fat being under 20%.

Example 8

Leptin Enhanced Wound Healing by First Intention

Healing by first intention means that the borders of the wounded skin are near each other, such as a wound created by a scalpel incision. Typically these wounds heal within 5-7 days. Leptin is administered to the wounded area to determine whether leptin enhances the rate of wound healing.

Methods. Wounding and administration of leptin are performed as described in Example 6. Sectioning of the skin is carried out using a cryomicrotome. The optimal thickness of the sections will be determined experimentally, but is expected to be 4-7 mm. To assess the extent of neovascularization, standard immunostaining techniques are employed using a commercially available monoclonal antibody to mouse CD31 (PECAM), as the primary antibody followed by immunoperoxidase conjugated secondary antibodies. In some experiments, discrimination between pre-existing and newly formed microvessels may be needed, in which case a monoclonal antibody against αVβ3 integrin will be used. This integrin has been shown to be expressed in the neovasculature of wounds in the dermis that are in the process of healing.

To detect the presence of VEGF and leptin, independent immunohistochemical procedures are followed using serial sections from the same tissue blocks. Because rabbit polyclonal antibodies are available against murine VEGF and murine leptin, it will be possible to use a double staining immunohistochemical approach employing standard immunoperoxidase and alkaline phosphatase methods. This will allow detection and comparison of the presence of angiogenic factors in the context of active neovascularization sites. A polyclonal antibody that recognizes and can distinguish Ob-R(L) from other isoforms can also be utilized.

Quantitation of angiogenesis is made by visual counting of the number of vessels (CD31 positive immunostaining) at low magnification (100×) in treated and control skin sections. The same slides will be utilized for computer enhanced video imaging employing analytical software (NIH Image), which compares the number of vessels based on the color of the histochemical reaction. Skin wounds processed by hematoxylin and eosin staining will be evaluated by an individual blinded to the origin of the various specimens studied.

Results. The mouse wound treated with leptin is expected to be substantially healed in 3 days time, whereas the untreated control mouse is expected to only begin to show signs of healing.

Example 9

Leptin Enhanced Wound Healing by Second Intention

Wounds of the second intention wound healing type are larger, and a piece of the skin typically has been lost. This type of wound obviously takes much longer to heal.

As a result, the effects of leptin are again examined to determine whether leptin enhanced wound healing of this type.

Methods. Animals are anesthetized under methoxyflurane until no distress response is observed in response to stimuli. Abdominal skin is shaved, and wiped with surgical disinfectant solution. Full thickness wounds are inflicted approximately 5 mm under the axillary region on each side using a 3 mm diameter punch biopsy surgical device. The skin and subcutaneous tissue is lifted by retraction at the time of wounding to avoid damage of deep tissues. Normally, these small circular wounds undergo healing by second intention, because no opposing borders of the skin are in contact.

To study the effect of local treatment with leptin, 50 ml of sterile saline solution containing 1 to 50 ng of mouse recombinant leptin is injected subcutaneously at a distance of 3 mm from the wound borders immediately after inflicting the wound. The wounds are allowed to dry in order to form a scab, and are then covered with sterile microporous surgical tape. Animals are sacrificed at 1, 3, 5, 7, and 14 days after the wounding by cervical dislocation. Finally, a small square area of approximately 36 mm$^2$ of skin containing the complete epithelial margins of the lesion is excised. This specimen is carefully divided into two equal portions, one of which is fixed in buffered formalin and then embedded in paraffin, sectioned and stained with hematoxylin and eosin (H&E). The remaining portion is frozen and used to prepare sections for immunohistochemistry. Control skin specimens from the same animals are used to provide a baseline reference for quantifying the angiogenic effect.

Comparisons may be made as are described in Example 8.

Results. Although wounds of this type generally heal more slowly than wounds healing by first intention, a noticeable difference in the extent of healing is expected between leptin treated and untreated animals at day 3 after inflicting of the wound. Table III shows specific data resulting from the topical application of leptin on experimental wounds.

TABLE III

Effect of Topical Leptin Treatment on Experimental Wounds

| | | |
|---|---|---|
| Distance Between Wound Borders (mm) | 1.34 +/− 0.18 | 0.55 +/− 0.14 |
| Relative Granulation Tissue Thickness | 2.00 +/− 0.26 | 1.20 +/− 0.13 |
| Relative Density of Extracellular Matrix | 1.50 +/− 0.22 | 21.0 +/− 0.28 |
| Relative Inflammatory Infiltrate | 2.31 +/− 0.17 | 1.46 +/− 0.18 |

Example 10

Treatment of Skin Wounds in Normal and Diabetic Mice

Methods. Using the methods of wounding described above, diabetic and normal mice responses to leptin are compared.

The results expected are enhanced healing of wounds in ob/ob mice (which lack leptin) and no observable effect in db/db mice (which lack the leptin receptor). NOD and NZO control mice may vary somewhat in their response; however, use of leptin in diabetic subjects who do not naturally produce leptin may be beneficial as a wound healing therapeutic agent.

Example 11

Expression of Leptin in Smooth Muscle Cells

Methods. The methods used for this experiment are substantially as described above. Lysates were made from primary cultures of human umbilical vein endothelial cells (HUVEC), simian epithelial cells (COS-7) and primary culture of human vascular smooth muscle cells derived from aorta (VSMC) as described. Proteins were separated on a 5% SDS-PAGE gel and transferred by electrotransference onto a nitrocellulose membrane. The nitrocellulose membrane was immunostained using rabbit polyclonal serum, anti-human Ob-R(L) and standard Western blotting procedures, as described in the examples above.

Results. The Western blot depicted in FIG. 8 shows that both the HUVEC cells and VSMC express the long form of the human Ob-R(L) in substantial quantities. The amount of leptin receptor expressed in endothelial cells and smooth muscle cells distinguishes these vascular cells from other cells which express the leptin receptor, where expression is at very low levels.

Example 12

Leptin Correlation with Energy Metabolism

Since the foregoing examples demonstrate that leptin and the leptin receptor are involved in angiogenesis, the manner in which leptin induced energy metabolism was also investigated.

Methods. Cells were treated with leptin as previously described. For FIG. 9E, PCR transcripts were analyzed using 1% agarose gels and stained with ethidium bromide.

Figure 9A:
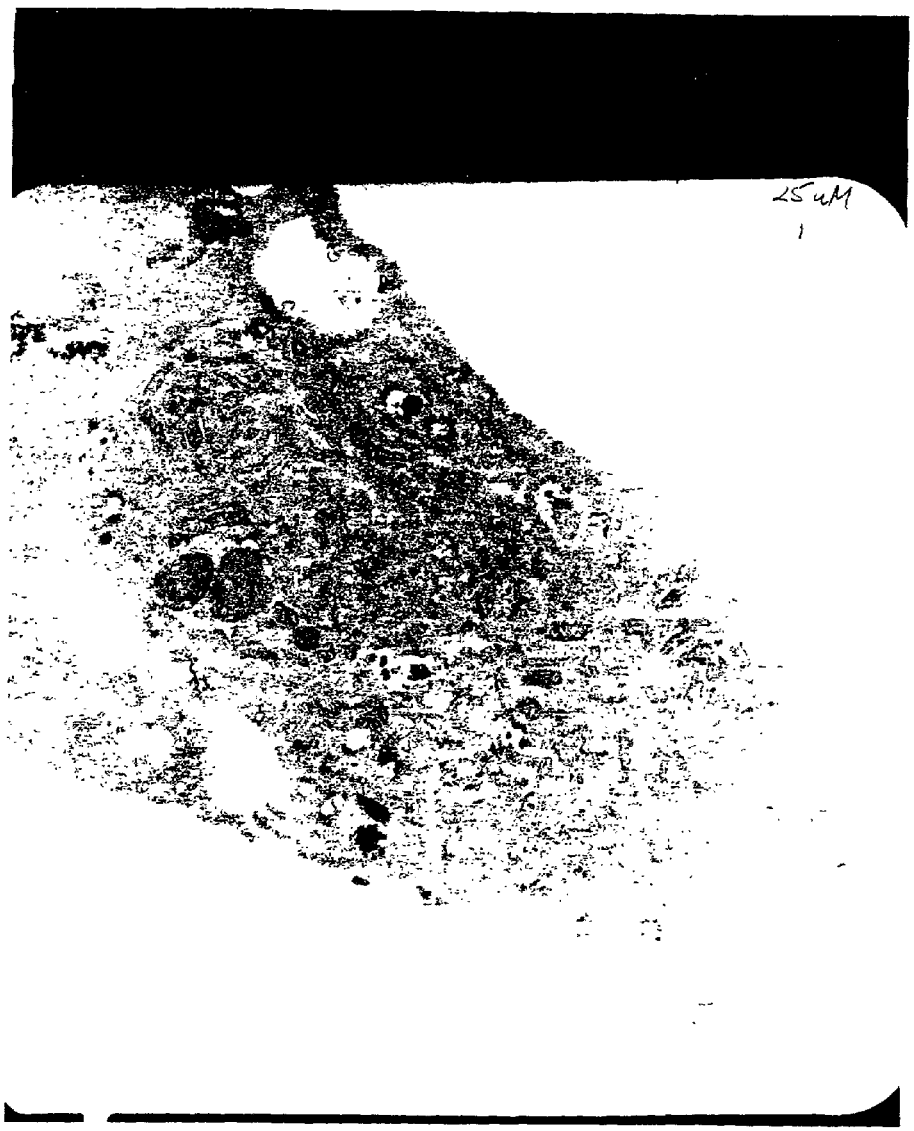
Figure 9C:
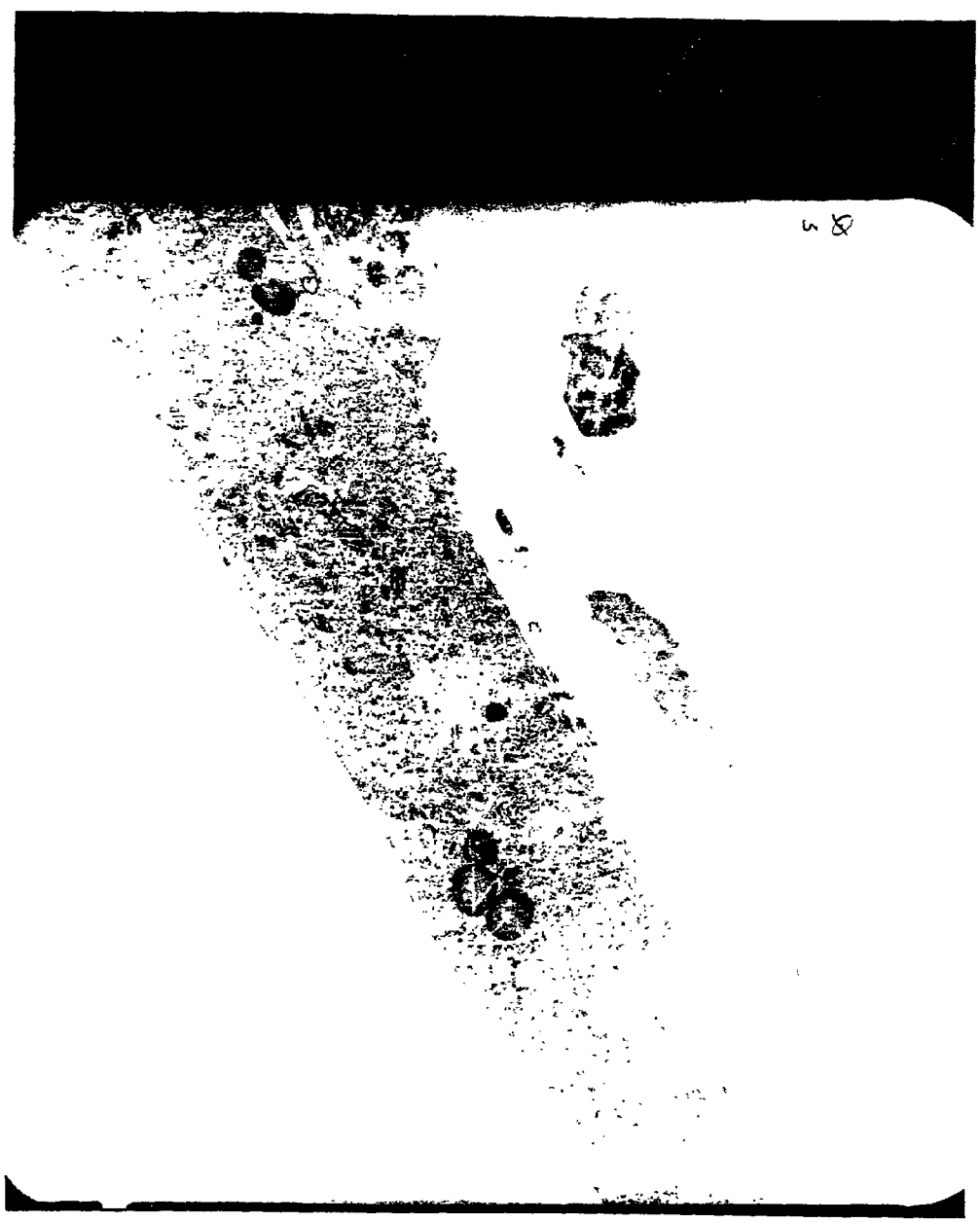
Figure 9D:

Results. FIGS. 9A-9D are images of monolayers of HUVEC primary cultures scanned using electron microscopy. The images were processed in the conventional methods for imaging with a transmission electron microscope. In FIG. 9A, HUVECs were treated for 72 hours in the presence of 25 nM human recombinant leptin. The image is at 8000× magnification. FIG. 9B is the same as FIG. 9A. The two cells are presented side by side. This image illustrates the increased number of mitochondria and rough endoplasmic reticulum (rER). In FIG. 9C, the cells are the same as above only without leptin treatment. The cells in FIG. 9C represent the negative control. In FIG. 9D, HUVEC cells were treated again with 25 nM recombinant human leptin as performed for FIG. 9A. FIG. 9D shows the very high number of mitochondria present, which is presumably due to the incubation with leptin. The very large number of mitochondria in the endothelial cells (HUVECs in this experiment) after leptin incubation may indicate that EC can oxidize free fatty acids (FFA). Leptin therefore is shown to have increased the number of mitochondria.

In addition, if an uncoupling protein is present, as described by the experiment below, then the energy generated by the bond breakage is released as heat instead of being used to form ATP. The vasculature wall, where endothelial and smooth muscle cells are found, is the perfect site for this to occur because as heat is generated, it can be readily dissipated through the blood stream (i.e., blood serves as a coolant). This theory may explain why leptin does not mobilize fat stores into the blood stream, but does significantly decrease the fat content of adipocytes. Alternatively, leptin can induce secretion of a factor or factors from the vessel walls that will then induce the fatty acid (FA) oxidation directly inside the adipocyte. Correspondingly, modulation of EC and smooth muscle cell metabolism of lipids may result in a method of regulating adipocyte fat storage as well as angiogenesis.

Figure 9E:
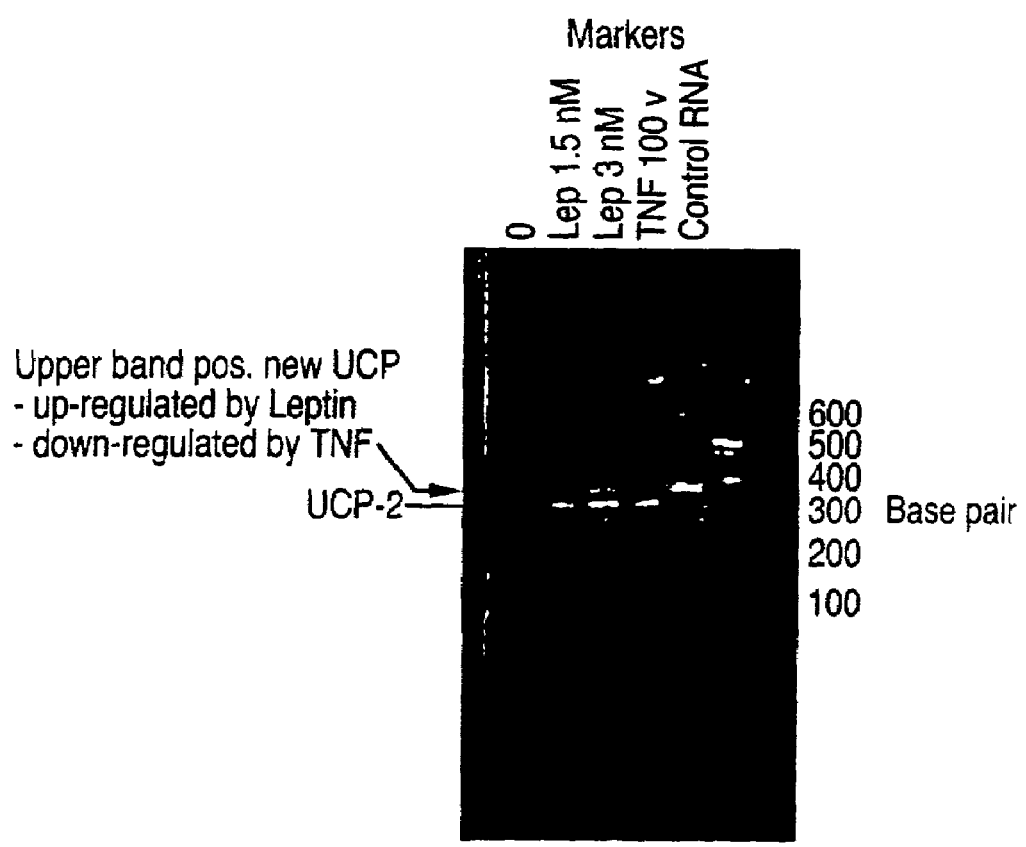

In FIG. 9E, RT-PCR was performed and shows the expression of uncoupling protein 2 (UCP-2) transcripts in endothelial cells. When leptin was added to the endothelial cells, the UCP-2 transcript was observed to be up-regulated. The same band was observed to be down-regulated by TNF.

Example 13

Role of Leptin in Wound Healing

Leptin deficiency in experimental animals leads to a complex phenotype of obesity, type II diabetes and severely impaired wound healing. We have been able to successfully treat and accelerate healing of experimental incisional skin wounds using a single topical dose of mouse recombinant leptin. We have also established the temporal pattern of expression of leptin in the wound site. Leptin appears to be upregulated by 12 hours, reaches a peak at 24 hours and remains high until complete healing is completed. Also, we have found transiently increased leptin levels in the circulation of experimentally wounded mice, including in a wound model where a SCID strain of mice are transplanted with a small fragment of human skin (from elective plastic surgery). The mice are wounded on the human graft and the serum leptin levels are measured at 12 hours after incision is made. In this case, we have found that the increase in circulating leptin is human leptin. These experiments indicate that the peak of leptin found after wounding is generated at the wound site.

Our studies on cutaneous wound healing demonstrate that: a) leptin is produced acutely in wounded or lacerated tissue, b) that blockage of leptin action with neutralizing antibodies prevents the normal healing process and c) that direct treatment of experimental wounds with recombinant leptin enhances and accelerates wound repair. Sections from two parallel wounds were prepared from the same animal. Three days after wounding, the control wound began to heal and a normal pattern of repithelialization was present. In contrast, the contralateral wound treated with leptin healed and complete reepithelialization was evident.

The process of myocardial healing after ischemic injury has distinctive characteristics that differ from skin healing. The angiogenic activity of leptin also enhances repair of injured tissue irrespective of its location in the body. The serum leptin concentrations of patients has been evaluated at different times following myocardial infraction. Data indicate that there is a marked increase in circulating leptin between 12 and 24 hours after a heart attack. The elevated leptin is sustained for another 24 hours and returns to normal values by 72 hours post-infarct.

Although the present invention has been described in detail with reference to examples above, it is understood that various modifications can be made without departing from the spirit of the invention. For example, although particular ligands of the leptin receptor (such as leptin) are identified above, one skilled in the art will recognize that other agonists and antagonists of the leptin receptor are contemplated, particularly those having decreased side effects, greater selectivity, greater bioavailability, etc. Accordingly, the invention is limited only by the following claims. All references, articles, texts and other documents referred to above, including the U.S. parent provisional application to the application No. 60/086,354 filed May 20, 1998, are hereby incorporated by reference in their entirety.

What is claimed is:

1. A method to promote wound healing in a subject in need thereof, comprising: providing an agent capable of inducing a leptin or leptin receptor-mediated angiogenic response; and administering to a subject in need of wound healing, an effective amount of the agent to promote wound healing, wherein the agent is leptin.

2. The method of claim 1, wherein the angiogenic response affects vascular cells in the subject.

3. The method of claim 1, wherein administering comprises administering the agent locally and the vascular cell response occurs locally.

* * * * *

UNITED STATES PATENT AND TRADEMARK OFFICE
CERTIFICATE OF CORRECTION

PATENT NO.       : 7,261,881 B1                        Page 1 of 1
APPLICATION NO.  : 09/700813
DATED            : August 28, 2007
INVENTOR(S)      : Rocio M. Sierra-Honigmann It is certified that error appears in the above-identified patent and that said Letters Patent is hereby corrected as shown below:

Column 1, line 4: under the title of the invention, insert the following:

--FEDERAL SUPPORT

This invention was made with U.S. Government support under National Institutes of Health Grant No. HL031446. The U.S. Government has certain rights in this invention.--

Signed and Sealed this

Fourth Day of December, 2007

JON W. DUDAS
*Director of the United States Patent and Trademark Office*

SEQUENCE LISTING

<160> NUMBER OF SEQ ID NOS: 21

<210> SEQ ID NO 1
<211> LENGTH: 3656
<212> TYPE: DNA
<213> ORGANISM: Mus musculus

<400> SEQUENCE: 1

```
aggtgatttg cagcggtgag gaaaaaacca gacccgaccg aggaatcgtt ctgcaaatcc      60
aggtgtacac ctctgaagaa agatgatgtg tcagaaattc tatgtggttt tgttacactg     120
ggaatttctt tatgtgatag ctgcacttaa cctggcatat ccaatctctc cctggaaatt     180
taagttgttt tgtggaccac cgaacacaac cgatgactcc tttctctcac ctgctggagc     240
cccaaacaat gcctcggctt tgaaggggggc ttctgaagca attgttgaag ctaaatttaa     300
ttcaagtggt atctacgttc ctgagttatc caaaacagtc ttccactgtt gctttgggaa     360
tgagcaaggt caaaactgct ctgcactcac agacaacact gaagggaaga cactggcttc     420
agtagtgaag gcttcagttt ttcgccagct aggtgtaaac tgggacatag agtgctggat     480
gaaaggggac ttgacattaa tcatctgtca tatggagcca ttacctaaga accccttcaa     540
gaattatgac tctaaggtcc atcttttata tgatctgcct gaagtcatag atgattcgcc     600
tctgccccca ctgaaagaca gctttcagac tgtccaatgc aactgcagtc ttcggggatg     660
tgaatgtcat gtgccggtac ccagagccaa actcaactac gctcttctga tgtatttgga     720
aatcacatct gccggtgtga gttttcagtc acctctgatg tcactgcagc ccatgcttgt     780
tgtgaaaccc gatccaccct taggtttgca tatggaagtc acagatgatg gtaatttaaa     840
gatttcttgg gacagccaaa caatggcacc atttccgctt caatatcagg tgaaatattt     900
agagaattct acaattgtaa gagaggctgc tgaaattgtc tcagctacat ctctgctggt     960
agacagtgtg cttcctggat cttcatatga ggtccaggtg aggagcaaga gactggatgg    1020
ttcaggagtc tggagtgact ggagttcacc tcaagtcttt accacacaag atgttgtgta    1080
ttttccaccc aaaaattctga ctagtgttgg atcgaatgct tcttttcatt gcatctacaa    1140
aaacgaaaac cagattatct cctcaaaaca gatagtttgg tggaggaatc tagctgagaa    1200
aatccctgag atacagtaca gcattgtgag tgaccgagtt agcaaagtta ccttctccaa    1260
cctgaaagcc accagacctc gagggaagtt tacctatgac gcagtgtact gctgcaatga    1320
gcaggcgtgc catcaccgct atgctgaatt atacgtgatc gatgtcaata tcaatatatc    1380
atgtgaaact gacgggtact taactaaaat gacttgcaga tggtcaccca gcacaatcca    1440
atcactagtg ggaagcactg tgcagctgag gtatcacagg cgcagcctgt attgtcctga    1500
tagtccatct attcatccta cgtctgagcc caaaaactgc gtcttacaga gagacggctt    1560
ttatgaatgt gttttccagc caatctttct attatctggc tatacaatgt ggatcaggat    1620
caaccattct ttaggttcac ttgactcgcc accaacgtgt gtccttcctg actccgtagt    1680
aaaaccacta cctccatcta acgtaaaagc agagattact gtaaacactg gattattgaa    1740
agtatcttgg gaaaagccag tctttccgga gaataacctt caattccaga ttcgatatgg    1800
cttaagtgga aaagaaatac aatggaagac acatgaggta ttcgatgcaa agtcaaagtc    1860
tgccagcctg ctggtgtcag acctctgtgc agtctatgtg gtccaggttc gctgccggcg    1920
gttggatgga ctaggatatt ggagtaattg gagcagtcca gcctatacgc ttgtcatgga    1980
tgtaaaagtt cctatgagag ggcctgaatt ttggagaaaa atggatgggg acgttactaa    2040
```

-continued

```
aaaggagaga aatgtcacct tgctttggaa gccccctgacg aaaaatgact cactgtgtag   2100
tgtgaggagg tacgtggtga agcatcgtac tgcccacaat gggacgtggt cagaagatgt   2160
gggaaatcgg accaatctca ctttcctgtg gacagaacca gcgcacactg ttacagttct   2220
ggctgtcaat tccctcggcg cttcccttgt gaattttaac cttaccttct catggcccat   2280
gagtaaagtg agtgctgtgg agtcactcag tgcttatccc ctgagcagca gctgtgtcat   2340
cctttcctgg acactgtcac ctgatgatta tagtctgtta tatctggtta ttgaatggaa   2400
gatccttaat gaagatgatg gaatgaagtg gcttagaatt ccctcgaatg ttaaaaagtt   2460
ttatatccac gataatttta ttcccatcga gaaatatcag tttagtcttt acccagtatt   2520
tatggaagga gttggaaaac caaagataat taatggtttc accaaagatg ctatcgacaa   2580
gcagcagaat gacgcagggc tgtatgtcat tgtacccata attatttcct cttgtgtcct   2640
actgctcgga acactgttaa tttcacacca gagaatgaaa aagttgtttt gggacgatgt   2700
tccaaacccc aagaattgtt cctgggcaca aggactgaat ttccaaaagc ctgaaacatt   2760
tgagcatctt tttaccaagc acgcagaatc agtgatattt ggtcctcttc ttctggagcc   2820
tgaacccatt tcagaagaaa tcagtgtcga tacagcttgg aaaaataaag atgagatggt   2880
cccagcagct atggtctccc ttcttttgac cacaccagac cctgaaagca gttctatttg   2940
tattagtgac cagtgtaaca gtgctaactt ctctgggtct cagagcaccc aggtaacctg   3000
tgaggatgag tgtcagagac aaccctcagt taaatatgca actctggtca gcaacgataa   3060
actagtggaa actgatgaag agcaagggtt tatccatagt cctgtcagca actgcatctc   3120
cagtaatcat tccccactga ggcagtcttt ctctagcagc tcctgggaga cagaggccca   3180
gacatttttc cttttatcag accagcaacc caccatgatt tcaccacaac tttcattctc   3240
ggggttggat gagctttggg aactggaggg aagttttcct gaagaaaatc acagggagaa   3300
gtctgtctgt tatctaggag tcacctccgt caacagaaga gagagtggtg tgcttttgac   3360
tggtgaggca ggaatcctgt gcacattccc agcccagtgt ctgttcagtg acatcaggat   3420
cctccaggag agatgctcac actttgtaga aaataaatttg agtttaggga cctctggtga   3480
gaactttgta ccttacatgc cccaatttca aacctgttcc acgcacagtc acaagataat   3540
ggagaataag atgtgtgact taactgtgta atctcatcca agaagcctca aggttccatt   3600
ccagtagagc ctgtcatgta taatgtgttc ttttattgtt gtgggtggga gagaga        3656
```

<210> SEQ ID NO 2
<211> LENGTH: 1162
<212> TYPE: PRT
<213> ORGANISM: Mus musculus

<400> SEQUENCE: 2

```
Met Met Cys Gln Lys Phe Tyr Val Val Leu Leu His Trp Glu Phe Leu
1               5                   10                  15

Tyr Val Ile Ala Ala Leu Asn Leu Ala Tyr Pro Ile Ser Pro Trp Lys
            20                  25                  30

Phe Lys Leu Phe Cys Gly Pro Pro Asn Thr Thr Asp Asp Ser Phe Leu
        35                  40                  45

Ser Pro Ala Gly Ala Pro Asn Asn Ala Ser Ala Leu Lys Gly Ala Ser
    50                  55                  60

Glu Ala Ile Val Glu Ala Lys Phe Asn Ser Ser Gly Ile Tyr Val Pro
65                  70                  75                  80

Glu Leu Ser Lys Thr Val Phe His Cys Cys Phe Gly Asn Glu Gln Gly
```

-continued

```
                85                  90                  95
Gln Asn Cys Ser Ala Leu Thr Asp Asn Thr Glu Gly Lys Thr Leu Ala
            100                 105                 110
Ser Val Val Lys Ala Ser Val Phe Arg Gln Leu Gly Val Asn Trp Asp
            115                 120                 125
Ile Glu Cys Trp Met Lys Gly Asp Leu Thr Leu Ile Ile Cys His Met
            130                 135                 140
Glu Pro Leu Pro Lys Asn Pro Phe Lys Asn Tyr Asp Ser Lys Val His
145                 150                 155                 160
Leu Leu Tyr Asp Leu Pro Glu Val Ile Asp Asp Ser Pro Leu Pro Pro
                165                 170                 175
Leu Lys Asp Ser Phe Gln Thr Val Gln Cys Asn Cys Ser Leu Arg Gly
            180                 185                 190
Cys Glu Cys His Val Pro Val Pro Arg Ala Lys Leu Asn Tyr Ala Leu
            195                 200                 205
Leu Met Tyr Leu Glu Ile Thr Ser Ala Gly Val Ser Phe Gln Ser Pro
            210                 215                 220
Leu Met Ser Leu Gln Pro Met Leu Val Val Lys Pro Asp Pro Pro Leu
225                 230                 235                 240
Gly Leu His Met Glu Val Thr Asp Asp Gly Asn Leu Lys Ile Ser Trp
                245                 250                 255
Asp Ser Gln Thr Met Ala Pro Phe Pro Leu Gln Tyr Gln Val Lys Tyr
            260                 265                 270
Leu Glu Asn Ser Thr Ile Val Arg Glu Ala Ala Glu Ile Val Ser Ala
            275                 280                 285
Thr Ser Leu Leu Val Asp Ser Val Leu Pro Gly Ser Ser Tyr Glu Val
            290                 295                 300
Gln Val Arg Ser Lys Arg Leu Asp Gly Ser Gly Val Trp Ser Asp Trp
305                 310                 315                 320
Ser Ser Pro Gln Val Phe Thr Thr Gln Asp Val Val Tyr Phe Pro Pro
            325                 330                 335
Lys Ile Leu Thr Ser Val Gly Ser Asn Ala Ser Phe His Cys Ile Tyr
            340                 345                 350
Lys Asn Glu Asn Gln Ile Ile Ser Ser Lys Gln Ile Val Trp Trp Arg
            355                 360                 365
Asn Leu Ala Glu Lys Ile Pro Glu Ile Gln Tyr Ser Ile Val Ser Asp
            370                 375                 380
Arg Val Ser Lys Val Thr Phe Ser Asn Leu Lys Ala Thr Arg Pro Arg
385                 390                 395                 400
Gly Lys Phe Thr Tyr Asp Ala Val Tyr Cys Cys Asn Glu Gln Ala Cys
                405                 410                 415
His His Arg Tyr Ala Glu Leu Tyr Val Ile Asp Val Asn Ile Asn Ile
            420                 425                 430
Ser Cys Glu Thr Asp Gly Tyr Leu Thr Lys Met Thr Cys Arg Trp Ser
            435                 440                 445
Pro Ser Thr Ile Gln Ser Leu Val Gly Ser Thr Val Gln Leu Arg Tyr
            450                 455                 460
His Arg Arg Ser Leu Tyr Cys Pro Asp Ser Pro Ser Ile His Pro Thr
465                 470                 475                 480
Ser Glu Pro Lys Asn Cys Val Leu Gln Arg Asp Gly Phe Tyr Glu Cys
                485                 490                 495
Val Phe Gln Pro Ile Phe Leu Leu Ser Gly Tyr Thr Met Trp Ile Arg
            500                 505                 510
```

-continued

```
Ile Asn His Ser Leu Gly Ser Leu Asp Ser Pro Thr Cys Val Leu
        515                 520                 525

Pro Asp Ser Val Val Lys Pro Leu Pro Ser Asn Val Lys Ala Glu
530                 535                 540

Ile Thr Val Asn Thr Gly Leu Leu Lys Val Ser Trp Glu Lys Pro Val
545                 550                 555                 560

Phe Pro Glu Asn Asn Leu Gln Phe Gln Ile Arg Tyr Gly Leu Ser Gly
                565                 570                 575

Lys Glu Ile Gln Trp Lys Thr His Glu Val Phe Asp Ala Lys Ser Lys
            580                 585                 590

Ser Ala Ser Leu Leu Val Ser Asp Leu Cys Ala Val Tyr Val Gln
        595                 600                 605

Val Arg Cys Arg Arg Leu Asp Gly Leu Gly Tyr Trp Ser Asn Trp Ser
        610                 615                 620

Ser Pro Ala Tyr Thr Leu Val Met Asp Val Lys Val Pro Met Arg Gly
625                 630                 635                 640

Pro Glu Phe Trp Arg Lys Met Asp Gly Asp Val Thr Lys Lys Glu Arg
                645                 650                 655

Asn Val Thr Leu Leu Trp Lys Pro Leu Thr Lys Asn Asp Ser Leu Cys
                660                 665                 670

Ser Val Arg Arg Tyr Val Val Lys His Arg Thr Ala His Asn Gly Thr
        675                 680                 685

Trp Ser Glu Asp Val Gly Asn Arg Thr Asn Leu Thr Phe Leu Trp Thr
        690                 695                 700

Glu Pro Ala His Thr Val Thr Val Leu Ala Val Asn Ser Leu Gly Ala
705                 710                 715                 720

Ser Leu Val Asn Phe Asn Leu Thr Phe Ser Trp Pro Met Ser Lys Val
                725                 730                 735

Ser Ala Val Glu Ser Leu Ser Ala Tyr Pro Leu Ser Ser Ser Cys Val
                740                 745                 750

Ile Leu Ser Trp Thr Leu Ser Pro Asp Asp Tyr Ser Leu Leu Tyr Leu
        755                 760                 765

Val Ile Glu Trp Lys Ile Leu Asn Glu Asp Asp Gly Met Lys Trp Leu
770                 775                 780

Arg Ile Pro Ser Asn Val Lys Lys Phe Tyr Ile His Asp Asn Phe Ile
785                 790                 795                 800

Pro Ile Glu Lys Tyr Gln Phe Ser Leu Tyr Pro Val Phe Met Glu Gly
                805                 810                 815

Val Gly Lys Pro Lys Ile Ile Asn Gly Phe Thr Lys Asp Ala Ile Asp
                820                 825                 830

Lys Gln Gln Asn Asp Ala Gly Leu Tyr Val Ile Val Pro Ile Ile Ile
            835                 840                 845

Ser Ser Cys Val Leu Leu Leu Gly Thr Leu Leu Ile Ser His Gln Arg
        850                 855                 860

Met Lys Lys Leu Phe Trp Asp Asp Val Pro Asn Pro Lys Asn Cys Ser
865                 870                 875                 880

Trp Ala Gln Gly Leu Asn Phe Gln Lys Pro Glu Thr Phe Glu His Leu
                885                 890                 895

Phe Thr Lys His Ala Glu Ser Val Ile Phe Gly Pro Leu Leu Leu Glu
            900                 905                 910

Pro Glu Pro Ile Ser Glu Glu Ile Ser Val Asp Thr Ala Trp Lys Asn
        915                 920                 925
```

```
Lys Asp Glu Met Val Pro Ala Ala Met Val Ser Leu Leu Leu Thr Thr
    930             935                 940
Pro Asp Pro Glu Ser Ser Ile Cys Ile Ser Asp Gln Cys Asn Ser
945             950                 955                 960
Ala Asn Phe Ser Gly Ser Gln Ser Thr Gln Val Thr Cys Glu Asp Glu
                965                 970                 975
Cys Gln Arg Gln Pro Ser Val Lys Tyr Ala Thr Leu Val Ser Asn Asp
            980                 985                 990
Lys Leu Val Glu Thr Asp Glu Glu Gln Gly Phe Ile His Ser Pro Val
        995                 1000                1005
Ser Asn Cys Ile Ser Ser Asn His Ser Pro Leu Arg Gln Ser Phe
    1010                1015                1020
Ser Ser Ser Ser Trp Glu Thr Glu Ala Gln Thr Phe Phe Leu Leu
    1025                1030                1035
Ser Asp Gln Gln Pro Thr Met Ile Ser Pro Gln Leu Ser Phe Ser
    1040                1045                1050
Gly Leu Asp Glu Leu Leu Glu Leu Glu Gly Ser Phe Pro Glu Glu
    1055                1060                1065
Asn His Arg Glu Lys Ser Val Cys Tyr Leu Gly Val Thr Ser Val
    1070                1075                1080
Asn Arg Arg Glu Ser Gly Val Leu Leu Thr Gly Glu Ala Gly Ile
    1085                1090                1095
Leu Cys Thr Phe Pro Ala Gln Cys Leu Phe Ser Asp Ile Arg Ile
    1100                1105                1110
Leu Gln Glu Arg Cys Ser His Phe Val Glu Asn Asn Leu Ser Leu
    1115                1120                1125
Gly Thr Ser Gly Glu Asn Phe Val Pro Tyr Met Pro Gln Phe Gln
    1130                1135                1140
Thr Cys Ser Thr His Ser His Lys Ile Met Glu Asn Lys Met Cys
    1145                1150                1155
Asp Leu Thr Val
    1160

<210> SEQ ID NO 3
<211> LENGTH: 539
<212> TYPE: DNA
<213> ORGANISM: Rattus norvegicus

<400> SEQUENCE: 3
ccaagaagaa gaagacccca gcgaggaaaa tgtgctggag acccctgtgc cggttcctgt      60
ggctttggtc ctatctgtcc tatgttcaag ctgtgcctat ccacaaagtc caggatgaca    120
ccaaaaccct catcaagacc attgtcacca ggatcaatga catttcacac acgcagtcgg    180
tatccgccag gcagagggtc accggtttgg acttcattcc gggcttcac cccattctga     240
gtttgtccaa gatggaccag accctggcag tctatcaaca gatcctcacc agcttgcctt    300
cccaaaacgt gctgcagata gctcatgacc tggagaacct gcgagacctc ctccatctgc    360
tggccttctc caagagctgc tccctgccgc agacccgtgg cctgcagaag ccagagagcc    420
tggatggcgt cctggaagcc tcgctctact ccacagaggt ggtggctctg agcaggctgc    480
agggctctct gcaggacatt cttcaacagt tggaccttag ccctgaatgc tgaggtttc     539

<210> SEQ ID NO 4
<211> LENGTH: 167
<212> TYPE: PRT
<213> ORGANISM: Rattus norvegicus
```

<400> SEQUENCE: 4

```
Met Cys Trp Arg Pro Leu Cys Arg Phe Leu Trp Leu Trp Ser Tyr Leu
1               5                   10                  15
Ser Tyr Val Gln Ala Val Pro Ile His Lys Val Gln Asp Asp Thr Lys
            20                  25                  30
Thr Leu Ile Lys Thr Ile Val Thr Arg Ile Asn Asp Ile Ser His Thr
        35                  40                  45
Gln Ser Val Ser Ala Arg Gln Arg Val Thr Gly Leu Asp Phe Ile Pro
    50                  55                  60
Gly Leu His Pro Ile Leu Ser Leu Ser Lys Met Asp Gln Thr Leu Ala
65                  70                  75                  80
Val Tyr Gln Gln Ile Leu Thr Ser Leu Pro Ser Gln Asn Val Leu Gln
            85                  90                  95
Ile Ala His Asp Leu Glu Asn Leu Arg Asp Leu Leu His Leu Leu Ala
        100                 105                 110
Phe Ser Lys Ser Cys Ser Leu Pro Gln Thr Arg Gly Leu Gln Lys Pro
    115                 120                 125
Glu Ser Leu Asp Gly Val Leu Glu Ala Ser Leu Tyr Ser Thr Glu Val
    130                 135                 140
Val Ala Leu Ser Arg Leu Gln Gly Ser Leu Gln Asp Ile Leu Gln Gln
145                 150                 155                 160
Leu Asp Leu Ser Pro Glu Cys
                165
```

<210> SEQ ID NO 5
<211> LENGTH: 3650
<212> TYPE: DNA
<213> ORGANISM: Rattus norvegicus

<400> SEQUENCE: 5

```
tggggcaatt gggctgacct ttcttatgct gggatgtgcc ttggaggact atgggtgtct      60
atctctgaag taagatgacg tgtcagaaat tctatgtggt tttgttacac tgggaatttc    120
tgtatgtgat aactgcactt aacctggcct atccaacctc tccctggaga tttaagctgt    180
tttgtgcgcc accgagtaca actgatgact ccttctctc tcctgctgga gtcccaaaca     240
atacttcgtc tttgaagggg gcttctgaag cacttgttga agctaaattt aattcaactg    300
gtatctacgt ttctgagtta tccaaaacca ttttccactg ttgctttggg aatgagcaag    360
gtcaaaactg ctccgcactc acaggcaaca ctgaagggaa gacgctggct tcagtggtga    420
agcctttagt tttccgccaa ctaggtgtaa actgggacat agagtgctgg atgaaagggg    480
acttgacatt attcatctgt catatggaac cattacttaa gaacccttc aagaattatg     540
actctaaggt tcaccttta tatgatctgc ctgaagttat agatgatttg cctctgcccc     600
cactgaaaga cagctttcag actgtccagt gcaactgcag tgttcgggaa tgcgaatgtc    660
atgtaccagt acccagagcc aaagtcaact acgctcttct gatgtattta gaaatcacat    720
ctgctggtgt gagttttcag tcacctctaa tgtcactgca gcccatgctt gttgtgaagc    780
ccgatccacc gctgggtttg cgtatggaag tcacagatga tggtaattta agatttcat    840
gggacagcca aacaaaagca ccatttccac ttcaatatca ggtgaaatat ttagagaatt    900
ctacaatcgt aagagaggct gctgaaatcg tctcggatac atctctgctg gtagacagcg    960
tgcttcctgg gtcttcatac gaggtccagg tgaggagcaa gagactggat ggctcaggag   1020
tctggagtga ctggagttta cctcaactct ttaccacaca agatgtcatg tattttccac   1080
```

-continued

```
ccaaaattct gacgagtgtt ggatccaatg cttcctttg ctgcatctac aaaaatgaga      1140
accagactat ctcctcaaaa caaatagttt ggtggatgaa tctagccgag aagatccccg      1200
agacacagta caacactgtg agtgaccaca ttagcaaagt cactttctcc aacctgaaag      1260
ccaccagacc tcgagggaag tttacctatg atgcagtgta ctgctgcaat gagcaggcat      1320
gccatcaccg ctacgctgaa ttatatgtga tcgatgtcaa tatcaatata tcatgtgaaa      1380
ctgacgggta cttaactaaa atgacttgca gatggtcacc cagcacaatc caatcactag      1440
tgggaagcac tgtgcagttg aggtatcaca ggcgcagcct gtactgtccc gataatccat      1500
ctattcgtcc tacatcagag ctcaaaaact gcgtcttaca gacagatggc ttttatgaat      1560
gtgttttcca gccaatcttt ctattatctg gctatacaat gtggatcagg atcaaccatt      1620
ctttaggttc acttgactct ccaccaacgt gtgtccttcc tgactccgta gtaaaaccac      1680
tacctccatc taatgtaaaa gcagagatta ctataaacac tggattattg aaagtatctt      1740
gggaaaagcc agtctttcca gagaataacc ttcagttcca gattcgatat ggcttaaatg      1800
gaaaagaaat acaatggaag acacacgagg tattcgatgc aaaatcaaaa tcggccagcc      1860
tgccagtgtc agatctctgt gcggtctatg tggtacaggt tcgctgccgg cggttggatg      1920
gactagggta ttggagtaat tggagcagtc cagcctacac tcttgtcatg gatgtaaaag      1980
ttcctatgag agggcctgaa ttctggagaa taatggatgg ggatattact aaaaaggaga      2040
gaaatgtcac cttgctttgg aagccactga tgaaaaatga ctcactgtgt agtgtgagga      2100
ggtatgtggt gaagcatcgt actgcccaca atggacatg gtcacaagat gtgggaaatc      2160
agaccaatct cactttcctg tgggcagaat cagcacacac tgttacagtt ctggccatca      2220
attccatcgg tgcctccctt gtgaatttta accttacgtt ctcatggccc atgagtaaag      2280
tgaatgctgt gcagtcactc agtgcttatc ccctgagcag cagctgcgtc atcctttcct      2340
ggacactgtc acctaatgat tatagtctgt tatatctggt tattgaatgg aagaacctta      2400
atgatgatga tggaatgaag tggcttagaa tcccttcgaa tgttaacaag tattatatcc      2460
atgataattt tattcctatc gagaaatatc agtttagtct ttacccagta tttatggaag      2520
gagttggaaa accaaagata attaatggtt tcaccaaaga tgatatcgcc aaacagcaaa      2580
atgatgcagg gctgtatgtc attgtaccga taattatttc ctcttgtgtc ctgctgctcg      2640
gaacactgtt aatttcacac cagagaatga aaaagttgtt ttgggacgat gttccaaacc      2700
ccaagaattg ttcctgggca caaggactta atttccaaaa gcctgaaaca tttgagcatc      2760
tttttaccaa gcatgcagaa tcagtgatat ttggtcctct tcttctggag cctgaaccag      2820
tttcagaaga aatcagtgtc gatacagctt ggaaaaataa agatgagatg gtaccagcag      2880
ctatggtctc acttcttttg accactccag attccacaag gggttctatt tgtatcagtg      2940
accagtgtaa cagtgctaac ttctctgggg ctcagagcac ccaggaacc tgtgaggatg      3000 agtgtcagag tcaaccctca gttaaatatg caacgctggt cagcaacgtg aaaacagtgg      3060
aaactgatga agagcaaggg gctatacata gttctgtcag ccagtgcatc gccaggaaac      3120
attccccact gagacagtct ttttctagca actcctggga gatagaggcc caggcatttt      3180 tcctttttatc agatcatcca cccaatgtga tttcaccaca actttcattc tcagggttgg      3240
atgagctttt ggaactggag ggaaattttc ctgaagaaaa tcacgggaa aaatctgtgt      3300 attatctagg agtctcctca ggaaacaaaa gagagaatga tatgcttttg actgatgagg      3360 cagggggtatt gtgcccattc ccagctcact gtctgttcag tgacatcaga atcctccagg      3420
```

-continued

```
agagttgttc acactttgta gaaataatt tgaatttagg gacctctggt aagaactttg    3480
taccttacat gccccagttt caatcctgtt ccactcacag tcataagata atagaaaata    3540
agatgtgtga cttaactgtg taatcttgtc caaaaacttc caggttccat tccagtagag    3600
tgtgtcatgt ataatatgtt cttttatagt tgtgggtggg agagaaagcc              3650
```

<210> SEQ ID NO 6
<211> LENGTH: 1162
<212> TYPE: PRT
<213> ORGANISM: Rattus norvegicus

<400> SEQUENCE: 6

```
Met Thr Cys Gln Lys Phe Tyr Val Val Leu His Trp Glu Phe Leu
1               5                   10                  15

Tyr Val Ile Thr Ala Leu Asn Leu Ala Tyr Pro Thr Ser Pro Trp Arg
            20                  25                  30

Phe Lys Leu Phe Cys Ala Pro Pro Ser Thr Thr Asp Asp Ser Phe Leu
        35                  40                  45

Ser Pro Ala Gly Val Pro Asn Asn Thr Ser Ser Leu Lys Gly Ala Ser
    50                  55                  60

Glu Ala Leu Val Glu Ala Lys Phe Asn Ser Thr Gly Ile Tyr Val Ser
65                  70                  75                  80

Glu Leu Ser Lys Thr Ile Phe His Cys Cys Phe Gly Asn Glu Gln Gly
                85                  90                  95

Gln Asn Cys Ser Ala Leu Thr Gly Asn Thr Glu Gly Lys Thr Leu Ala
            100                 105                 110

Ser Val Val Lys Pro Leu Val Phe Arg Gln Leu Gly Val Asn Trp Asp
        115                 120                 125

Ile Glu Cys Trp Met Lys Gly Asp Leu Thr Leu Phe Ile Cys His Met
    130                 135                 140

Glu Pro Leu Leu Lys Asn Pro Phe Lys Asn Tyr Asp Ser Lys Val His
145                 150                 155                 160

Leu Leu Tyr Asp Leu Pro Glu Val Ile Asp Asp Leu Pro Leu Pro Pro
                165                 170                 175

Leu Lys Asp Ser Phe Gln Thr Val Gln Cys Asn Cys Ser Val Arg Glu
            180                 185                 190

Cys Glu Cys His Val Pro Val Pro Arg Ala Lys Val Asn Tyr Ala Leu
        195                 200                 205

Leu Met Tyr Leu Glu Ile Thr Ser Ala Gly Val Ser Phe Gln Ser Pro
    210                 215                 220

Leu Met Ser Leu Gln Pro Met Leu Val Val Lys Pro Asp Pro Pro Leu
225                 230                 235                 240

Gly Leu Arg Met Glu Val Thr Asp Asp Gly Asn Leu Lys Ile Ser Trp
                245                 250                 255

Asp Ser Gln Thr Lys Ala Pro Phe Pro Leu Gln Tyr Gln Val Lys Tyr
            260                 265                 270

Leu Glu Asn Ser Thr Ile Val Arg Glu Ala Ala Glu Ile Val Ser Asp
        275                 280                 285

Thr Ser Leu Leu Val Asp Ser Val Leu Pro Gly Ser Ser Tyr Glu Val
    290                 295                 300

Gln Val Arg Ser Lys Arg Leu Asp Gly Ser Gly Val Trp Ser Asp Trp
305                 310                 315                 320

Ser Leu Pro Gln Leu Phe Thr Thr Gln Asp Val Met Tyr Phe Pro Pro
                325                 330                 335
```

-continued

```
Lys Ile Leu Thr Ser Val Gly Ser Asn Ala Ser Phe Cys Cys Ile Tyr
            340                 345                 350

Lys Asn Glu Asn Gln Thr Ile Ser Ser Lys Gln Ile Val Trp Trp Met
            355                 360                 365

Asn Leu Ala Glu Lys Ile Pro Glu Thr Gln Tyr Asn Thr Val Ser Asp
            370                 375                 380

His Ile Ser Lys Val Thr Phe Ser Asn Leu Lys Ala Thr Arg Pro Arg
385                 390                 395                 400

Gly Lys Phe Thr Tyr Asp Ala Val Tyr Cys Cys Asn Glu Gln Ala Cys
            405                 410                 415

His His Arg Tyr Ala Glu Leu Tyr Val Ile Asp Val Asn Ile Asn Ile
            420                 425                 430

Ser Cys Glu Thr Asp Gly Tyr Leu Thr Lys Met Thr Cys Arg Trp Ser
            435                 440                 445

Pro Ser Thr Ile Gln Ser Leu Val Gly Ser Thr Val Gln Leu Arg Tyr
            450                 455                 460

His Arg Arg Ser Leu Tyr Cys Pro Asp Asn Pro Ser Ile Arg Pro Thr
465                 470                 475                 480

Ser Glu Leu Lys Asn Cys Val Leu Gln Thr Asp Gly Phe Tyr Glu Cys
            485                 490                 495

Val Phe Gln Pro Ile Phe Leu Leu Ser Gly Tyr Thr Met Trp Ile Arg
            500                 505                 510

Ile Asn His Ser Leu Gly Ser Leu Asp Ser Pro Pro Thr Cys Val Leu
            515                 520                 525

Pro Asp Ser Val Val Lys Pro Leu Pro Pro Ser Asn Val Lys Ala Glu
            530                 535                 540

Ile Thr Ile Asn Thr Gly Leu Leu Lys Val Ser Trp Glu Lys Pro Val
545                 550                 555                 560

Phe Pro Glu Asn Asn Leu Gln Phe Gln Ile Arg Tyr Gly Leu Asn Gly
            565                 570                 575

Lys Glu Ile Gln Trp Lys Thr His Glu Val Phe Asp Ala Lys Ser Lys
            580                 585                 590

Ser Ala Ser Leu Pro Val Ser Asp Leu Cys Ala Val Tyr Val Val Gln
            595                 600                 605

Val Arg Cys Arg Arg Leu Asp Gly Leu Gly Tyr Trp Ser Asn Trp Ser
            610                 615                 620

Ser Pro Ala Tyr Thr Leu Val Met Asp Val Lys Val Pro Met Arg Gly
625                 630                 635                 640

Pro Glu Phe Trp Arg Ile Met Asp Gly Asp Ile Thr Lys Lys Glu Arg
            645                 650                 655

Asn Val Thr Leu Leu Trp Lys Pro Leu Met Lys Asn Asp Ser Leu Cys
            660                 665                 670

Ser Val Arg Arg Tyr Val Val Lys His Arg Thr Ala His Asn Gly Thr
            675                 680                 685

Trp Ser Gln Asp Val Gly Asn Gln Thr Asn Leu Thr Phe Leu Trp Ala
            690                 695                 700

Glu Ser Ala His Thr Val Thr Val Leu Ala Ile Asn Ser Ile Gly Ala
705                 710                 715                 720

Ser Leu Val Asn Phe Asn Leu Thr Phe Ser Trp Pro Met Ser Lys Val
            725                 730                 735

Asn Ala Val Gln Ser Leu Ser Ala Tyr Pro Leu Ser Ser Ser Cys Val
            740                 745                 750

Ile Leu Ser Trp Thr Leu Ser Pro Asn Asp Tyr Ser Leu Leu Tyr Leu
```

-continued

```
            755                 760                 765
Val Ile Glu Trp Lys Asn Leu Asn Asp Asp Gly Met Lys Trp Leu
770                 775                 780

Arg Ile Pro Ser Asn Val Asn Lys Tyr Tyr Ile His Asp Asn Phe Ile
785                 790                 795                 800

Pro Ile Glu Lys Tyr Gln Phe Ser Leu Tyr Pro Val Phe Met Glu Gly
                    805                 810                 815

Val Gly Lys Pro Lys Ile Ile Asn Gly Phe Thr Lys Asp Asp Ile Ala
                    820                 825                 830

Lys Gln Gln Asn Asp Ala Gly Leu Tyr Val Ile Val Pro Ile Ile Ile
                    835                 840                 845

Ser Ser Cys Val Leu Leu Leu Gly Thr Leu Leu Ile Ser His Gln Arg
850                 855                 860

Met Lys Lys Leu Phe Trp Asp Asp Val Pro Asn Pro Lys Asn Cys Ser
865                 870                 875                 880

Trp Ala Gln Gly Leu Asn Phe Gln Lys Pro Glu Thr Phe Glu His Leu
                    885                 890                 895

Phe Thr Lys His Ala Glu Ser Val Ile Phe Gly Pro Leu Leu Leu Glu
                    900                 905                 910

Pro Glu Pro Val Ser Glu Glu Ile Ser Val Asp Thr Ala Trp Lys Asn
                    915                 920                 925

Lys Asp Glu Met Val Pro Ala Ala Met Val Ser Leu Leu Leu Thr Thr
                    930                 935                 940

Pro Asp Ser Thr Arg Gly Ser Ile Cys Ile Ser Asp Gln Cys Asn Ser
945                 950                 955                 960

Ala Asn Phe Ser Gly Ala Gln Ser Thr Gln Gly Thr Cys Glu Asp Glu
                    965                 970                 975

Cys Gln Ser Gln Pro Ser Val Lys Tyr Ala Thr Leu Val Ser Asn Val
                    980                 985                 990

Lys Thr Val Glu Thr Asp Glu Glu  Gln Gly Ala Ile His  Ser Ser Val
                    995                 1000                1005

Ser Gln  Cys Ile Ala Arg Lys  His Ser Pro Leu Arg  Gln Ser Phe
1010                1015                1020

Ser Ser  Asn Ser Trp Glu Ile  Glu Ala Gln Ala Phe  Phe Leu Leu
1025                1030                1035

Ser Asp  His Pro Pro Asn Val  Ile Ser Pro Gln Leu  Ser Phe Ser
1040                1045                1050

Gly Leu  Asp Glu Leu Leu Glu  Leu Glu Gly Asn Phe  Pro Glu Glu
1055                1060                1065

Asn His  Gly Glu Lys Ser Val  Tyr Tyr Leu Gly Val  Ser Ser Gly
1070                1075                1080

Asn Lys  Arg Glu Asn Asp Met  Leu Leu Thr Asp Glu  Ala Gly Val
1085                1090                1095

Leu Cys  Pro Phe Pro Ala His  Cys Leu Phe Ser Asp  Ile Arg Ile
1100                1105                1110

Leu Gln  Glu Ser Cys Ser His  Phe Val Glu Asn Asn  Leu Asn Leu
1115                1120                1125

Gly Thr  Ser Gly Lys Asn Phe  Val Pro Tyr Met Pro  Gln Phe Gln
1130                1135                1140

Ser Cys  Ser Thr His Ser His  Lys Ile Ile Glu Asn  Lys Met Cys
1145                1150                1155

Asp Leu  Thr Val
1160
```

<210> SEQ ID NO 7
<211> LENGTH: 3489
<212> TYPE: DNA
<213> ORGANISM: Rattus norvegicus

<400> SEQUENCE: 7

| | | | | | |
|---|---|---|---|---|---|
| atgatgtgtc | agaaattcta | tgtggttttg | ttacactggg | aatttctgta | tgtgataact | 60 |
| gcacttaacc | tggcctatcc | aacctctccc | tggagattta | agctgttttg | tgcgccaccg | 120 |
| agtacaactg | atgactcctt | tctctctcct | gctggagtcc | caaacaatac | ttcgtctttg | 180 |
| aaggggcttc | tgaagcact | tgttgaagct | aaatttaatt | caactggcat | ctacgtttct | 240 |
| gagttatcca | aaaccatttt | ccactgttgc | tttgggaatg | agcaaggtca | aaactgctcc | 300 |
| gcactcacag | gcaacactga | agggaagacg | ctggcttcag | tggtgaagcc | tttagttttc | 360 |
| cgccaactag | gtgtaaactg | ggacatagag | tgctggatga | aggggacttt | gacattattc | 420 |
| atctgtcata | tggaaccatt | acttaagaac | cccttcaaga | attatgactc | taaggttcac | 480 |
| cttttatatg | atctgcctga | agttatagat | gatttgcctc | tgcccccact | gaaagacagc | 540 |
| tttcagactg | tccagtgcaa | ctgcagtgtt | cgggaatgcg | aatgtcatgt | accagtaccc | 600 |
| agagccaaag | tcaactacgc | tcttctgatg | tatttagaaa | tcacatctgc | tggtgtgagt | 660 |
| tttcagtcac | ctctaatgtc | actgcagccc | atgcttgttg | tgaagcccga | tccaccgctg | 720 |
| ggtttgcgta | tggaagtcac | agatgatggt | aatttaaaga | tttcatggga | cagccaaaca | 780 |
| aaagcaccat | ttccacttca | atatcaggtg | aaatatttag | agaattctac | aatcgtaaga | 840 |
| gaggctgctg | aaatcgtctc | ggatacatct | ctgctggtag | acagcgtgct | tcctgggtct | 900 |
| tcatacgagg | tccaggtgag | gagcaagaga | ctggatggct | caggagtctg | gagtgactgg | 960 |
| agtttacctc | aactctttac | cacacaagat | gtcatgtatt | ttccacccaa | aattctgacg | 1020 |
| agtgttggat | ccaatgcttc | cttttgctgc | atctacaaaa | atgagaacca | gactatctcc | 1080 |
| tcaaaacaaa | tagtttggtg | gatgaatcta | gccgagaaga | tccccgagac | acagtacaac | 1140 |
| actgtgagtg | accacattag | caaagtcact | ttctccaacc | tgaaagccac | cagacctcga | 1200 |
| gggaagttta | cctatgatgc | agtgtactgc | tgcaatgagc | aggcatgcca | tcaccgctac | 1260 |
| gctgaattat | atgtgatcga | tgtcaatatc | aatatatcat | gtgaaactga | cgggtactta | 1320 |
| actaaaatga | cttgcagatg | gtcacccagc | acaatccaat | cactagtggg | aagcactgtg | 1380 |
| cagttgaggt | atcacaggcg | cagcctgtac | tgtcccgata | tccatctat | tcgtcctaca | 1440 |
| tcagagctca | aaaactgcgt | cttacagaca | gatggctttt | atgaatgtgt | tttccagcca | 1500 |
| atctttctat | tatctggcta | tacaatgtgg | atcaggatca | accattcttt | aggttcactt | 1560 |
| gactctccac | caacgtgtgt | ccttcctgac | tccgtagtaa | aaccactacc | tccatctaat | 1620 |
| gtaaaagcag | agattactat | aaacactgga | ttattgaaag | tatcttggga | aaagccagtc | 1680 |
| tttccagaga | ataaccttca | gttccagatt | cgatatggct | aaatggaaa | agaaatacaa | 1740 |
| tggaagacac | acgaggtatt | cgatgcaaaa | tcaaaatcgg | ccagcctgcc | agtgtcagat | 1800 |
| ctctgtgcgg | tctatgtggt | acaggttcgc | tgccggcggt | tggatggact | agggtattgg | 1860 |
| agtaattgga | gcagtccagc | ctacactctt | gtcatggatg | taaagttcc | tatgagaggg | 1920 |
| cctgaattct | ggagaataat | ggatggggat | attactaaaa | aggagagaaa | tgtcaccttg | 1980 |
| ctttggaagc | cactgatgaa | aaatgactca | ctgtgtagtg | tgaggaggta | tgtggtgaag | 2040 |
| catcgtactg | cccacaatgg | gacatggtca | caagatgtgg | gaaatcagac | caatctcact | 2100 |

-continued

```
ttcctgtggg cagaatcagc acacactgtt acagttctgg ccatcaattc catcggtgcc    2160
tcccttgtga attttaacct tacgttctca tggcccatga gtaaagtgaa tgctgtgcag    2220
tcactcagtg cttatcccct gagcagcagc tgcgtcatcc tttcctggac actgtcacct    2280
aatgattata gtctgttata tctggttatt gaatggaaga accttaatga tgatgatgga    2340
atgaagtggc ttagaatccc ttcgaatgtt aacaagtatt atatccatga taatttatt    2400 cctatcgaga aatatcagtt tagtctttac ccagtattta tggaaggagt tggaaaacca    2460
aagataatta atggtttcac caaagatgat atcgccaaac agcaaaatga tgcagggctg    2520
tatgtcattg taccgataat tatttcctct tgtgtcctgc tgctcggaac actgttaatt    2580
tcacaccaga gaatgaaaaa gttgttttgg gacgatgttc caaaccccaa gaattgttcc    2640
tgggcacaag gacttaattt ccaaaagcct gaaacatttg agcatctttt taccaagcat    2700
gcagaatcag tgatatttgg tcctcttctt ctggagcctg aaccagtttc agaagaaatc    2760
agtgtcgata cagcttggaa aaataaagat gagatggtac cagcagctat ggtctcactt    2820
cttttgacca ctccagattc cacaaggggt tctatttgta tcagtgacca gtgtaacagt    2880
gctaacttct ctggggctca gagcaccag ggaacctgtg aggatgagtg tcagagtcaa    2940
ccctcagtta aatatgcaac gctggtcagc aacgtgaaaa cagtggaaac tgatgaagag    3000 caagggcta acatagttc tgtcagccag tgcatcgcca ggaaacattc ccactgaga     3060 cagtcttttt ctagcaactc ctgggagata gaggcccagg catttttcct tttatcagat    3120
catccaccca atgtgatttc accacaactt tcattctcag ggttggatga gcttttggaa    3180
ctggagggaa attttcctga agaaaatcac ggggaaaaat ctgtgtatta tctaggagtc    3240
tcctcaggaa acaaaagaga gaatgatatg cttttgactg atgaggcagg ggtattgtgc    3300
ccattcccag ctcactgtct gttcagtgac atcagaatcc tccaggagag ttgttcacac    3360
tttgtagaaa ataatttgaa tttagggacc tctggtaaga actttgtacc ttacatgccc    3420
cagtttcaat cctgttccac tcacagtcat aagataatag aaaataagat gtgtgactta    3480
actgtgtaa                                                           3489
```

<210> SEQ ID NO 8
<211> LENGTH: 1162
<212> TYPE: PRT
<213> ORGANISM: Rattus norvegicus

<400> SEQUENCE: 8

```
Met Met Cys Gln Lys Phe Tyr Val Val Leu Leu His Trp Glu Phe Leu
1               5                   10                  15

Tyr Val Ile Thr Ala Leu Asn Leu Ala Tyr Pro Thr Ser Pro Trp Arg
            20                  25                  30

Phe Lys Leu Phe Cys Ala Pro Pro Ser Thr Thr Asp Asp Ser Phe Leu
        35                  40                  45

Ser Pro Ala Gly Val Pro Asn Asn Thr Ser Ser Leu Lys Gly Ala Ser
    50                  55                  60

Glu Ala Leu Val Glu Ala Lys Phe Asn Ser Thr Gly Ile Tyr Val Ser
65                  70                  75                  80

Glu Leu Ser Lys Thr Ile Phe His Cys Cys Phe Gly Asn Glu Gln Gly
                85                  90                  95

Gln Asn Cys Ser Ala Leu Thr Gly Asn Thr Glu Gly Lys Thr Leu Ala
            100                 105                 110

Ser Val Val Lys Pro Leu Val Phe Arg Gln Leu Gly Val Asn Trp Asp
        115                 120                 125
```

```
Ile Glu Cys Trp Met Lys Gly Asp Leu Thr Leu Phe Ile Cys His Met
130                 135                 140

Glu Pro Leu Leu Lys Asn Pro Phe Lys Asn Tyr Asp Ser Lys Val His
145                 150                 155                 160

Leu Leu Tyr Asp Leu Pro Glu Val Ile Asp Leu Pro Leu Pro Pro
            165                 170                 175

Leu Lys Asp Ser Phe Gln Thr Val Gln Cys Asn Cys Ser Val Arg Glu
            180                 185                 190

Cys Glu Cys His Val Pro Val Pro Arg Ala Lys Val Asn Tyr Ala Leu
            195                 200                 205

Leu Met Tyr Leu Glu Ile Thr Ser Ala Gly Val Ser Phe Gln Ser Pro
210                 215                 220

Leu Met Ser Leu Gln Pro Met Leu Val Val Lys Pro Asp Pro Pro Leu
225                 230                 235                 240

Gly Leu Arg Met Glu Val Thr Asp Asp Gly Asn Leu Lys Ile Ser Trp
                245                 250                 255

Asp Ser Gln Thr Lys Ala Pro Phe Pro Leu Gln Tyr Gln Val Lys Tyr
            260                 265                 270

Leu Glu Asn Ser Thr Ile Val Arg Glu Ala Ala Glu Ile Val Ser Asp
            275                 280                 285

Thr Ser Leu Leu Val Asp Ser Val Leu Pro Gly Ser Ser Tyr Glu Val
            290                 295                 300

Gln Val Arg Ser Lys Arg Leu Asp Gly Ser Gly Val Trp Ser Asp Trp
305                 310                 315                 320

Ser Leu Pro Gln Leu Phe Thr Thr Gln Asp Val Met Tyr Phe Pro Pro
                325                 330                 335

Lys Ile Leu Thr Ser Val Gly Ser Asn Ala Ser Phe Cys Cys Ile Tyr
                340                 345                 350

Lys Asn Glu Asn Gln Thr Ile Ser Ser Lys Gln Ile Val Trp Trp Met
                355                 360                 365

Asn Leu Ala Glu Lys Ile Pro Glu Thr Gln Tyr Asn Thr Val Ser Asp
370                 375                 380

His Ile Ser Lys Val Thr Phe Ser Asn Leu Lys Ala Thr Arg Pro Arg
385                 390                 395                 400

Gly Lys Phe Thr Tyr Asp Ala Val Tyr Cys Cys Asn Glu Gln Ala Cys
                405                 410                 415

His His Arg Tyr Ala Glu Leu Tyr Val Ile Asp Val Asn Ile Asn Ile
                420                 425                 430

Ser Cys Glu Thr Asp Gly Tyr Leu Thr Lys Met Thr Cys Arg Trp Ser
            435                 440                 445

Pro Ser Thr Ile Gln Ser Leu Val Gly Ser Thr Val Gln Leu Arg Tyr
    450                 455                 460

His Arg Arg Ser Leu Tyr Cys Pro Asp Asn Pro Ser Ile Arg Pro Thr
465                 470                 475                 480

Ser Glu Leu Lys Asn Cys Val Leu Gln Thr Asp Gly Phe Tyr Glu Cys
                485                 490                 495

Val Phe Gln Pro Ile Phe Leu Leu Ser Gly Tyr Thr Met Trp Ile Arg
            500                 505                 510

Ile Asn His Ser Leu Gly Ser Leu Asp Ser Pro Pro Thr Cys Val Leu
            515                 520                 525

Pro Asp Ser Val Val Lys Pro Leu Pro Pro Ser Asn Val Lys Ala Glu
530                 535                 540
```

```
Ile Thr Ile Asn Thr Gly Leu Leu Lys Val Ser Trp Glu Lys Pro Val
545                 550                 555                 560

Phe Pro Glu Asn Asn Leu Gln Phe Gln Ile Arg Tyr Gly Leu Asn Gly
                565                 570                 575

Lys Glu Ile Gln Trp Lys Thr His Glu Val Phe Asp Ala Lys Ser Lys
            580                 585                 590

Ser Ala Ser Leu Pro Val Ser Asp Leu Cys Ala Val Tyr Val Val Gln
        595                 600                 605

Val Arg Cys Arg Arg Leu Asp Gly Leu Gly Tyr Trp Ser Asn Trp Ser
    610                 615                 620

Ser Pro Ala Tyr Thr Leu Val Met Asp Val Lys Val Pro Met Arg Gly
625                 630                 635                 640

Pro Glu Phe Trp Arg Ile Met Asp Gly Asp Ile Thr Lys Lys Glu Arg
                645                 650                 655

Asn Val Thr Leu Leu Trp Lys Pro Leu Met Lys Asn Asp Ser Leu Cys
            660                 665                 670

Ser Val Arg Arg Tyr Val Val Lys His Arg Thr Ala His Asn Gly Thr
        675                 680                 685

Trp Ser Gln Asp Val Gly Asn Gln Thr Asn Leu Thr Phe Leu Trp Ala
    690                 695                 700

Glu Ser Ala His Thr Val Thr Val Leu Ala Ile Asn Ser Ile Gly Ala
705                 710                 715                 720

Ser Leu Val Asn Phe Asn Leu Thr Phe Ser Trp Pro Met Ser Lys Val
                725                 730                 735

Asn Ala Val Gln Ser Leu Ser Ala Tyr Pro Leu Ser Ser Ser Cys Val
            740                 745                 750

Ile Leu Ser Trp Thr Leu Ser Pro Asn Asp Tyr Ser Leu Leu Tyr Leu
        755                 760                 765

Val Ile Glu Trp Lys Asn Leu Asn Asp Asp Gly Met Lys Trp Leu
    770                 775                 780

Arg Ile Pro Ser Asn Val Asn Lys Tyr Tyr Ile His Asp Asn Phe Ile
785                 790                 795                 800

Pro Ile Glu Lys Tyr Gln Phe Ser Leu Tyr Pro Val Phe Met Glu Gly
                805                 810                 815

Val Gly Lys Pro Lys Ile Ile Asn Gly Phe Thr Lys Asp Asp Ile Ala
            820                 825                 830

Lys Gln Gln Asn Asp Ala Gly Leu Tyr Val Ile Val Pro Ile Ile Ile
        835                 840                 845

Ser Ser Cys Val Leu Leu Leu Gly Thr Leu Leu Ile Ser His Gln Arg
850                 855                 860

Met Lys Lys Leu Phe Trp Asp Asp Val Pro Asn Pro Lys Asn Cys Ser
865                 870                 875                 880

Trp Ala Gln Gly Leu Asn Phe Gln Lys Pro Glu Thr Phe Glu His Leu
                885                 890                 895

Phe Thr Lys His Ala Glu Ser Val Ile Phe Gly Pro Leu Leu Leu Glu
            900                 905                 910

Pro Glu Pro Val Ser Glu Glu Ile Ser Val Asp Thr Ala Trp Lys Asn
        915                 920                 925

Lys Asp Glu Met Val Pro Ala Ala Met Val Ser Leu Leu Leu Thr Thr
    930                 935                 940

Pro Asp Ser Thr Arg Gly Ser Ile Cys Ile Ser Asp Gln Cys Asn Ser
945                 950                 955                 960

Ala Asn Phe Ser Gly Ala Gln Ser Thr Gln Gly Thr Cys Glu Asp Glu
```

-continued

```
                     965             970              975
Cys Gln Ser Gln Pro Ser Val Lys Tyr Ala Thr Leu Val Ser Asn Val
            980             985              990
Lys Thr Val Glu Thr Asp Glu Glu Gln Gly Ala Ile His Ser Ser Val
            995             1000             1005
Ser Gln Cys Ile Ala Arg Lys His Ser Pro Leu Arg Gln Ser Phe
    1010            1015             1020
Ser Ser Asn Ser Trp Glu Ile Glu Ala Gln Ala Phe Phe Leu Leu
    1025            1030             1035
Ser Asp His Pro Pro Asn Val Ile Ser Pro Gln Leu Ser Phe Ser
    1040            1045             1050
Gly Leu Asp Glu Leu Leu Glu Leu Glu Gly Asn Phe Pro Glu Glu
    1055            1060             1065
Asn His Gly Glu Lys Ser Val Tyr Tyr Leu Gly Val Ser Ser Gly
    1070            1075             1080
Asn Lys Arg Glu Asn Asp Met Leu Leu Thr Asp Glu Ala Gly Val
    1085            1090             1095
Leu Cys Pro Phe Pro Ala His Cys Leu Phe Ser Asp Ile Arg Ile
    1100            1105             1110
Leu Gln Glu Ser Cys Ser His Phe Val Glu Asn Asn Leu Asn Leu
    1115            1120             1125
Gly Thr Ser Gly Lys Asn Phe Val Pro Tyr Met Pro Gln Phe Gln
    1130            1135             1140
Ser Cys Ser Thr His Ser His Lys Ile Ile Glu Asn Lys Met Cys
    1145            1150             1155
Asp Leu Thr Val
    1160
```

<210> SEQ ID NO 9
<211> LENGTH: 3800
<212> TYPE: DNA
<213> ORGANISM: Homo sapiens

<400> SEQUENCE: 9

```
ggcacgagcc ggtctggctt gggcaggctg cccgggccgt ggcaggaagc cggaagcagc      60
cgcggcccca gttcgggaga catggcgggc gttaaagctc tcgtggcatt atccttcagt     120
ggggctattg gactgacttt tcttatgctg ggatgtgcct tagaggatta tgggtgtact     180
tctctgaagt aagatgattt gtcaaaaatt ctgtgtggtt ttgttacatt gggaatttat     240
ttatgtgata actgcgttta acttgtcata tccaattact ccttggagat ttaagttgtc     300
ttgcatgcca ccaaattcaa cctatgacta cttcctttg cctgctggac tctcaaagaa     360
tacttcaaat tcgaatggac attatgagac agctgttgaa cctaagttta attcaagtgg     420
tactcacttt tctaacttat ccaaaacaac tttccactgt tgctttcgga gtgagcaaga     480
tagaaactgc tccttatgtg cagacaacat tgaaggaaag acatttgttt caacagtaaa     540
ttctttagtt tttcaacaaa tagatgcaaa ctggaacata cagtgctggc taaaaggaga     600
cttaaaatta ttcatctgtt atgtggagtc attatttaag aatctattca ggaattataa     660
ctataaggtc catctttat atgttctgcc tgaagtgtta aagattcac ctctggttcc      720
ccaaaaaggc agttttcaga tggttcactg caattgcagt gttcatgaat gttgtgaatg     780
tcttgtgcct gtgccaacag ccaaactcaa cgacactctc cttatgtgtt tgaaaatcac     840
atctggtgga gtaattttcc agtcacctct aatgtcagtt cagcccataa atatggtgaa     900
```

-continued

```
gcctgatcca ccattaggtt tgcatatgga aatcacagat gatggtaatt taaagatttc        960
ttggtccagc ccaccattgg taccatttcc acttcaatat caagtgaaat attcagagaa       1020
ttctacaaca gttatcagag aagctgacaa gattgtctca gctacatccc tgctagtaga       1080
cagtatactt cctgggtctt cgtatgaggt tcaggtgagg ggcaagagac tggatggccc       1140
aggaatctgg agtgactgga gtactcctcg tgtctttacc acacaagatg tcatatactt       1200
tccacctaaa attctgacaa gtgttgggtc taatgttttct tttcactgca tctataagaa       1260
ggaaaacaag attgttccct caaaagagat tgtttggtgg atgaatttag ctgagaaaat       1320
tcctcaaagc cagtatgatg ttgtgagtga tcatgttagc aaagttactt ttttcaatct       1380
gaatgaaacc aaacctcgag gaaagtttac ctatgatgca gtgtactgct gcaatgaaca       1440
tgaatgccat catcgctatg ctgaattata tgtgattgat gtcaatatca atatctcatg       1500
tgaaactgat gggtacttaa ctaaaatgac ttgcagatgg tcaaccagta caatccagtc       1560
acttgcggaa agcactttgc aattgaggta tcataggagc agcctttact gttctgatat       1620
tccatctatt catcccatat ctgagcccaa agattgctat tgcagagtg atggttttta       1680
tgaatgcatt ttccagccaa tcttcctatt atctggctac acaatgtgga ttaggatcaa       1740
tcactctcta ggttcacttg actctccacc aacatgtgtc cttcctgatt ctgtggtgaa       1800
gccactgcct ccatccagtg tgaaagcaga aattactata acattggat tattgaaaat        1860
atcttgggaa aagccagtct ttccagagaa taaccttcaa ttccagattc gctatggttt       1920
aagtggaaaa gaagtacaat ggaagatgta tgaggtttat gatgcaaaat caaaatctgt       1980
cagtctccca gttccagact tgtgtgcagt ctatgctgtt caggtgcgct gtaagaggct       2040
agatggactg ggatattgga gtaattggag caatccagcc tacacagttg tcatggatat       2100
aaaagttcct atgagaggac ctgaattttg gagaataatt aatggagata ctatgaaaaa       2160
ggagaaaaat gtcactttac tttggaagcc cctgatgaaa aatgactcat tgtgcagtgt       2220
tcagagatat gtgataaacc atcatacttc ctgcaatgga acatggtcag aagatgtggg       2280
aaatcacacg aaattcactt tcctgtggac agagcaagca catactgtta cggttctggc       2340
catcaattca attggtgctt ctgttgcaaa ttttaattta accttttcat ggcctatgag       2400
caaagtaaat atcgtgcagt cactcagtgc ttatccttta aacagcagtt gtgtgattgt       2460
ttcctggata ctatcaccca gtgattacaa gctaatgtat tttattattg agtggaaaaa       2520
tcttaatgaa gatggtgaaa taaaatggct tagaatctct tcatctgtta agaagtatta       2580
tatccatgat cattttatcc ccattgagaa gtaccagttc agtctttacc caatatttat       2640
ggaaggagtg ggaaaaccaa agataattaa tagtttcact caagatgata ttgaaaaaca       2700
ccagagtgat gcaggtttat atgtaattgt gccagtaatt atttcctctt ccatcttatt       2760
gcttggaaca ttattaatat cacaccaaag aatgaaaaag ctattttggg aagatgttcc       2820
gaaccccaag aattgttcct gggcacaagg acttaatttt cagaagccag aaacgtttga       2880
gcatcttttt atcaagcata cagcatcagt gacatgtggt cctcttcttt tggagcctga       2940
aacaatttca gaagatatca gtgttgatac atcatgaaa aataaagatg agatgatgcc       3000
aacaactgtg gtctctctac tttcaacaac agatcttgaa aagggttctg tttgtattag       3060
tgaccagttc aacagtgtta acttctctga ggctgagggt actgaggtaa cctatgaggc       3120
cgaaagccag agacaaccct tgttaaata cgccacgctg atcagcaact ctaaaccaag       3180
tgaaactggt gaagaacaag ggcttataaa tagttcagtc accaagtgct tctctagcaa       3240
aaattctccg ttgaaggatt cttttctctaa tagctcatgg gagatagagg cccaggcatt       3300
```

-continued

```
ttttatatta tcagatcagc atcccaacat aatttcacca cacctcacat tctcagaagg    3360
attggatgaa cttttgaaat tggagggaaa tttccctgaa gaaataatg ataaaaagtc     3420 tatctattat ttaggggtca cctcaatcaa aagagagag agtggtgtgc ttttgactga     3480
caagtcaagg gtatcgtgcc cattcccagc ccctgttta ttcacggaca tcagagttct     3540
ccaggacagt tgctcacact ttgtagaaaa taatatcaac ttaggaactt ctagtaagaa    3600
gacttttgca tcttacatgc ctcaattcca aacttgttct actcagactc ataagatcat    3660
ggaaaacaag atgtgtgacc taactgtgta atttcactga agaaaccttc agatttgtgt    3720
tataatgggt aatataaagt gtaatagatt atagttgtgg gtgggagaga gaaaagaaac    3780
cagagtccaa atttgaaaat                                                3800
```

<210> SEQ ID NO 10
<211> LENGTH: 1165
<212> TYPE: PRT
<213> ORGANISM: Homo sapiens

<400> SEQUENCE: 10

```
Met Ile Cys Gln Lys Phe Cys Val Val Leu Leu His Trp Glu Phe Ile
1               5                   10                  15

Tyr Val Ile Thr Ala Phe Asn Leu Ser Tyr Pro Ile Thr Pro Trp Arg
            20                  25                  30

Phe Lys Leu Ser Cys Met Pro Pro Asn Ser Thr Tyr Asp Tyr Phe Leu
        35                  40                  45

Leu Pro Ala Gly Leu Ser Lys Asn Thr Ser Asn Ser Asn Gly His Tyr
    50                  55                  60

Glu Thr Ala Val Glu Pro Lys Phe Asn Ser Ser Gly Thr His Phe Ser
65                  70                  75                  80

Asn Leu Ser Lys Thr Thr Phe His Cys Cys Phe Arg Ser Glu Gln Asp
                85                  90                  95

Arg Asn Cys Ser Leu Cys Ala Asp Asn Ile Glu Gly Lys Thr Phe Val
            100                 105                 110

Ser Thr Val Asn Ser Leu Val Phe Gln Gln Ile Asp Ala Asn Trp Asn
        115                 120                 125

Ile Gln Cys Trp Leu Lys Gly Asp Leu Lys Leu Phe Ile Cys Tyr Val
    130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
        195                 200                 205

Leu Leu Met Cys Leu Lys Ile Thr Ser Gly Gly Val Ile Phe Gln Ser
    210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
                245                 250                 255

Trp Ser Ser Pro Pro Leu Val Pro Phe Pro Leu Gln Tyr Gln Val Lys
            260                 265                 270

Tyr Ser Glu Asn Ser Thr Thr Val Ile Arg Glu Ala Asp Lys Ile Val
```

-continued

```
                275                 280                 285
Ser Ala Thr Ser Leu Leu Val Asp Ser Ile Leu Pro Gly Ser Ser Tyr
290                 295                 300

Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
                325                 330                 335

Pro Pro Lys Ile Leu Thr Ser Val Gly Ser Asn Val Ser Phe His Cys
                340                 345                 350

Ile Tyr Lys Lys Glu Asn Lys Ile Val Pro Ser Lys Glu Ile Val Trp
                355                 360                 365

Trp Met Asn Leu Ala Glu Lys Ile Pro Gln Ser Gln Tyr Asp Val Val
370                 375                 380

Ser Asp His Val Ser Lys Val Thr Phe Phe Asn Leu Asn Glu Thr Lys
385                 390                 395                 400

Pro Arg Gly Lys Phe Thr Tyr Asp Ala Val Tyr Cys Cys Asn Glu His
                405                 410                 415

Glu Cys His His Arg Tyr Ala Glu Leu Tyr Val Ile Asp Val Asn Ile
                420                 425                 430

Asn Ile Ser Cys Glu Thr Asp Gly Tyr Leu Thr Lys Met Thr Cys Arg
                435                 440                 445

Trp Ser Thr Ser Thr Ile Gln Ser Leu Ala Glu Ser Thr Leu Gln Leu
450                 455                 460

Arg Tyr His Arg Ser Ser Leu Tyr Cys Ser Asp Ile Pro Ser Ile His
465                 470                 475                 480

Pro Ile Ser Glu Pro Lys Asp Cys Tyr Leu Gln Ser Asp Gly Phe Tyr
                485                 490                 495

Glu Cys Ile Phe Gln Pro Ile Phe Leu Leu Ser Gly Tyr Thr Met Trp
                500                 505                 510

Ile Arg Ile Asn His Ser Leu Gly Ser Leu Asp Ser Pro Pro Thr Cys
                515                 520                 525

Val Leu Pro Asp Ser Val Val Lys Pro Leu Pro Pro Ser Ser Val Lys
530                 535                 540

Ala Glu Ile Thr Ile Asn Ile Gly Leu Leu Lys Ile Ser Trp Glu Lys
545                 550                 555                 560

Pro Val Phe Pro Glu Asn Asn Leu Gln Phe Gln Ile Arg Tyr Gly Leu
                565                 570                 575

Ser Gly Lys Glu Val Gln Trp Lys Met Tyr Glu Val Tyr Asp Ala Lys
                580                 585                 590

Ser Lys Ser Val Ser Leu Pro Val Pro Asp Leu Cys Ala Val Tyr Ala
                595                 600                 605

Val Gln Val Arg Cys Lys Arg Leu Asp Gly Leu Gly Tyr Trp Ser Asn
610                 615                 620

Trp Ser Asn Pro Ala Tyr Thr Val Val Met Asp Ile Lys Val Pro Met
625                 630                 635                 640

Arg Gly Pro Glu Phe Trp Arg Ile Ile Asn Gly Asp Thr Met Lys Lys
                645                 650                 655

Glu Lys Asn Val Thr Leu Leu Trp Lys Pro Leu Met Lys Asn Asp Ser
                660                 665                 670

Leu Cys Ser Val Gln Arg Tyr Val Ile Asn His His Thr Ser Cys Asn
                675                 680                 685

Gly Thr Trp Ser Glu Asp Val Gly Asn His Thr Lys Phe Thr Phe Leu
                690                 695                 700
```

-continued

```
Trp Thr Glu Gln Ala His Thr Val Thr Val Leu Ala Ile Asn Ser Ile
705                 710                 715                 720

Gly Ala Ser Val Ala Asn Phe Asn Leu Thr Phe Ser Trp Pro Met Ser
            725                 730                 735

Lys Val Asn Ile Val Gln Ser Leu Ser Ala Tyr Pro Leu Asn Ser Ser
            740                 745                 750

Cys Val Ile Val Ser Trp Ile Leu Ser Pro Ser Asp Tyr Lys Leu Met
            755                 760                 765

Tyr Phe Ile Ile Glu Trp Lys Asn Leu Asn Glu Asp Gly Glu Ile Lys
        770                 775                 780

Trp Leu Arg Ile Ser Ser Val Lys Lys Tyr Tyr Ile His Asp His
785                 790                 795                 800

Phe Ile Pro Ile Glu Lys Tyr Gln Phe Ser Leu Tyr Pro Ile Phe Met
                805                 810                 815

Glu Gly Val Gly Lys Pro Lys Ile Ile Asn Ser Phe Thr Gln Asp Asp
            820                 825                 830

Ile Glu Lys His Gln Ser Asp Ala Gly Leu Tyr Val Ile Val Pro Val
        835                 840                 845

Ile Ile Ser Ser Ser Ile Leu Leu Leu Gly Thr Leu Leu Ile Ser His
850                 855                 860

Gln Arg Met Lys Lys Leu Phe Trp Glu Asp Val Pro Asn Pro Lys Asn
865                 870                 875                 880

Cys Ser Trp Ala Gln Gly Leu Asn Phe Gln Lys Pro Glu Thr Phe Glu
            885                 890                 895

His Leu Phe Ile Lys His Thr Ala Ser Val Thr Cys Gly Pro Leu Leu
            900                 905                 910

Leu Glu Pro Glu Thr Ile Ser Glu Asp Ile Ser Val Asp Thr Ser Trp
            915                 920                 925

Lys Asn Lys Asp Glu Met Met Pro Thr Thr Val Val Ser Leu Leu Ser
930                 935                 940

Thr Thr Asp Leu Glu Lys Gly Ser Val Cys Ile Ser Asp Gln Phe Asn
945                 950                 955                 960

Ser Val Asn Phe Ser Glu Ala Glu Gly Thr Glu Val Thr Tyr Glu Ala
            965                 970                 975

Glu Ser Gln Arg Gln Pro Phe Val Lys Tyr Ala Thr Leu Ile Ser Asn
            980                 985                 990

Ser Lys Pro Ser Glu Thr Gly Glu  Glu Gln Gly Leu Ile  Asn Ser Ser
            995                 1000                1005

Val Thr Lys Cys Phe Ser Ser  Lys Asn Ser Pro Leu  Lys Asp Ser
    1010                1015                1020

Phe Ser  Asn Ser Ser Trp Glu  Ile Glu Ala Gln Ala  Phe Phe Ile
    1025                1030                1035

Leu Ser  Asp Gln His Pro Asn  Ile Ile Ser Pro His  Leu Thr Phe
    1040                1045                1050

Ser Glu  Gly Leu Asp Glu Leu  Leu Lys Leu Glu Gly  Asn Phe Pro
    1055                1060                1065

Glu Glu  Asn Asn Asp Lys Lys  Ser Ile Tyr Tyr Leu  Gly Val Thr
    1070                1075                1080

Ser Ile  Lys Lys Arg Glu Ser  Gly Val Leu Leu Thr  Asp Lys Ser
    1085                1090                1095

Arg Val  Ser Cys Pro Phe Pro  Ala Pro Cys Leu Phe  Thr Asp Ile
    1100                1105                1110
```

```
Arg Val Leu Gln Asp Ser Cys Ser His Phe Val Glu Asn Asn Ile
    1115                1120                1125

Asn Leu Gly Thr Ser Ser Lys Lys Thr Phe Ala Ser Tyr Met Pro
    1130                1135                1140

Gln Phe Gln Thr Cys Ser Thr Gln Thr His Lys Ile Met Glu Asn
    1145                1150                1155

Lys Met Cys Asp Leu Thr Val
    1160                1165

<210> SEQ ID NO 11
<211> LENGTH: 504
<212> TYPE: DNA
<213> ORGANISM: Sus scrofa

<400> SEQUENCE: 11
atgcgctgtg gacccctgtg ccgattcctg tggctttggc cctatctgtc ctacgttgaa      60
gccgtgccca tctggagagt ccaggatgac accaaaaccc tcatcaagac gattgtcacc     120
aggatcagtg acatttcaca catgcagtct gtctcctcca acagagggt caccggtttg      180 gacttcatcc ctgggctcca tcctgtcctg agtttgtcca agatggacca gaccctggcg     240
atctaccaac agatcctcac cagtctgcct tccagaaatg tgatccaaat atcgaatgac     300
ctggagaacc tccgggacct tctccacctg ctggcctcct ccaagagctg ccccttgccc     360
caggccaggg ccctggagac cttggagagc ctgggcggcg tcctggaagc ctccctctac     420
tccacggagg tggtggccct gagcaggctg caggggctc tgcaggacat gctgcggcag      480
ctggacctca gccctggctg ctga                                             504

<210> SEQ ID NO 12
<211> LENGTH: 167
<212> TYPE: PRT
<213> ORGANISM: Sus scrofa

<400> SEQUENCE: 12

Met Arg Cys Gly Pro Leu Cys Arg Phe Leu Trp Leu Trp Pro Tyr Leu
1               5                   10                  15

Ser Tyr Val Glu Ala Val Pro Ile Trp Arg Val Gln Asp Asp Thr Lys
            20                  25                  30

Thr Leu Ile Lys Thr Ile Val Thr Arg Ile Ser Asp Ile Ser His Met
        35                  40                  45

Gln Ser Val Ser Ser Lys Gln Arg Val Thr Gly Leu Asp Phe Ile Pro
    50                  55                  60

Gly Leu His Pro Val Leu Ser Leu Ser Lys Met Asp Gln Thr Leu Ala
65                  70                  75                  80

Ile Tyr Gln Gln Ile Leu Thr Ser Leu Pro Ser Arg Asn Val Ile Gln
                85                  90                  95

Ile Ser Asn Asp Leu Glu Asn Leu Arg Asp Leu Leu His Leu Leu Ala
            100                 105                 110

Ser Ser Lys Ser Cys Pro Leu Pro Gln Ala Arg Ala Leu Glu Thr Leu
        115                 120                 125

Glu Ser Leu Gly Gly Val Leu Glu Ala Ser Leu Tyr Ser Thr Glu Val
    130                 135                 140

Val Ala Leu Ser Arg Leu Gln Gly Ala Leu Gln Asp Met Leu Arg Gln
145                 150                 155                 160

Leu Asp Leu Ser Pro Gly Cys
                165
```

<210> SEQ ID NO 13
<211> LENGTH: 1413
<212> TYPE: DNA
<213> ORGANISM: Mus musculus
<220> FEATURE:
<221> NAME/KEY: misc_feature
<222> LOCATION: (1216)..(1216)
<223> OTHER INFORMATION: "n" can be either "a", "c", "t", or "g"

<400> SEQUENCE: 13

```
cccgtgtgtt tgtgttcata gcatttgaag aactcaagcc tgggagtttt tcttgtctaa      60
cttttgaaaaa ctgagactgc ctctcccttg tgatttttga tattccaagt ttccagtcac     120
caactgtgtc atttggggtt gactgatgta ccttgctttg aaccttacac actgcctttc     180
tgcaaatgtg actgaatgaa gatgtaaata ctgagcatta aaatgtgtct tttcttttag     240
cctgaaacat ttgagcatct ttttaccaag catgcagaat cagtgatatt tggtcctctt     300
cttctggagc ctgaacccat ttcagaagaa atcagtgtcg atacagcttg gaaaaataaa     360
gatgagatgg tcccagcagc tatggtctcc cttcttttga ccacaccaga ccctgaaagc     420
agttctattt gtattagtga ccagtgtaac agtgctaact tctctgggtc tcagagcacc     480
caggtaaacct gtgaggatga gtgtcagaga caaccctcag ttaaatatgc aactctggtc     540
agcaacgata aactagtgga aactgatgaa gagcaagggt ttatccatag tcctgtcagc     600
aactgcatct ccagtaatca ttccccactg aggcagtctt tctctagcag ctcctgggag     660
acagaggccc agacattttt ccttttatca gaccagcaac ccaccatgat tcaccacaa      720
ctttcattct cggggttgga tgagcttttg gaactggagg gaagttttcc tgaagaaaat     780
cacagggaga agtctgtctg ttatctagga gtcacctccg tcaacagaag agagagtggt     840
gtgcttttga ctggtgaggc aggaatcctg tgcacattcc cagcccagtg tctgttcagt     900
gacatcagga tcctccagga gagatgctca cactttgtag aaaataattt gagtttaggg     960
acctctggtg agaactttgt accttacatg ccccaatttc aaacctgttc cacgcacagt    1020
cacaagataa tggagaataa gatgtgtgac ttaactgtgc aatctcatcc aaaaagcctc    1080
aaggttccgt tccagtagag tgtgtcatgt ataatgtgtt cttttattgt tgtggatgtg    1140
ggagacaagt gtcagaatct agtgtgaaaa tgattgtttc caaactaagt gtgtctattt    1200
tctctcagta atacanatga aacatatgag gaagccctca ttaatctagt aatgtagatg    1260
gactcttact gaatatattc ccaagatact tggggaagtc tccctaattc tagctaaaaa    1320
taaacccagg aagtagaatc tataaactct gaactctgtg gaaagaagaa atttcaacac    1380
gatattgaca gctgaacaaa aaggtttcaa gct                                 1413
```

<210> SEQ ID NO 14
<211> LENGTH: 1174
<212> TYPE: PRT
<213> ORGANISM: Mus musculus

<400> SEQUENCE: 14

Met Met Cys Gln Lys Phe Tyr Val Val Leu Leu His Trp Glu Phe Leu
1               5                   10                  15

Tyr Val Ile Ala Ala Leu Asn Leu Ala Tyr Pro Ile Ser Pro Trp Lys
            20                  25                  30

Phe Lys Leu Phe Cys Gly Pro Pro Asn Thr Thr Asp Asp Ser Phe Leu
        35                  40                  45

Ser Pro Ala Gly Ala Pro Asn Asn Ala Ser Ala Leu Lys Gly Ala Ser
    50                  55                  60

-continued

```
Glu Ala Ile Val Glu Ala Lys Phe Asn Ser Ser Gly Ile Tyr Val Pro
65                  70                  75                  80

Glu Leu Ser Lys Thr Val Phe His Cys Cys Phe Gly Asn Glu Gln Gly
                85                  90                  95

Gln Asn Cys Ser Ala Leu Thr Asp Asn Thr Glu Gly Lys Thr Leu Ala
            100                 105                 110

Ser Val Val Lys Ala Ser Val Phe Arg Gln Leu Gly Val Asn Trp Asp
        115                 120                 125

Ile Glu Cys Trp Met Lys Gly Asp Leu Thr Leu Phe Ile Cys His Met
    130                 135                 140

Glu Pro Leu Pro Lys Asn Pro Phe Lys Asn Tyr Asp Ser Lys Val His
145                 150                 155                 160

Leu Leu Tyr Asp Leu Pro Glu Val Ile Asp Asp Ser Pro Leu Pro Pro
                165                 170                 175

Leu Lys Asp Ser Phe Gln Thr Val Gln Cys Asn Cys Ser Leu Arg Gly
            180                 185                 190

Cys Glu Cys His Val Pro Val Pro Arg Ala Lys Leu Asn Tyr Ala Leu
        195                 200                 205

Leu Met Tyr Leu Glu Ile Thr Ser Ala Gly Val Ser Phe Gln Ser Pro
210                 215                 220

Leu Met Ser Leu Gln Pro Met Leu Val Val Lys Pro Asp Pro Pro Leu
225                 230                 235                 240

Gly Leu His Met Glu Val Thr Asp Asp Gly Asn Leu Lys Ile Ser Trp
                245                 250                 255

Asp Ser Gln Thr Met Ala Pro Phe Pro Leu Gln Tyr Gln Val Lys Tyr
            260                 265                 270

Leu Glu Asn Ser Thr Ile Val Arg Glu Ala Ala Glu Ile Val Ser Ala
        275                 280                 285

Thr Ser Leu Leu Val Asp Ser Val Leu Pro Gly Ser Ser Tyr Glu Val
    290                 295                 300

Gln Val Arg Ser Lys Arg Leu Asp Gly Ser Gly Val Trp Ser Asp Trp
305                 310                 315                 320

Ser Ser Pro Gln Val Phe Thr Thr Gln Asp Val Val Tyr Phe Pro Pro
                325                 330                 335

Lys Ile Leu Thr Ser Val Gly Ser Asn Ala Ser Phe His Cys Ile Tyr
            340                 345                 350

Lys Asn Glu Asn Gln Ile Ile Ser Ser Lys Gln Ile Val Trp Trp Arg
        355                 360                 365

Asn Leu Ala Glu Lys Ile Pro Glu Ile Gln Tyr Ser Ile Val Ser Asp
370                 375                 380

Arg Val Ser Lys Val Thr Phe Ser Asn Leu Lys Ala Thr Arg Pro Arg
385                 390                 395                 400

Gly Lys Phe Thr Tyr Asp Ala Val Tyr Cys Cys Asn Glu Gln Ala Cys
                405                 410                 415

His His Arg Tyr Ala Glu Leu Tyr Val Ile Asp Val Asn Ile Asn Ile
            420                 425                 430

Ser Cys Glu Thr Asp Gly Tyr Leu Thr Lys Met Thr Cys Arg Trp Ser
        435                 440                 445

Pro Ser Thr Ile Gln Ser Leu Val Gly Ser Thr Val Gln Leu Arg Tyr
    450                 455                 460

His Arg Arg Ser Leu Tyr Cys Pro Asp Ser Pro Ser Ile His Pro Thr
465                 470                 475                 480
```

```
Ser Glu Pro Lys Asn Cys Val Leu Gln Arg Asp Gly Phe Tyr Glu Cys
            485                 490                 495

Val Phe Gln Pro Ile Phe Leu Leu Ser Gly Tyr Thr Met Trp Ile Arg
            500                 505                 510

Ile Asn His Ser Leu Gly Ser Leu Asp Ser Pro Pro Thr Cys Val Leu
            515                 520                 525

Pro Asp Ser Val Val Lys Pro Leu Pro Pro Ser Asn Val Lys Ala Glu
            530                 535                 540

Ile Thr Val Asn Thr Gly Leu Leu Lys Val Ser Trp Glu Lys Pro Val
545                 550                 555                 560

Phe Pro Glu Asn Asn Leu Gln Phe Gln Ile Arg Tyr Gly Leu Ser Gly
            565                 570                 575

Lys Glu Ile Gln Trp Lys Thr His Glu Val Phe Asp Ala Lys Ser Lys
            580                 585                 590

Ser Ala Ser Leu Leu Val Ser Asp Leu Cys Ala Val Tyr Val Val Gln
            595                 600                 605

Val Arg Cys Arg Arg Leu Asp Gly Leu Gly Tyr Trp Ser Asn Trp Ser
610                 615                 620

Ser Pro Ala Tyr Thr Leu Val Met Asp Val Lys Val Pro Met Arg Gly
625                 630                 635                 640

Pro Glu Phe Trp Arg Lys Met Asp Gly Asp Val Thr Lys Lys Glu Arg
            645                 650                 655

Asn Val Thr Leu Leu Trp Lys Pro Leu Thr Lys Asn Asp Ser Leu Cys
            660                 665                 670

Ser Val Arg Arg Tyr Val Val Lys His Arg Thr Ala His Asn Gly Thr
            675                 680                 685

Trp Ser Glu Asp Val Gly Asn Arg Thr Asn Leu Thr Phe Leu Trp Thr
690                 695                 700

Glu Pro Ala His Thr Val Thr Val Leu Ala Val Asn Ser Leu Gly Ala
705                 710                 715                 720

Ser Leu Val Asn Phe Asn Leu Thr Phe Ser Trp Pro Met Ser Lys Val
            725                 730                 735

Ser Ala Val Glu Ser Leu Ser Ala Tyr Pro Leu Ser Ser Ser Cys Val
            740                 745                 750

Ile Leu Ser Trp Thr Leu Ser Pro Asp Asp Tyr Ser Leu Leu Tyr Leu
            755                 760                 765

Val Ile Glu Trp Lys Ile Leu Asn Glu Asp Asp Gly Met Lys Trp Leu
770                 775                 780

Arg Ile Pro Ser Asn Val Lys Lys Phe Tyr Ile His Asp Asn Phe Ile
785                 790                 795                 800

Pro Ile Glu Lys Tyr Gln Phe Ser Leu Tyr Pro Val Phe Met Glu Gly
            805                 810                 815

Val Gly Lys Pro Lys Ile Ile Asn Gly Phe Thr Lys Asp Ala Ile Asp
            820                 825                 830

Lys Gln Gln Asn Asp Ala Gly Leu Tyr Val Ile Val Pro Ile Ile Ile
            835                 840                 845

Ser Ser Cys Val Leu Leu Gly Thr Leu Leu Ile Ser His Gln Arg
            850                 855                 860

Met Lys Lys Leu Phe Trp Asp Asp Val Pro Asn Pro Lys Asn Cys Ser
865                 870                 875                 880

Trp Ala Gln Gly Leu Asn Phe Gln Lys Pro Glu Thr Phe Glu His Leu
            885                 890                 895

Phe Thr Lys His Ala Glu Ser Val Ile Phe Gly Pro Leu Leu Leu Glu
```

-continued

```
                900             905             910
Pro Glu Pro Ile Ser Glu Ile Ser Val Asp Thr Ala Trp Lys Asn
        915                 920                 925
Lys Asp Glu Met Val Pro Ala Ala Met Val Ser Leu Leu Thr Thr
        930                 935                 940
Pro Asp Pro Glu Ser Ser Ile Cys Ile Ser Asp Gln Cys Asn Ser
945                 950                 955                 960
Ala Asn Phe Ser Gly Ser Gln Ser Thr Gln Val Thr Cys Glu Asp Glu
                965                 970                 975
Cys Gln Arg Gln Pro Ser Val Lys Tyr Ala Thr Leu Val Ser Asn Asp
            980                 985                 990
Lys Leu Val Glu Thr Asp Glu Glu Gln Gly Phe Ile His Ser Pro Val
            995                 1000                1005
Ser Asn Cys Ile Ser Ser Asn His Ser Pro Leu Arg Gln Ser Phe
    1010                1015                1020
Ser Ser Ser Ser Trp Glu Thr Glu Ala Gln Thr Phe Phe Leu Leu
    1025                1030                1035
Ser Asp Gln Gln Pro Thr Met Ile Ser Pro Gln Leu Ser Phe Ser
    1040                1045                1050
Gly Leu Asp Glu Leu Leu Glu Leu Glu Gly Ser Phe Pro Glu Glu
    1055                1060                1065
Asn His Arg Glu Lys Ser Val Cys Tyr Leu Gly Val Thr Ser Val
    1070                1075                1080
Asn Arg Arg Glu Ser Gly Val Leu Leu Thr Gly Glu Ala Gly Ile
    1085                1090                1095
Leu Cys Thr Phe Pro Ala Gln Cys Leu Phe Ser Asp Ile Arg Ile
    1100                1105                1110
Leu Gln Glu Arg Cys Ser His Phe Val Glu Asn Asn Leu Ser Leu
    1115                1120                1125
Gly Thr Ser Gly Glu Asn Phe Val Pro Tyr Met Pro Gln Phe Gln
    1130                1135                1140
Thr Cys Ser Thr His Ser His Lys Ile Met Glu Asn Lys Met Cys
    1145                1150                1155
Asp Leu Thr Val Gln Ser His Pro Lys Ser Leu Lys Val Pro Phe
    1160                1165                1170
Gln
```

```
<210> SEQ ID NO 15
<211> LENGTH: 4067
<212> TYPE: DNA
<213> ORGANISM: Bos taurus

<400> SEQUENCE: 15
gaattcacgg ttccatgact ttggagtttc agacatcctg agtgaacacg gtaggctgag     60
agtgtatgtg ctctctctgg ccttcaggtc tttgtaccag ctgctctctt ggccacttat    120
ggcaaccact tgtattcttc caagacctcc ccttcgcctt caatacccag ctcaggcgac    180
acctcttctc agggaggcca ctttgtaatc ctgcaatatc ttgtccttct tgcagagctc    240
tttcttaaaa aaaaaaaaaa aatatatata tatatatata taatttattt ttaattgaag    300
ggtaattgct ttacaatatt gtgttggttt cagccatact tgcagagctc tttcctcctg    360
tactgctacg gcctgtttac tatctcccct attaaactgg aaacactttg agagtaaaaa    420
aacatccgtt gttcactgtg gcatccttgg tgcccagcac tgcgtctgat tatcagacct    480
```

| | |
|---|---|
| tctgtaagtg cccgtcggag tcaggctccc aatgggagag aaaggaagca ataaagccag | 540 |
| tggtaaatgc catcacggag gtatcagtgc gctgctgtga gagagtaatg aagaggacag | 600 |
| tcacataaac tctaataata gggtagtaat agagaaccct tcacaactcc tttaaagctc | 660 |
| tttcacgcac attatctaat ttgatcctca taaaaccctg gagataggta cattgtgggg | 720 |
| gatacagggg gagtttttag cggttatggg atatgcctgc agtcgtacag ctattaaatg | 780 |
| tctggattca aaccagacct tgaaagcccg ccgtccaccc gctcgtgccc tggctcactg | 840 |
| ctgcgtggtc tacagcacac ctcctgtggt tttcttgatt ccgccgcacc tctccccagg | 900 |
| gagtgccttt cattactgtc atttctagac aatgaattgt ctttgaggag atgatagcca | 960 |
| tggcagacag caaatctcgt tgttatccgc atctgaagac gtggatgcgg gtggtaacgg | 1020 |
| agcacgtggg tgttctcgga gatcgacgat gtgccacgtg tggtttcttc tgttttcagg | 1080 |
| ccccagaagc ccatcccggg aaggaaaatg cgctgtggac ccctgtatcg attcctgtgg | 1140 |
| ctttggccct atctgtctta cgtggaggct gtgcccatcc gcaaggtcca ggatgacacc | 1200 |
| aaaaccctca tcaagacaat tgtcaccagg atcaatgaca tctcacacac ggtagggagg | 1260 |
| gactgggaga cgaggtagaa ccgtggccat cccgtggggg accccagagg ctggcggagg | 1320 |
| aggctgtgca gccttgcaca ggccccagtg gcctggacgc cccctggca taaagacagc | 1380 |
| tcctctcctc ctctacttcc cttgcctcct gccttctcac tctcctccct cccagaccgg | 1440 |
| aatcctagtg cccaggccca gaaggagtca cagaggtcct ggggtcccct tggcaggtgg | 1500 |
| ccagaacccc agcagcagtc cctctgggcc tccatctcat ttctagaatg ttttagtcgt | 1560 |
| taggcattct tcctgcctgg taactgagct tagaccctgc gagctcatta ctcattactg | 1620 |
| ccagccctgc ctgtcaagcc ctcttcagat acaaccctct gtgttttgt aaatagttat | 1680 |
| cagtgtctct tggggcattt tttctgaggt ccataagctc agacctgcaa ccatagatga | 1740 |
| ggtctgtatt tagaatgagg gagatgtctg taaagtctta agctagtcag gttccacaag | 1800 |
| gttttttaaac tccagtttcc tcatctagaa aatgaaagtg ggaaagtgtt agttgctcag | 1860 |
| tcatgtccaa ctctttgaga ccccatgaac tgtagtctac caggctcctc tgtccatgaa | 1920 |
| attcttcagg caagaatact ggagtggctt gttatttttct tctcccaaca agatcttccc | 1980 |
| aacccaggga ttgaacctgg gtcttctaaa ttgcaggcag attctttacc gtctgagcca | 2040 |
| ccagggaaac ccataagacc ttgtgaagac tattaagata gtcatctaga caacaagact | 2100 |
| atcttaatag tcttcataag gtcttcatga gactaaatta gataaagcaa gtgaccctcc | 2160 |
| ctgaataccc ttgcagaacc agaactgtgt gtgccctctt tcaaggtttt cagtcatgac | 2220 |
| ttttgatagc ttcccaccett aaaagccaac ttgctcacct gcgtggagca atctggagac | 2280 |
| ttccacatct cctgaccact ctatatttct aacagtggct ttgggaagcc agagagcagt | 2340 |
| taggtagcca gaagcgggga cagatcagaa atagacagtg tctgcatttc ctagagaaaa | 2400 |
| gcccttaaat tcattgcttt caaaacagtc attcagcaag ctgtacacaa tagacccaga | 2460 |
| gtgccccaac ctgtgtggtg ccgggattga ttgctgtggg tggcggagag gggagagccc | 2520 |
| ctctggtaac cagggttact tgagcagagc agtgagctgg ggcatcgctg gggtaatggc | 2580 |
| ctgaatccct taggggtgta gacttcctgg agaatctgac tgtgagggag gagtctgctt | 2640 |
| ggggtggaag agttggggac ggggaatgta cggaagacct caatgcctgg ggaagaaact | 2700 |
| caagcaggaa atagggagtc atggctggtt ctatagcaga gtcatttgga aaagggaaca | 2760 |
| gcctgcaaag gctggtctgg aggcaaaggg cagggtggtt tgggaagggc agaaagatag | 2820 |
| gagcccagga gaccagcttg gaaacatggt ggtcacgtgg gcacaagaag taagggccca | 2880 |

```
gggaggatgg tgtggaagcg ggggaggaag cacctctacg ctctagggaa aggcggagtc    2940 agggagctc tgaggagctg ccctctctcc cactgagctc ttgctctccc cttcctcctg    3000
catagcagtc cgtctcctcc aaacagaggg tcactggttt ggacttcatc cctgggctcc    3060
accctctcct gagtttgtcc aagatggacc agacattggc gatctaccaa cagatcctca    3120
ccagtctgcc ttccagaaat gtggtccaaa tatccaatga cctggagaac ctccgggacc    3180
ttctccacct gctggccgcc tccaagagct gccccttgcc gcaggtcagg gccctggaga    3240
gcttggagag cttgggcgtt gtcctggaag cttccctcta ctccaccgag gtggtggccc    3300
tgagccggct gcagggtca ctacaggaca tgttgcggca gctggacctc agtcccgggt    3360
gctgaagcct tgaaggcctc tcttcccaaa gtccagggaa gaaacctgag cttctggctg    3420
tccacaggag aagagagcct atgtgggcat cctttatgca ggccagcggg ccatttctct    3480
ctcgctcctc tcagctgctc ttccaaaggc agaaaactgc gaggcaggaa accaaagata    3540
taaatacaga ttccacgccc accgggaagg ggggcccatc cagcaaacac tagaccggag    3600
ctgggatttt cacagcagtc ttcctccctg ttccagctcc ctctcactgc atgcttcagc    3660
gtgacctggg gtgatttcag agcctttgga ccatcaagca agattccctc tgagaatcca    3720
gggagcatca tgaaggctac agcacataca gctggatatt cccacacaac atacgatgga    3780
agcatttatt tatttattat gcattttatt ctgaatgaat ttgaagcaaa acaccagctt    3840
ttccaggctc tttggggtca gctggggtga ggaacgctcc tggggtgccc atcgacaggc    3900
ctcactgagg caaacccatt ttgagtgact tgaggcctct caagtttgtt ctccagggac    3960
tggctttgtt tctactgtga ctgactttaa attacagtgt ttgcaatggc attgctctga    4020
atggatctcg aaggaccaag ttgttttaaa aagaagaaga tgaattc                  4067

<210> SEQ ID NO 16
<211> LENGTH: 167
<212> TYPE: PRT
<213> ORGANISM: Bos taurus

<400> SEQUENCE: 16

Met Arg Cys Gly Pro Leu Tyr Arg Phe Leu Trp Leu Trp Pro Tyr Leu
1               5                   10                  15

Ser Tyr Val Glu Ala Val Pro Ile Arg Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Arg Val Thr Gly Leu Asp Phe Ile Pro
    50                  55                  60

Gly Leu His Pro Leu Leu Ser Leu Ser Lys Met Asp Gln Thr Leu Ala
65                  70                  75                  80

Ile Tyr Gln Gln Ile Leu Thr Ser Leu Pro Ser Arg Asn Val Val Gln
                85                  90                  95

Ile Ser Asn Asp Leu Glu Asn Leu Arg Asp Leu Leu His Leu Leu Ala
            100                 105                 110

Ala Ser Lys Ser Cys Pro Leu Pro Gln Val Arg Ala Leu Glu Ser Leu
        115                 120                 125

Glu Ser Leu Gly Val Val Leu Glu Ala Ser Leu Tyr Ser Thr Glu Val
    130                 135                 140

Val Ala Leu Ser Arg Leu Gln Gly Ser Leu Gln Asp Met Leu Arg Gln
145                 150                 155                 160
```

```
-continued

Leu Asp Leu Ser Pro Gly Cys
            165

<210> SEQ ID NO 17
<211> LENGTH: 18
<212> TYPE: PRT
<213> ORGANISM: Homo sapiens

<400> SEQUENCE: 17

Cys Ser Thr Gln Thr His Lys Ile Met Glu Asn Lys Met Cys Asp Leu
1               5                   10                  15
Thr Val

<210> SEQ ID NO 18
<211> LENGTH: 17
<212> TYPE: PRT
<213> ORGANISM: Homo sapiens

<400> SEQUENCE: 18

Lys Leu Glu Gly Asn Phe Pro Glu Glu Asn Asn Asp Lys Lys Ser Ile
1               5                   10                  15
Tyr

<210> SEQ ID NO 19
<211> LENGTH: 17
<212> TYPE: PRT
<213> ORGANISM: Homo sapiens

<400> SEQUENCE: 19

Ile Thr Asp Asp Gly Asn Leu Lys Ile Ser Trp Ser Ser Pro Pro Leu
1               5                   10                  15
Val

<210> SEQ ID NO 20
<211> LENGTH: 15
<212> TYPE: PRT
<213> ORGANISM: Homo sapiens

<400> SEQUENCE: 20

Cys Ser Asp Ile Pro Ser Ile His Pro Ile Ser Glu Pro Lys Asp
1               5                   10                  15

<210> SEQ ID NO 21
<211> LENGTH: 15
<212> TYPE: PRT
<213> ORGANISM: Homo sapiens

<400> SEQUENCE: 21

Cys Val Ile Val Ser Trp Ile Leu Ser Pro Ser Asp Tyr Lys Leu
1               5                   10                  15
```